United States Patent
Luesch et al.

(10) Patent No.: US 11,718,645 B2
(45) Date of Patent: Aug. 8, 2023

(54) MACROCYCLIC THERAPEUTIC AGENTS, METHODS OF MANUFACTURE, AND METHODS OF TREATMENT

(71) Applicant: University of Florida Research Foundation, Incorporated, Gainesville, FL (US)

(72) Inventors: Hendrik Luesch, Gainesville, FL (US); Qi-Yin Chen, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 534 days.

(21) Appl. No.: 16/857,934

(22) Filed: Apr. 24, 2020

(65) Prior Publication Data

US 2020/0317732 A1    Oct. 8, 2020

Related U.S. Application Data

(63) Continuation of application No. 16/272,636, filed on Feb. 11, 2019, now abandoned, which is a continuation of application No. 15/120,356, filed as application No. PCT/US2015/016743 on Feb. 20, 2015, now abandoned.

(60) Provisional application No. 61/942,495, filed on Feb. 20, 2014.

(51) Int. Cl.

| | | |
|---|---|---|
| C07K 5/12 | (2006.01) | |
| A61K 31/424 | (2006.01) | |
| A61K 31/429 | (2006.01) | |
| C07D 207/16 | (2006.01) | |
| A61K 45/06 | (2006.01) | |
| C07K 5/107 | (2006.01) | |
| A61K 38/12 | (2006.01) | |

(52) U.S. Cl.
CPC .......... *C07K 5/126* (2013.01); *A61K 31/424* (2013.01); *A61K 31/429* (2013.01); *A61K 38/12* (2013.01); *A61K 45/06* (2013.01); *C07D 207/16* (2013.01); *C07K 5/1016* (2013.01)

(58) Field of Classification Search
CPC .... C07K 5/126; C07K 5/1016; A61K 31/424; A61K 31/429; A61K 38/12; A61K 45/06; C07D 207/16
See application file for complete search history.

(56) References Cited

U.S. PATENT DOCUMENTS

| | | |
|---|---|---|
| 8,349,885 B2 | 1/2013 | Kim et al. |
| 9,181,304 B2 | 11/2015 | Luesch |
| 2014/0088016 A1 | 3/2014 | Luesch |
| 2016/0060299 A1 | 3/2016 | Luesch |
| 2017/0057996 A1 | 3/2017 | Luesch et al. |
| 2019/0241611 A1 | 8/2019 | Luesch et al. |

FOREIGN PATENT DOCUMENTS

| | | | |
|---|---|---|---|
| WO | WO 2009/032338 A1 | 3/2009 | |
| WO | WO 2009/032351 A1 | 3/2009 | |
| WO | WO 2009/082152 A2 | 7/2009 | |
| WO | WO 2009/088192 A2 | 7/2009 | |
| WO | WO 2009/091618 A1 | 7/2009 | |
| WO | WO 2010/065563 A2 | 6/2010 | |
| WO | WO 2011/112893 A2 | 9/2011 | |
| WO | WO 2012/158933 A2 | 11/2012 | |
| WO | WO-2012158933 A2 * | 11/2012 | ............. A61K 38/15 |

OTHER PUBLICATIONS

PubChem CID 125415 (Year: 2005).*
Extended European Search Report dated Oct. 25, 2017 for Application No. EP 15751780.6.
International Search Report and Written Opinion, dated May 22, 2015, in connection with Application No. PCT/US2015/016743.
Extended European Search Report dated Oct. 16, 2014 in connection with EP 12785060.0.
International Search Report and Written Opinion for PCT/US2012/038374 dated Jan. 29, 2013.
[No Author Listed] National Center for Biotechnology Information. PubChem Compound Database; CID= 125415, https://pubchem.ncbi.nlm.nih.gov/compound/125415.
Chen et al., Improved Total Synthesis and Biological Evaluation of Potent Apratoxin S4 Based Anticancer Agents with Differential Stability and Further Enhanced Activity, J. Med. Chem. Apr. 10, 2014;57(7):3011-29. doi: 10.1021/jm4019965. Epub Mar. 24, 2014.
Chen et al., Systematic Chemical Mutagenesis Identifies a Potent Novel Apratoxin A/E Hybrid with Improved in Vivo Antitumor Activity, ACS Med. Chem. Lett. Nov. 10, 2011;2(11):861-865. Epub Aug. 31, 2011.
Doi et al., Solid-phase total synthesis of (−)-apratoxin A and its analogues and their biological evaluation. Chem Asian J. Jan. 3, 2011;6(1):180-8. doi: 10.1002/asia.201000549.
Luesch et al., New apratoxins of marine cyanobacterial origin from Guam and Palau. Bioorg Med Chem. Jun. 2002;10(6):1973-8.
Nagarajan et al., A review of pharmacological and toxicological potentials of marine cyanobacterial metabolites. J Appl Toxicology. 2012;32(3):153-85.

* cited by examiner

*Primary Examiner* — Jeffrey S Lundgren
*Assistant Examiner* — Ibrahim D Bori
(74) *Attorney, Agent, or Firm* — Wolf, Greenfield & Sacks, P.C.

(57) ABSTRACT

The instant invention describes macrocyclic compounds having therapeutic activity, and the mechanism and methods of treating disorders such as autoimmune diseases, inflammation, and cancer, tumors and cell proliferation related disorders.

20 Claims, 2 Drawing Sheets

MACROCYCLIC THERAPEUTIC AGENTS, METHODS OF MANUFACTURE, AND METHODS OF TREATMENT

CROSS-REFERENCE TO RELATED APPLICATIONS

This application is a Continuation Application of U.S. application Ser. No. 16/272,636, filed Feb. 11, 2019, which is a Continuation Application of U.S. application Ser. No. 15/120,356, filed Aug. 19, 2016, which is the U.S. National Stage, pursuant to 35 U.S.C. § 371, of U.S. International Application No. PCT/US2015/016743, filed Feb. 20, 2015, designating the United States and published on Aug. 27, 2015 as Publication WO 2015/127161, which claims the benefit of U.S. Provisional Application No. 61/942,495, filed Feb. 20, 2014, the entire contents of which are incorporated herein by reference.

STATEMENT OF RIGHTS TO INVENTIONS MADE UNDER FEDERALLY SPONSORED RESEARCH

This invention was made with government support under Grant No. R01CA172310 awarded by the National Institute of Health (NIH) and National Cancer Institute (NCI). The government has certain rights in the invention.

BACKGROUND

The identification of new pharmacophores is of paramount biomedical importance and natural products have recently been regaining attention for this endeavor [Koehn, F. E.; Carter, G. T. Nat. Rev. Drug Discov. 2005, 4, 206-220; Paterson, I.; Anderson, E. A. Science 2005, 310, 451-453]. This renaissance is closely tied to the successful exploitation of the marine environment which harbors unmatched biodiversity that is presumably concomitant with chemical diversity [Fenical, W.; Jensen, P. R. Nat. Chem. Biol. 2006, 2, 666-673]. In particular, marine cyanobacteria are prolific producers of bioactive secondary metabolites, many of which are modified peptides or peptide-polyketide hybrids with promising antitumor activities, such as dolastatin 10, curacin A, and apratoxin A [Gerwick, W. H.; Tan, L. T.; Sitachitta, N. Alkaloids Chem. Biol. 2001, 57, 75-184; Luesch, H.; Moore, R. E.; Paul, V. J.; Mooberry, S. L.; Corbett, T. H. J. Nat. Prod. 2001, 64, 907-910; Gerwick, W. H.; Proteau, P. J.; Nagle, D. G.; Hamel, E.; Blokhin, A.; Slate, D. L. J. Org. Chem. 1994, 59, 1243-1245; Verdier-Pinard, P.; Lai, J.-Y.; Yoo, H.-D.; Yu, J.; Marquez, B.; Nagle, D. G.; Nambu, M.; White, J. D.; Falck, J. R.; Gerwick, W. H.; Day, B. W.; Hamel, E. Mol. Pharmacol. 1998, 53, 62-76; Luesch, H.; Yoshida, W. Y.; Moore, R. E.; Paul, V. J.; Corbett, T. H. J. Am. Chem. Soc. 2001, 123, 5418-5423; Luesch, H.; Chanda, S. K.; Raya, M. R.; DeJesus, P. D.; Orth, A. P.; Walker, J. R.; Izpisúa Belmonte, J. C.; Schultz, P. G. Nat. Chem. Biol. 2006, 2, 158-167].

Apratoxins are potent cytotoxins derived from marine cyanobacteria and, due to their biological activity and intriguing structures, they have been subject to several total syntheses and SAR studies [Luesch, H.; Yoshida, W. Y.; Moore, R. E.; Paul, V. J.; Corbett, T. H. J. Am. Chem. Soc. 2001, 123, 5418-5423; Luesch, H.; Yoshida, W. Y.; Moore, R. E.; Paul, V. J.; Bioorg. Med. Chem. 2002, 10, 1973-1978; Matthew, S.; Schupp, P. J.; Luesch, H. J. Nat. Prod. 2008, 71, 1113-1116; Gutierrez, M.; Suyama, T. L.; Engene, N.; Wingerd, J. S.; Matainaho, T.; Gerwick, W. H. J. Nat. Prod. 2008, 71, 1099-1103; Tidgewell, K.; Engene, N.; Byrum, T.; Media, J.; Doi, T.; Valeriote, F. A.; Gerwick, W. H. Chem Bio Chem 2010, 11, 1458-1466; Thornburg, C. C.; Cowley, E. S.; Sikorska, J.; Shaala, L. A.; Jane E. Ishmael, J. E.; Youssef, D. T. A.; McPhail, K. L. J. Nat. Prod. 2013, 76, 1781-1788; Chen, Q.-Y.; Liu, Y.; Luesch, H. Med. Chem. Lett. 2011, 2, 861-865; Doi, T.; Numajiri, Y.; Munakata, A.; Takahashi, T. Org. Lett. 2006, 8, 531-534; Numajiri, Y.; Takahashi, T.; Doi, T. Chem. Asian J. 2009, 4, 111-125; Xu, Z.; Chen, Z.; Ye, T. Tetrahedron: Asymmetry 2004, 15, 355-363; Doi, T.; Numajiri, Y.; Takahashi, T.; Takagi, M.; Shin-ya, K. Chem. Asian J. 2011, 6, 180-188; Chen, J.; Forsyth, C. J. J. Am. Chem. Soc. 2003, 125, 8734-8735; Ma, D.; Zou, B.; Cai, G.; Hu, X.; Liu, J. O. Chem. Eur. J. 2006, 12, 7615-7626; Zou, B.; Wei, J.; Cai, G.; Ma, D. Org. Lett. 2003, 5, 3503-3506; Gilles, A.; Martinez, J.; Cavelier, F. J. Org. Chem. 2009, 74, 4298-4304; Robertson, B. D.; Wengryniuk, S. E.; Coltart, D. M. Org. Lett., 2012, 14, 5192-5195]. Apratoxins have been shown to prevent cotranslational translocation and thereby downregulate various receptors, including receptor tyrosine kinases (RTKs), and inhibit trafficking of other secretory molecules, including growth factors that act on RTKs [Chen, Q.-Y.; Liu, Y.; Luesch, H. ACS Med. Chem. Lett. 2011, 2, 861-865; Liu, Y.; Law, B. K.; Luesch, H. Mol. Pharmacol. 2009,76, 91-104]. RTKs such as epidermal growth factor receptors and corresponding ligands such as vascular endothelial growth factor A (VEGF-A) individually are validated drug targets, which resulted in the approval of small molecules and antibodies against these proteins for colorectal cancer and other cancers [Lurje, G.; Lenz, H.-J. Oncology 2009, 77, 400-410; Hurwitz, H.; Fehrenbacher, L.; Novotny, W.; Cartwright, T.; Hainsworth, J.; Heim, W.; Berlin, J.; Baron, A.; Griffing, S.; Holmgren, E.; Ferrara, N.; Fyfe, G.; Rogers, B.; Ross, R.; Kabbinavar, F. N. Engl. J. Med. 2004, 350, 2335-2342; Koutras, A. K.; Starakis, I.; Kyriakopoulou, U.; Katsaounis, P.; Nikolakopoulos, A.; Kalofonos, H. P. Curr. Med. Chem. 2011, 18, 1599-1612]. The combined indirect inhibition of both classes of molecules by apratoxins has proven very powerful and an alternative to the specific targeting of selected secretory proteins in cancers that rely on autocrine loops, such as colorectal cancer [Chen, Q.-Y.; Liu, Y.; Luesch, H. ACS Med. Chem. Lett. 2011, 2, 861-865; Ruan, W.-J.; Lai, M.-D. Med. Oncol. 2004, 21, 1-7]. Apratoxin A has been shown to possess broad-spectrum yet differential in vitro activity; however, it also demonstrated in vivo toxicity and sub-optimal tolerability [Luesch, H.; Chanda, S. K.; Raya, R. M.; DeJesus, P. D.; Orth, A. P.; Walker, J. R.; Izpisúa Belmonte, J. C.; Schultz, P. G. Nat Chem Biol. 2006, 2, 158-167; Chen, Q.-Y.; Liu, Y.; Luesch, H. ACS Med. Chem. Lett. 2011, 2, 861-865]. Therefore, the compounds of the present invention were designed and synthesized to address these shortcomings while maintaining or improving biological activity.

As a result of ongoing investigations to identify new drug leads from cyanobacteria, we report here the biological characterization of activity for a class of a marine cyanobacterial metabolites and synthetic analogues with novel chemical scaffold and nanomolar antiproliferative activity. These findings provide new alternatives to address unmet needs in the treatment of proliferation diseases and disorders.

Modulation of cellular activity by apratoxins may be beneficial for cancer treatment and for immunosuppression, e.g., based on downregulation of receptors, inhibition of STAT3 activity and of T-cell activation. As such, other diseases that may be treated with apratoxin-based agents include other diseases where receptor downregulation may be beneficial, e.g., autoimmune diseases, some which may be associated with chemokine receptors (e.g., multiple sclerosis), or inflammation. These findings provide new alternatives to address unmet needs in the treatment of the aforementioned diseases, disorders, and symptoms thereof. Modulation of cellular activity by apratoxins may also be beneficial to disorders that are associated with enhanced secretory pathway activity.

BRIEF SUMMARY OF THE INVENTION

The invention is directed towards macrocyclic compounds and methods of synthesis, their mechanism of action, methods of modulating proliferation activity, and methods of treating proliferation disease and disorders.

In one embodiment, the invention provides a compound according to formula 1 or formula 2:

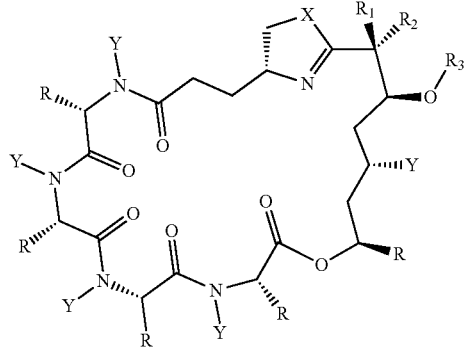

(1)

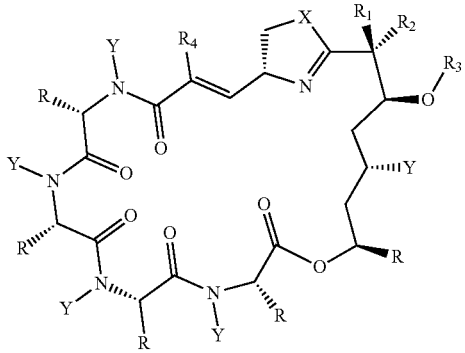

(2)

wherein
each X is independently S or O;
each Y is independently H or optionally substituted alkyl;
Each R is independently alkyl optionally substituted with OH, OMe, SH, SMe, optionally substituted phenyl, $NH_2$, NH-alkyl, or N(alkylxalkyl); or each R is independently the side chain of a naturally-occurring or non-natural amino acid (including, e.g., phenylalanine, tyrosine, tryptophan, histidine, serine, methionine, and the like);

or wherein each Y and R and the adjacent atoms attached to them (nitrogen and carbon, respectively) can combine to form a heterocyclic ring (e.g., 5-, 6-, or 7-membered heterocyclic ring);

each $R_1$ and $R_2$ are independently H or optionally substituted alkyl;

each $R_3$ is independently H, optionally substituted alkyl, or —C(O)alkyl; and each $R_4$ is H or optionally substituted alkyl;

and pharmaceutically acceptable salts, solvates, prodrugs, or hydrates thereof.

In one embodiment, the invention provides a compound according to any of the formula 3 or formula 4:

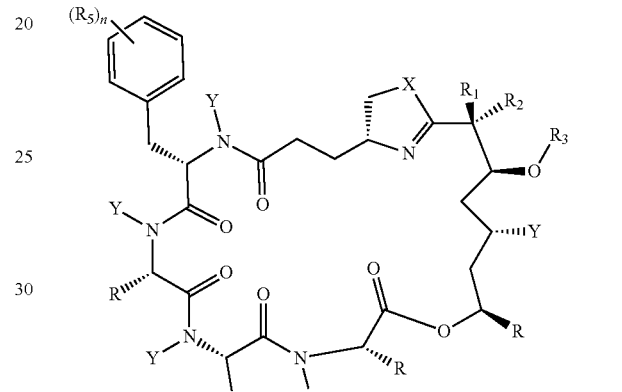

(3)

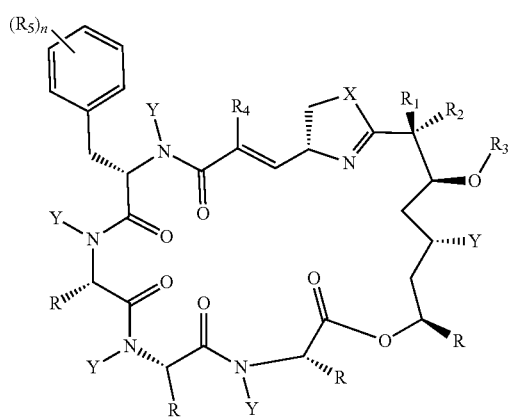

(4)

wherein:
each n is independently 0, 1, 2, 3, or 4;
each $R_5$ is independently OH, SH, thioalkoxy, alkoxy, halo, $NH_2$, NH-alkyl, or N(alkyl)(alkyl); and
the remaining variables are as described above (i.e., in formulae 1-2);
and pharmaceutically acceptable salts, solvates, or hydrates thereof.

In other aspects, the compound is of any of the formulae 5 to 15 and 44 to 46 wherein the variables are as defined in formulae 1 or 2:
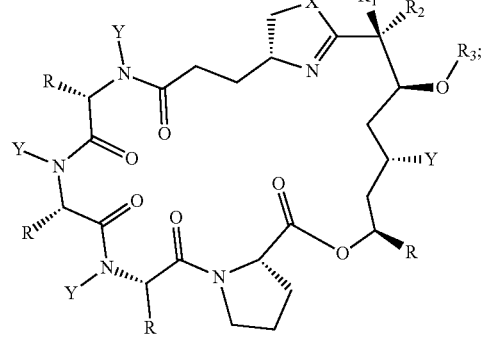
(5)
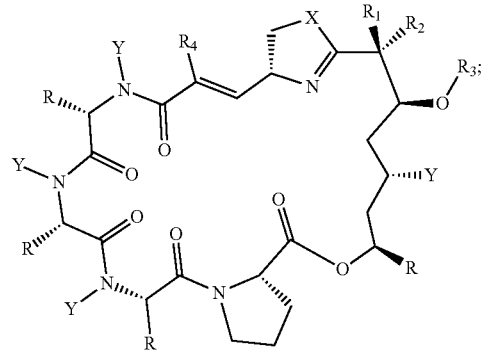
(6)
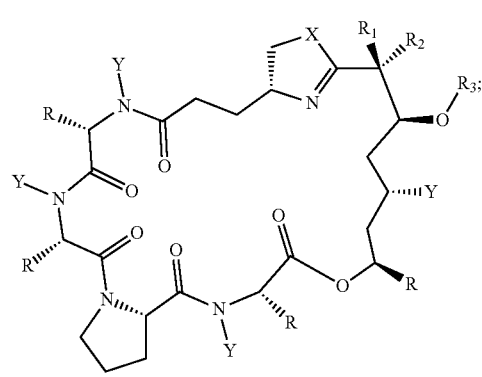
(7)
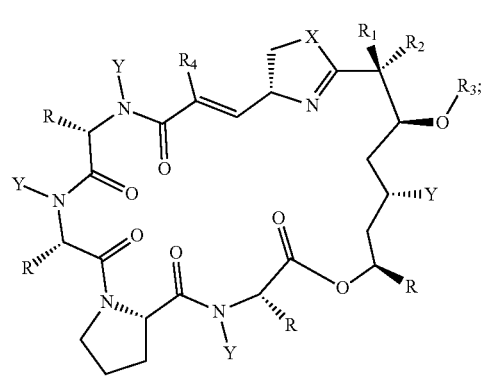
(8)
-continued
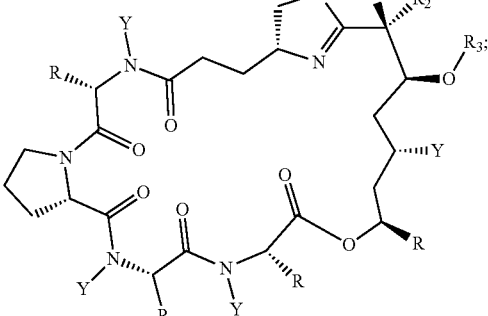
(9)
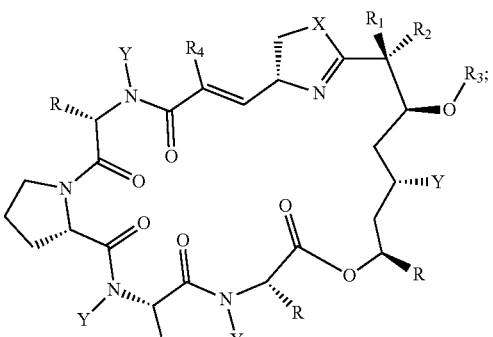
(10)
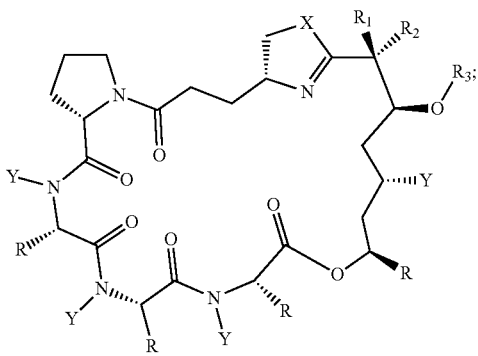
(11)
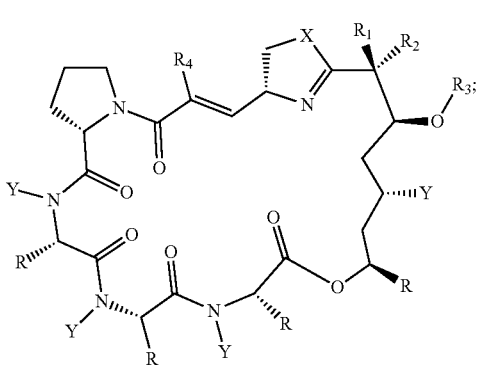
(12)

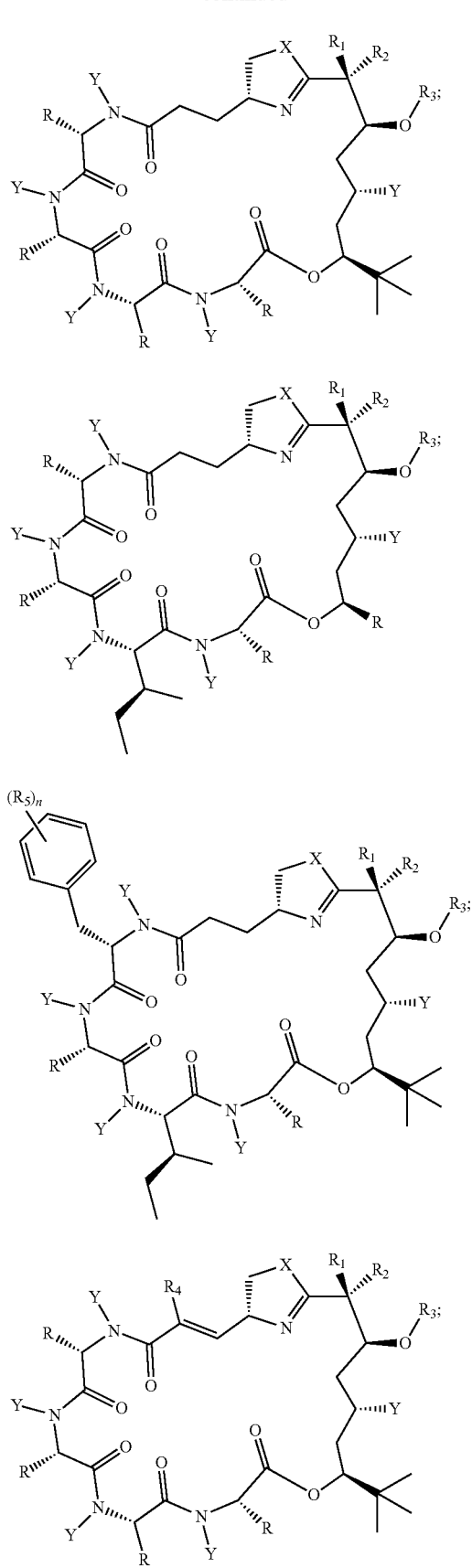
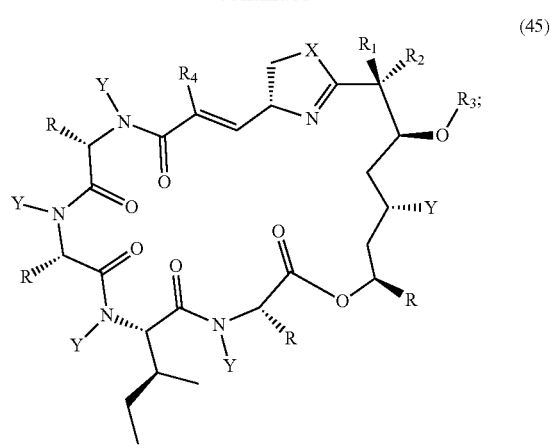
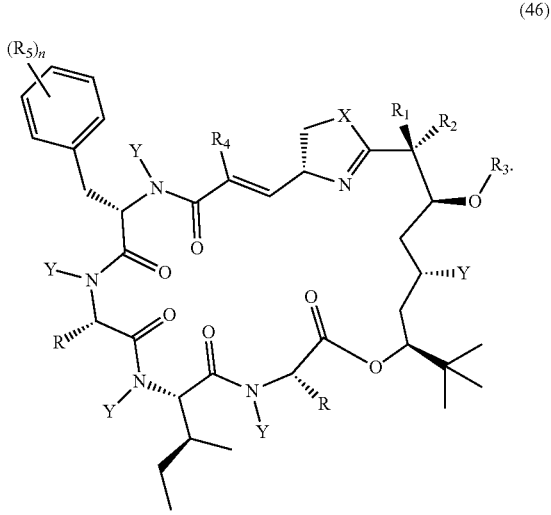
In other aspects, the compounds are those of the following formulae:
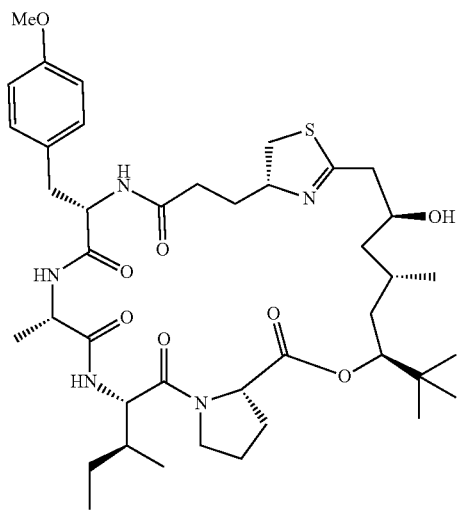

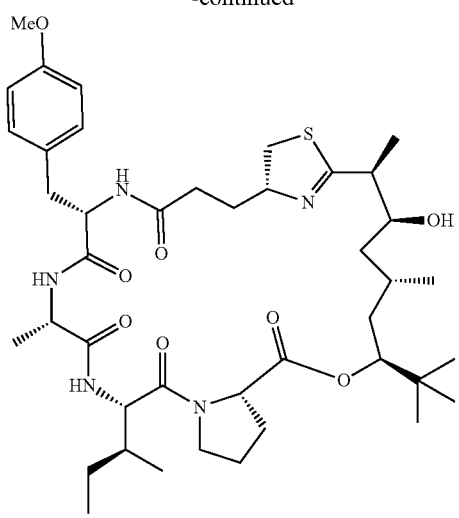
;
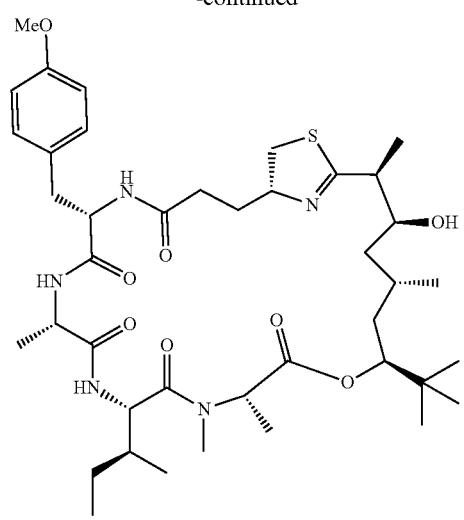
;
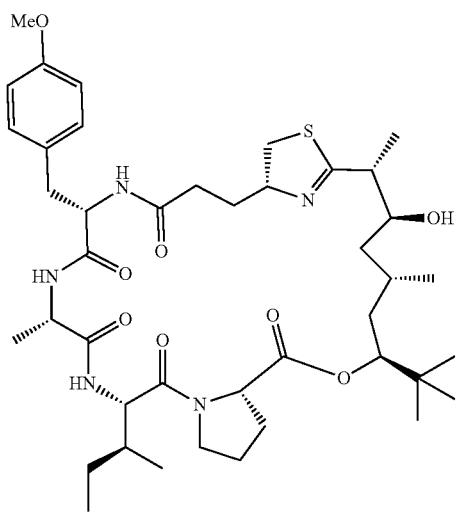
;
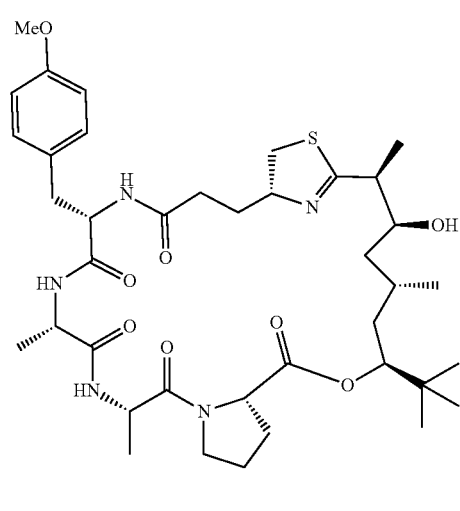
;
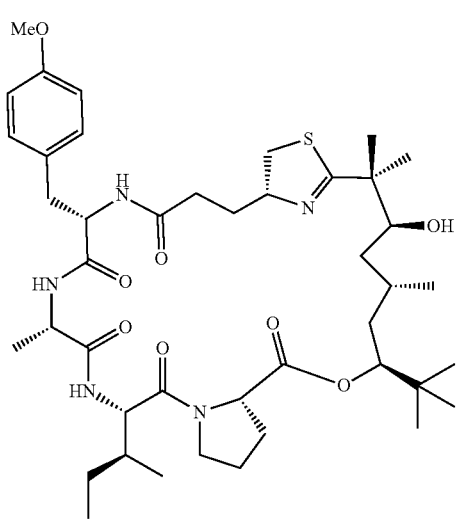
;
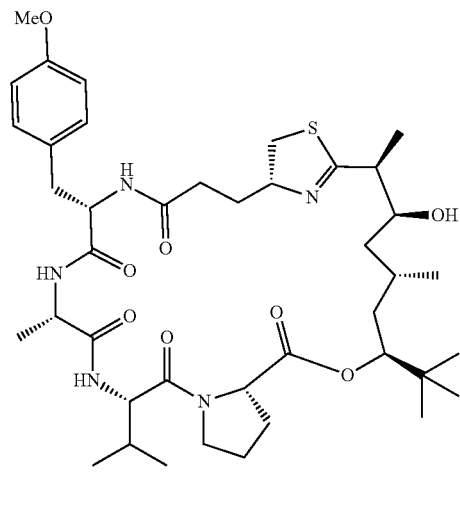
;

-continued

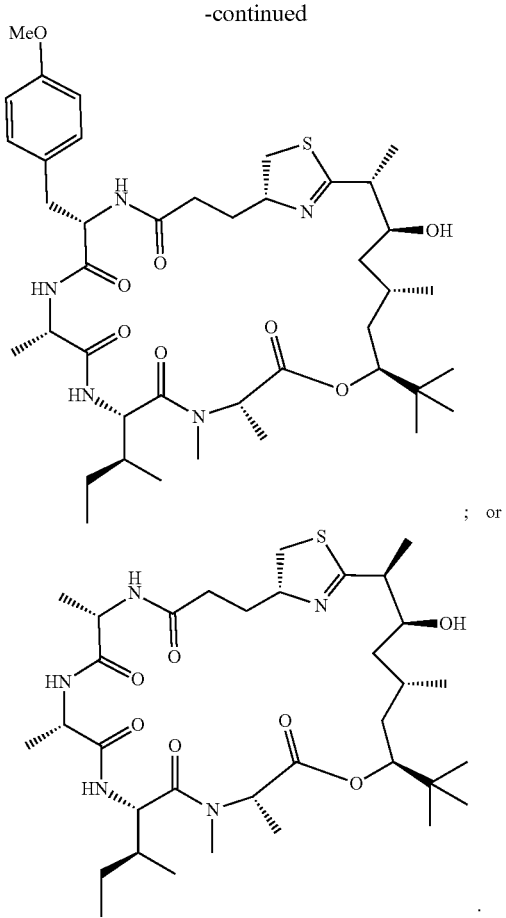

; or

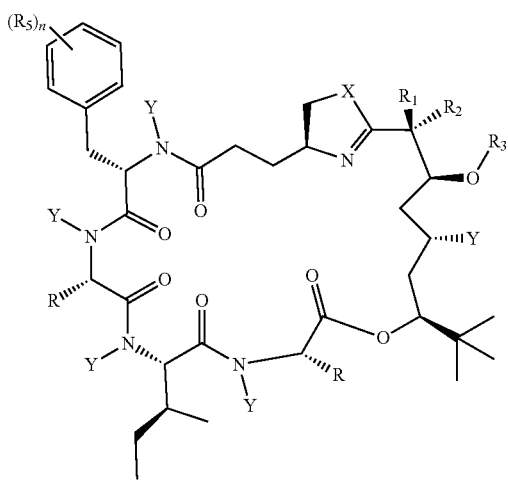

In one embodiment, the invention provides a compound according to a formula 34:

(34)

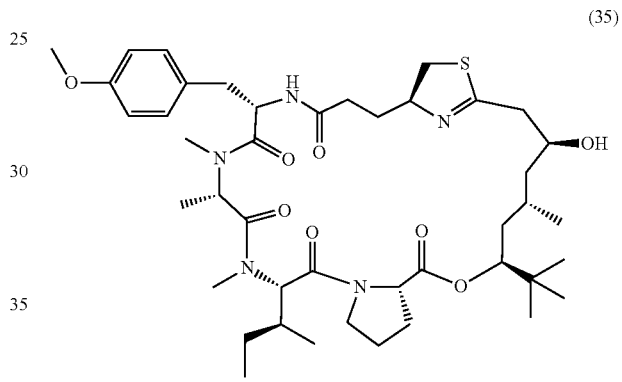

wherein
each X is independently S or O;
each Y is independently H or optionally substituted alkyl;
Each R is independently alkyl optionally substituted with OH, OMe, SH, SMe, optionally substituted phenyl, NH$_2$, NH-alkyl, or N(alkyl)(alkyl); or each R is independently the side chain of a naturally-occurring or non-natural amino acid (including, e.g., phenylalanine, tyrosine, tryptophan, histidine, serine, methionine, and the like);

or wherein each Y and R and the adjacent atoms attached to them (nitrogen and carbon, respectively) can combine to form a heterocyclic ring (e.g., 5-, 6-, or 7-membered heterocyclic ring);

each R$_1$ and R$_2$ are independently H or optionally substituted alkyl (R$_1$ is preferably optionally substituted alkyl);

each R$_3$ is independently H, optionally substituted alkyl, or —C(O)alkyl; and each R$_4$ is H or optionally substituted alkyl;

each n is independently 0, 1, 2, 3, or 4;

each R$_5$ is independently OH, SH, thioalkoxy, alkoxy, halo, NH$_2$, NH-alkyl, or N(alkyl)(alkyl);

and pharmaceutically acceptable salts, solvates, or hydrates thereof.

In another embodiment, the invention provides a compound according to any of the formulae:

(35)

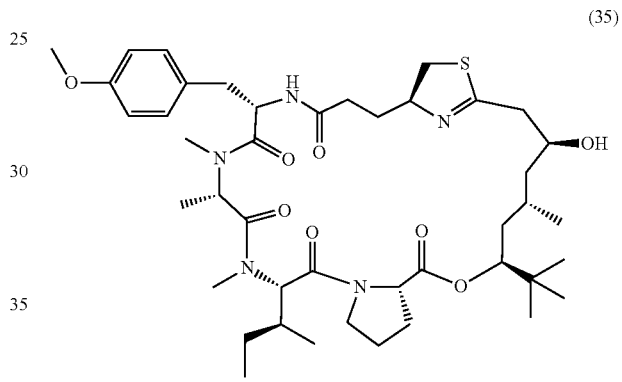

(36)

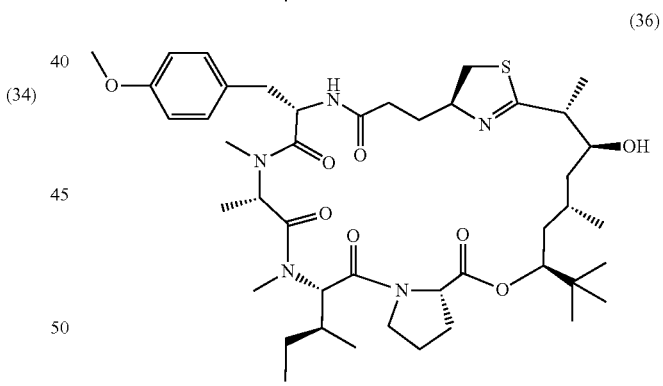

(37)

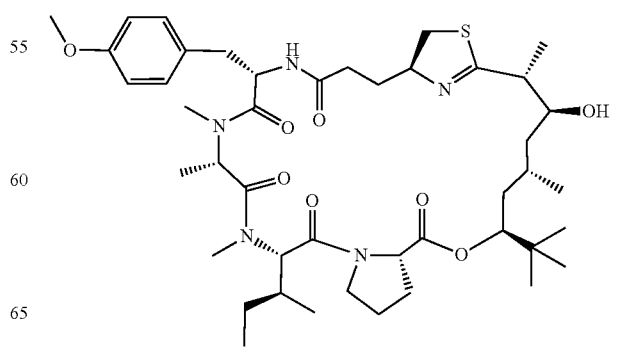

(38)
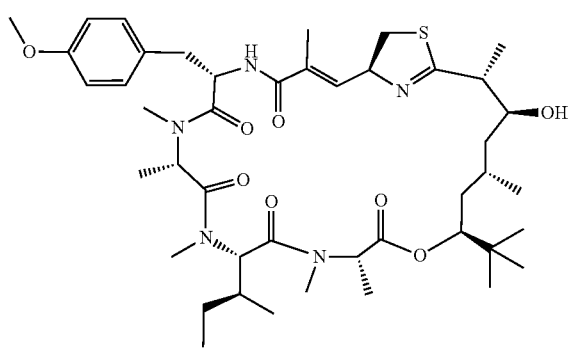

(39)
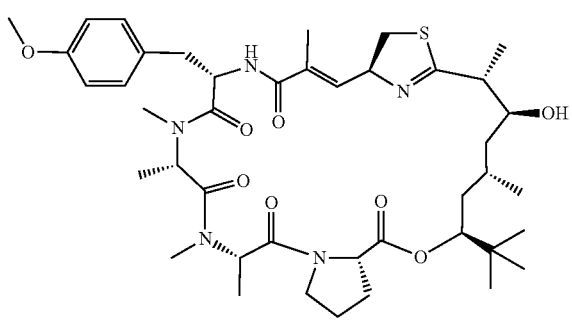

(40)
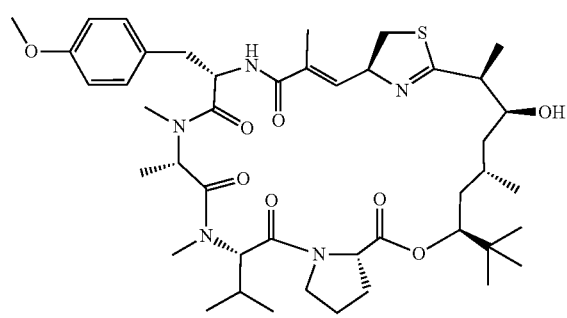

(41)
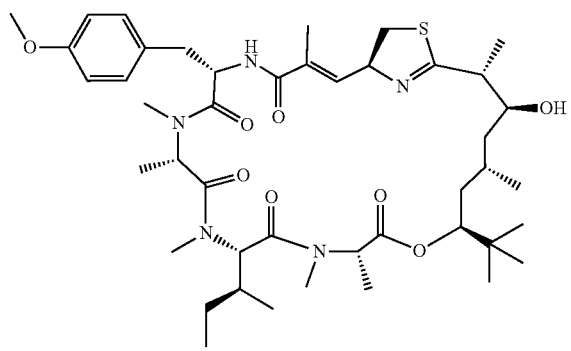

(42)
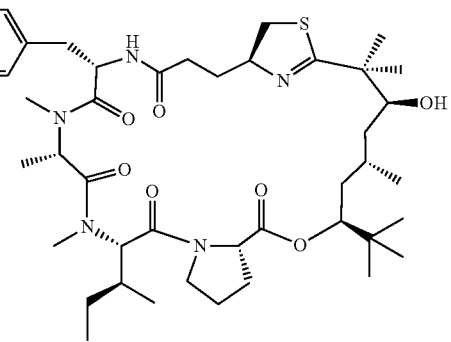

(43)
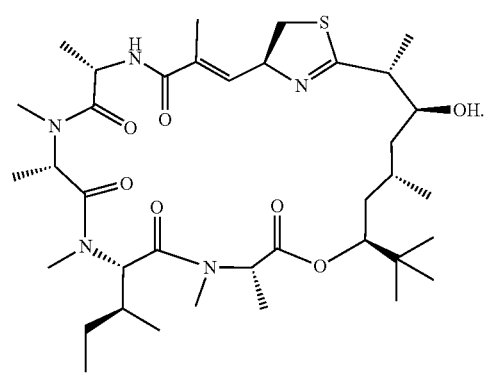

In another embodiment, the invention provides a compound according to formula 32:

(32)
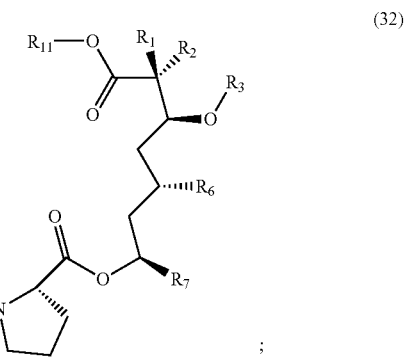

wherein each $R_1$ is independently H or optionally substituted alkyl;

each $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ is independently H or optionally substituted alkyl;

each $R_{10}$ is independently H or an amino protecting group; and each $R_{11}$ is independently H or a carboxylic acid protecting group;

provided that if $R_1$ is methyl, then $R_2$ is optionally substituted alkyl.

In another embodiment, the invention provides a compound according to formula 33:

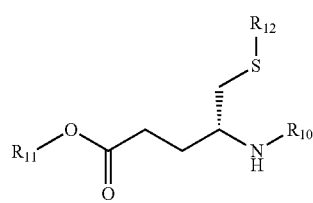
(33)

wherein each $R_{10}$ is independently H or an amino protecting group;

each $R_{11}$ is H or a carboxylic acid protecting group; and each $R_{12}$ is H or a thiol protecting group.

In another embodiment, the invention provides a compound according to formula 23a:

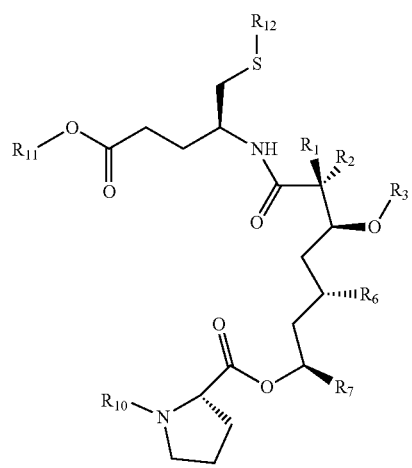
(23a)

wherein each $R_1$ is H or optionally substituted alkyl;

each $R_2$ is H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ is independently H or optionally substituted alkyl;

each $R_{10}$ is independently H or an amino protecting group;

each $R_{11}$ is H or a carboxylic acid protecting group; and each $R_{12}$ is H or a thiol protecting group;

provided that if $R_1$ is methyl, then $R_2$ is optionally substituted alkyl.

In another embodiment, the invention provides a compound according to formula 23b:

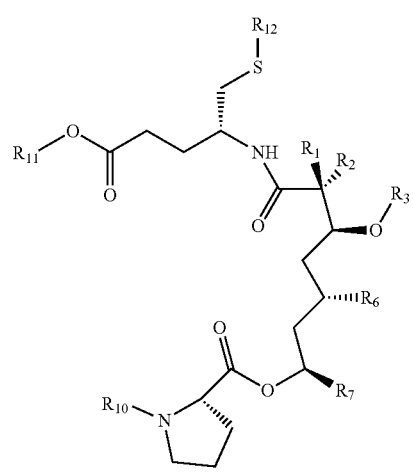
(23b)

wherein each $R_1$ is H or optionally substituted alkyl;

each $R_2$ is H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ is independently H or optionally substituted alkyl;

each $R_{10}$ is independently H or an amino protecting group;

each $R_{11}$ is H or a carboxylic acid protecting group; and each $R_{12}$ is H or a thiol protecting group.

In another embodiment, the invention provides a compound according to formula 27a:

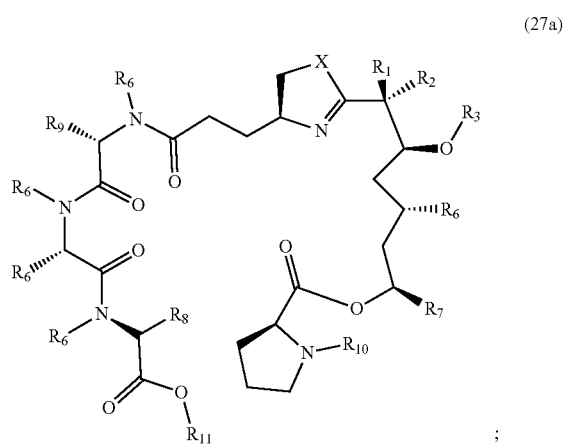
(27a)

wherein each X is S or O;

each $R_1$ is H or optionally substituted alkyl;

each $R_2$ is H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ are independently H or optionally substituted alkyl;

each $R_9$ is independently H, optionally substituted alkyl, or optionally substituted aralkyl;

each $R_{10}$ is independently H or an amino protecting group; and each $R_{11}$ is H or a carboxylic acid protecting group; and provided that if $R_1$ is methyl, then $R_2$ is optionally substituted alkyl.

In another embodiment, the invention provides a compound according to formula 27b:

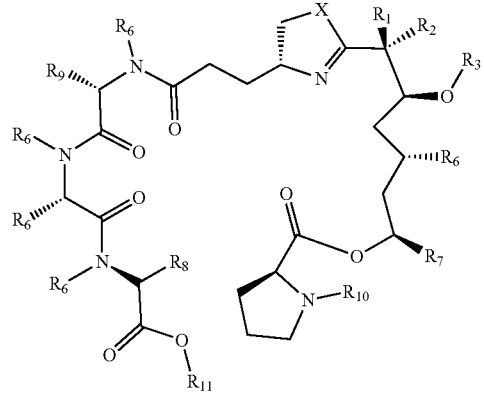

(27b)

wherein each X is S or O;

each $R_1$ is H or optionally substituted alkyl;

each $R_2$ is H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ are independently H or optionally substituted alkyl;

each $R_9$ is independently H, optionally substituted alkyl, or optionally substituted aralkyl;

each $R_{10}$ is independently H or an amino protecting group; and each $R_{11}$ is H or a carboxylic acid protecting group.

Another aspect is a compound herein, wherein X is S.

Another aspect is a compound herein, identified as an inhibitor of cotranslational translocation within the secretory pathway.

In another aspect, the invention provides a pharmaceutical composition comprising the compound of any of the formulae herein and a pharmaceutically acceptable carrier.

In another aspect, the invention provides a process to prepare a compound of formula 16 or formula 17:

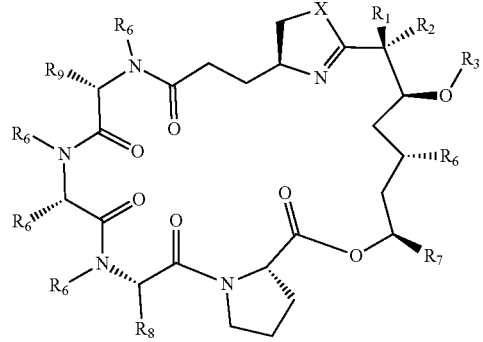

(16)

; or

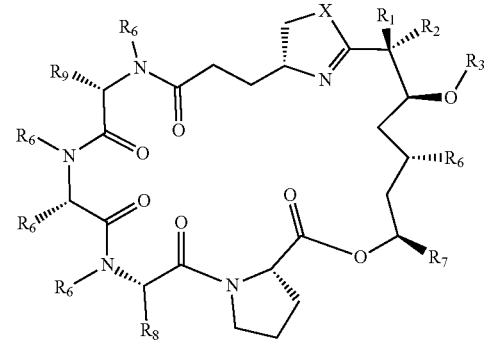

(17)

;

wherein the process comprises the step of reacting a compound of formula 18,

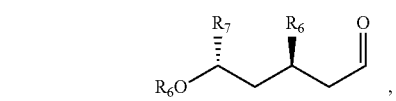

, with a compound of formula 19,

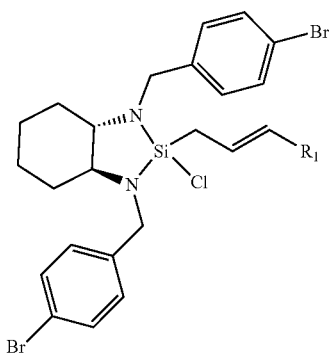

, to afford a compound of formula 20,

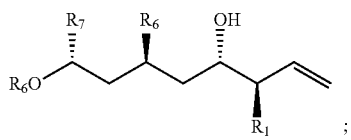

wherein
each X is independently S or O;
each $R_1$ is optionally substituted alkyl;
each $R_2$ is H;
each $R_3$ is independently H, optionally substituted alkyl, or —C(O)alkyl;
each $R_6$ is independently H, optionally substituted alkyl, or —C(O)alkyl;
each $R_7$ and $R_8$ are independently H or optionally substituted alkyl; and
each $R_9$ is independently H, optionally substituted alkyl, or optionally substituted aralkyl In another aspect, the invention provides a process to prepare a compound of formula 20:

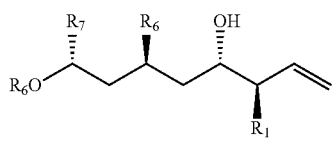

(20)

comprising reacting a compound of formula 18,

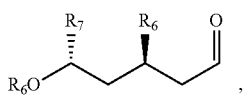

with a compound of formula 19,

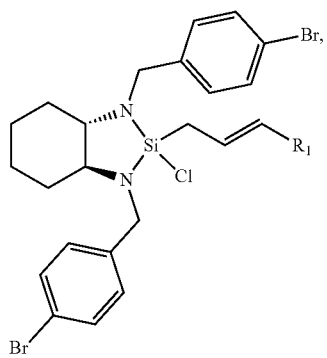

to afford a compound of formula 20;
wherein
each $R_1$ is optionally substituted alkyl;
each $R_6$ is independently H, optionally substituted alkyl, or —C(O)alkyl; and
each $R_7$ is independently H or optionally substituted alkyl.

In another aspect, the invention provides a process to prepare a compound of formula 16 or formula 17:

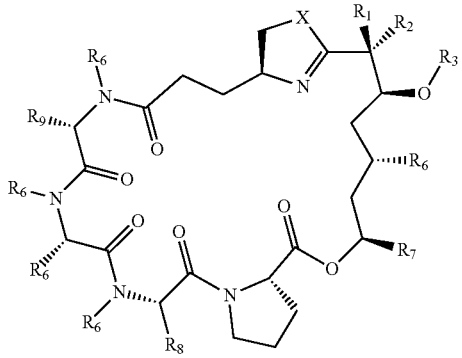

(16)

or

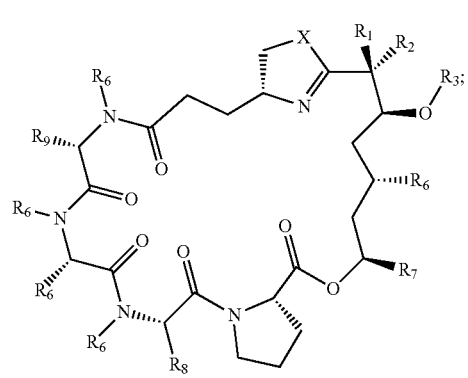

(17)

wherein the process comprises the step of reacting (i) a compound of formula 21,

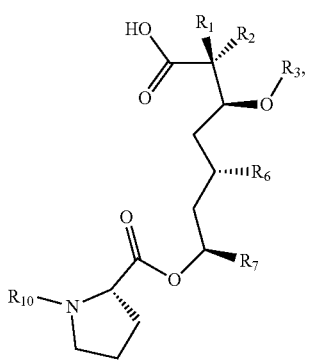

(ii) a compound of formula 22a,

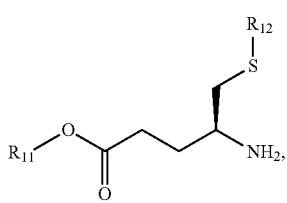

or a compound of formula 22b,

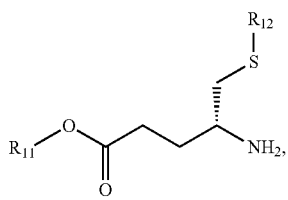

and (iii) a coupling reagent (preferably, BOP, BEP, PyAOP, or DEPBT) to afford a compound of formula 23a,

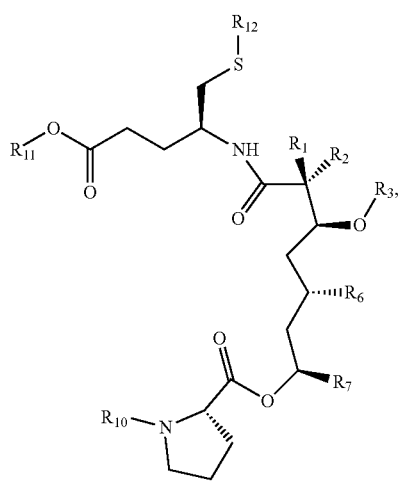

or formula 23b,

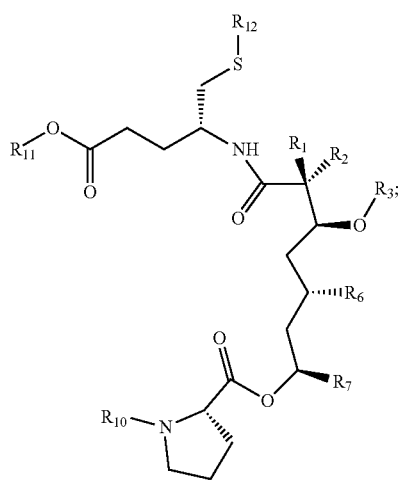

wherein
each X is S;
each $R_1$ and $R_2$ are H or optionally substituted alkyl;
each $R_3$ is independently H, optionally substituted alkyl, or —C(O)alkyl;
each $R_6$ is independently H, optionally substituted alkyl, or —C(O)alkyl;
each $R_7$ and $R_8$ are independently H or optionally substituted alkyl;

each $R_9$ is independently H, optionally substituted alkyl, or optionally substituted aralkyl;
each $R_{10}$ is independently an amino protecting group;
each $R_{11}$ is a carboxylic acid protecting group; and
each $R_{12}$ is a thiol protecting group.

In another aspect, the invention provides a process to prepare a compound of formula 23a or formula 23b:

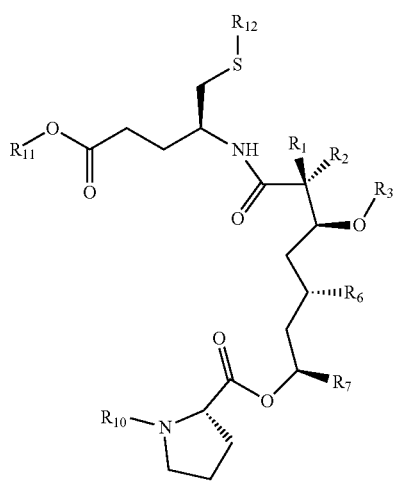

(23a)

or

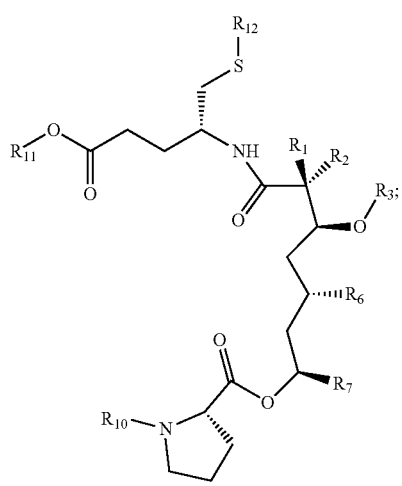

(23b)

comprising reacting (i) a compound of formula 21,

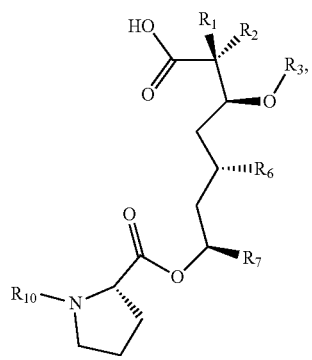

(ii) a compound of formula 22a,

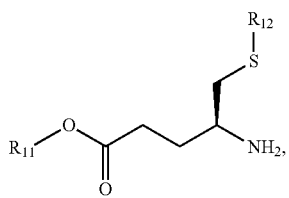

or a compound of formula 22b,

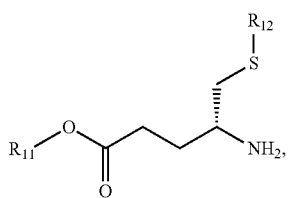

and (iii) a coupling reagent (preferably, BOP, BEP, PyAOP, or DEPBT) to afford a compound of formula 23a or formula 23b;

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ is independently H or optionally substituted alkyl;

each $R_{10}$ is independently an amino protecting group;

each $R_{11}$ is a carboxylic acid protecting group;

each $R_{12}$ is a thiol protecting group.

In another aspect, the invention provides a process to prepare a compound of formula 16 or formula 17:

(16)

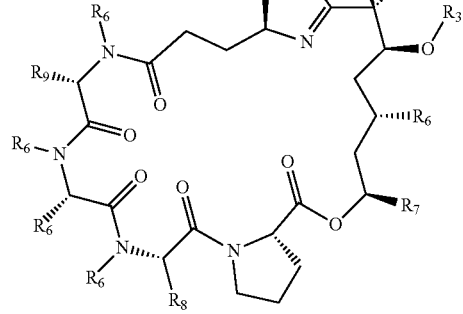

or (17)

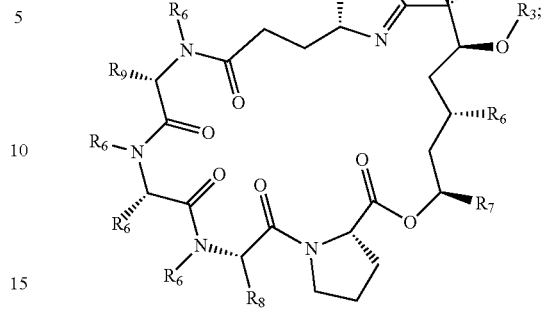

wherein the process comprises the step of reacting (i) a compound of formula 24a,

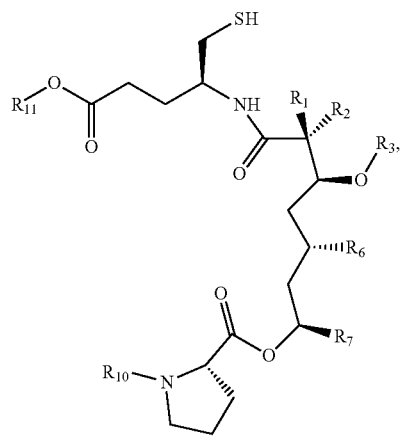

or formula 24b,

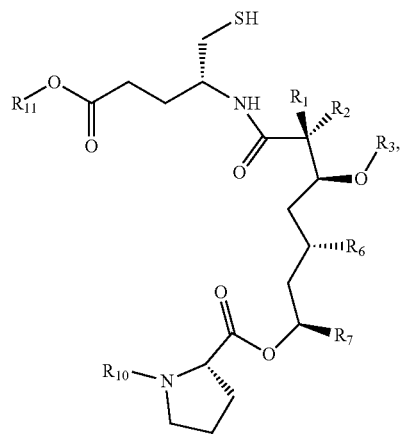

and (ii) a Lewis acid to afford a compound of formula 25a,

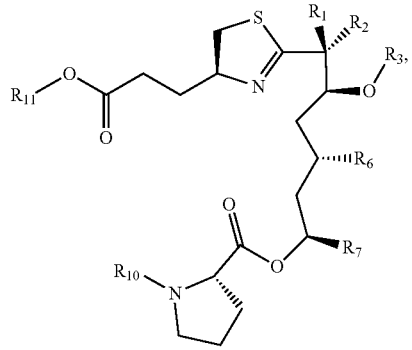

or formula 25b,

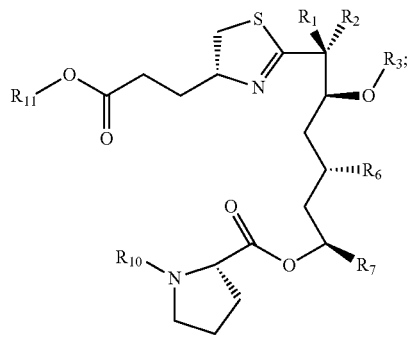

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group. In further embodiments, the process is conducted at a temperature between about 40° C. and about 100° C., between about 50° C. and 80° C., between about 55° C. and 65° C., and at about 60° C.

In another aspect, the invention provides a process to prepare a compound of formula 25a or formula 25b:

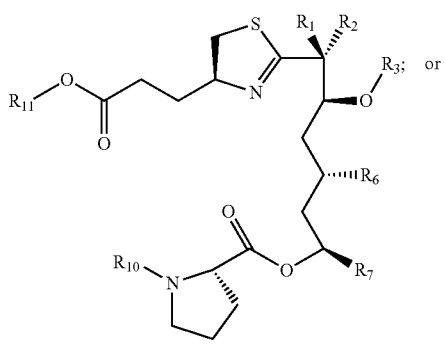

(25a)

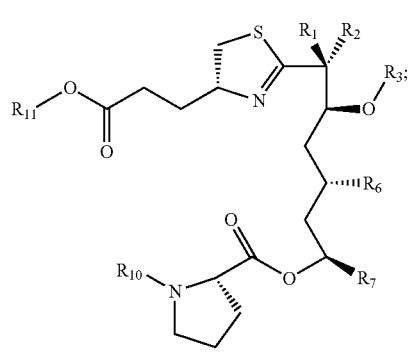

(25b)

comprising reacting (i) a compound of formula 24a,

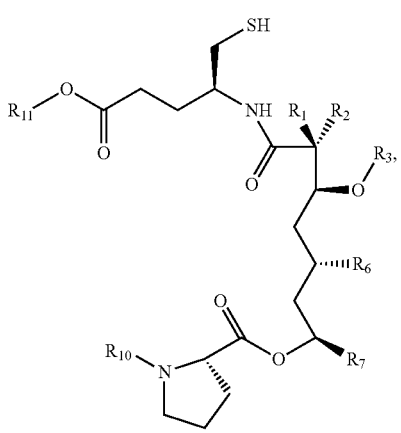

or formula 24b,

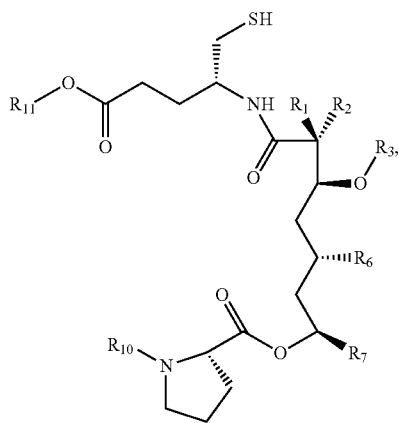

and (ii) a Lewis acid to afford a compound of formula 25a or formula 25b;
wherein
each X is S;
each $R_1$ and $R_2$ is independently H or optionally substituted alkyl;
each $R_3$ is independently H, optionally substituted alkyl, or —C(O)alkyl;
each $R_6$ is independently H, optionally substituted alkyl, or —C(O)alkyl;
each $R_7$ is independently H or optionally substituted alkyl;
each $R_{10}$ is independently an amino protecting group; and
each $R_{11}$ is a carboxylic acid protecting group.

In another aspect, the invention provides a process to prepare a compound of formula 16 or formula 17:

(16)

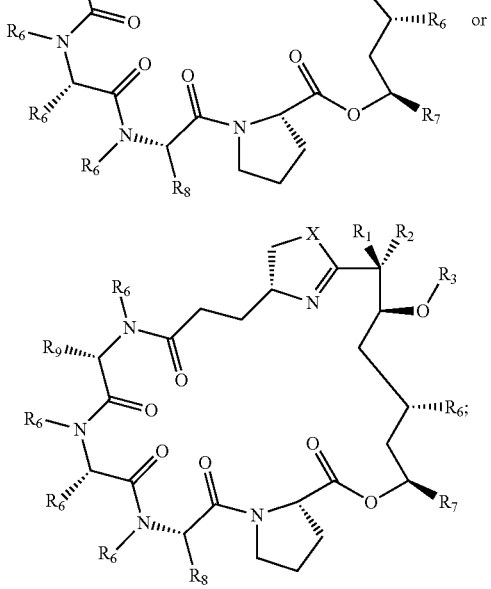

or (17)

wherein the process comprises the step of reacting (i) a compound of formula 26a,

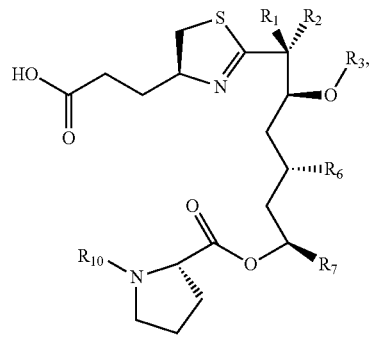

or formula 26b,

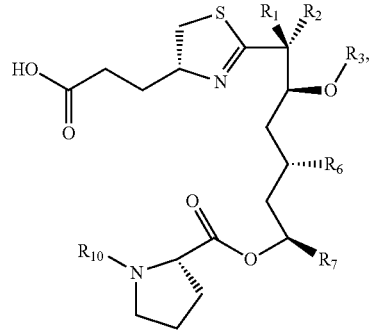

(ii) a compound of formula 26,

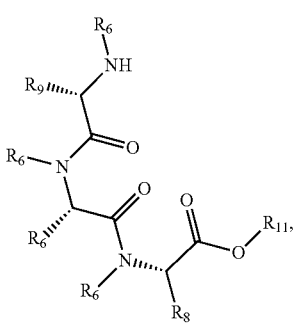

and (iii) a coupling reagent (preferably, BOP, BEP, PyAOP, or DEPBT) to afford a compound of formula 27a,

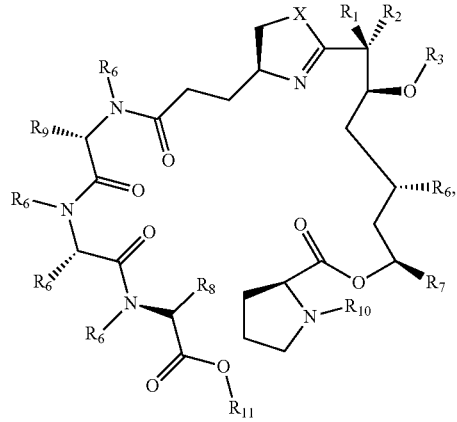

(27a)

or formula 27b,

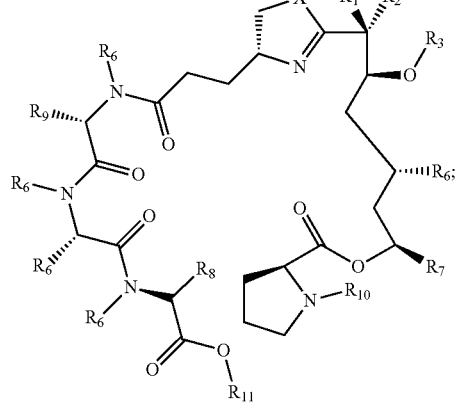

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group.

In another aspect, the invention provides a process to prepare a compound of formula 27a or formula 27b:

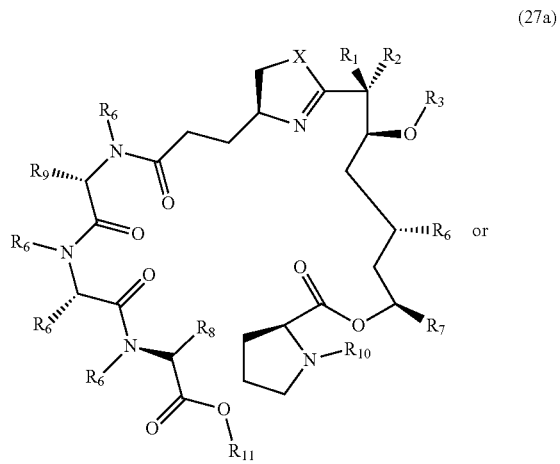

(27a)

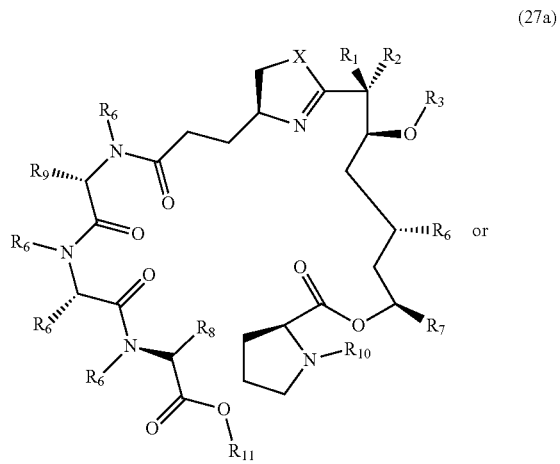 or (27b)

comprising reacting (i) a compound of formula 25a,

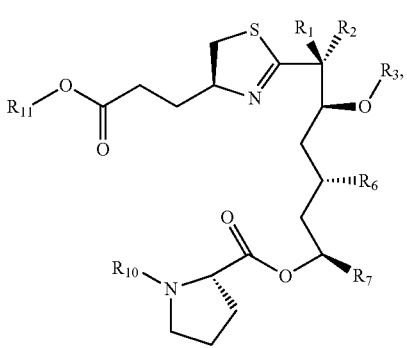

or formula 25b,

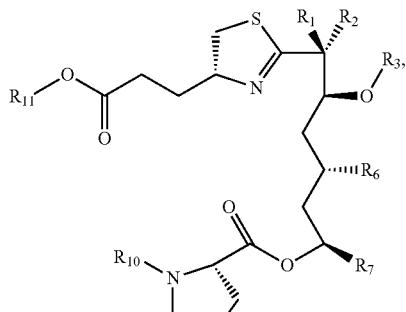

(ii) a compound of formula 26,

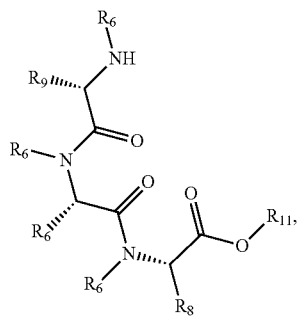

and (iii) a coupling reagent (preferably, BOP, BEP, PyAOP, or DEPBT) to afford a compound of formula 27a or formula 27b;

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group.

In another aspect, the invention provides a process to prepare a compound of formula 16 or formula 17:

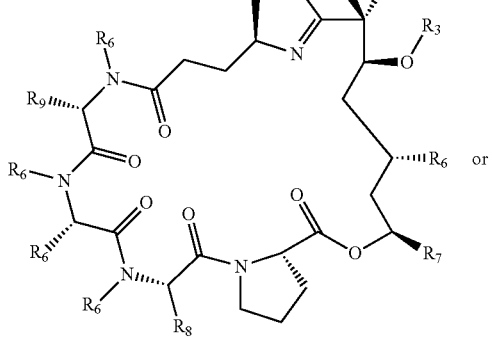

(16)

(17)

comprising reacting (i) a compound of formula 28a,

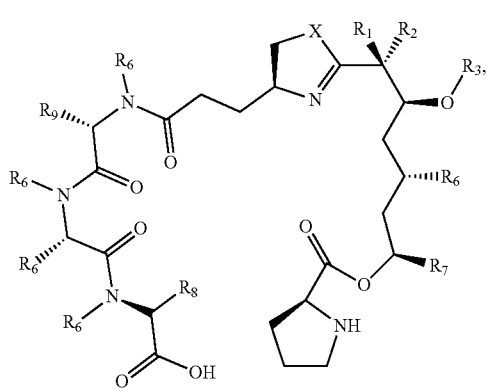

or formula 28b,

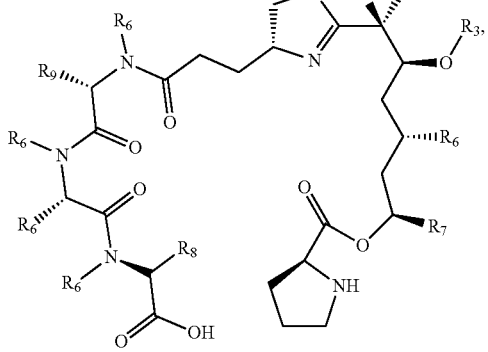

and (ii) a coupling reagent (preferably, BOP, BEP, PyAOP, or DEPBT) to afford a compound of formula 16 or formula 17;

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group.

In another aspect, the invention provides a process to prepare a compound of formula 16 or formula 17:

(16)

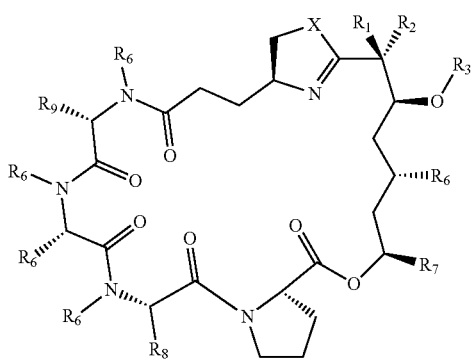

or

-continued (17)

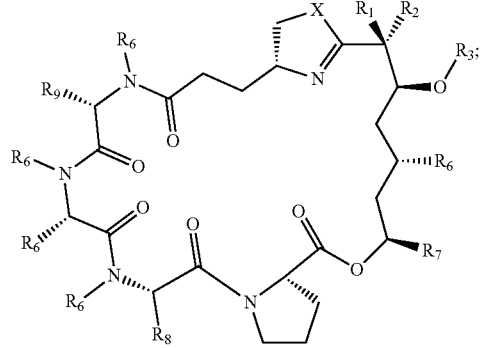

comprising:

a) reacting (i) a compound of formula 26a,

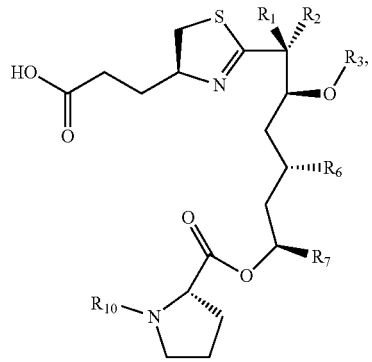

or formula 26b,

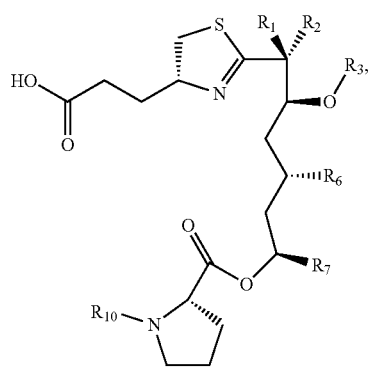

(ii) a compound of formula 26,
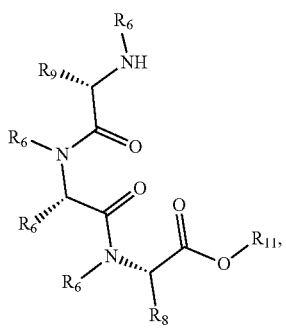
and (iii) a coupling reagent (preferably, BOP, BEP, PyAOP, or DEPBT) to afford a compound of formula 27a,
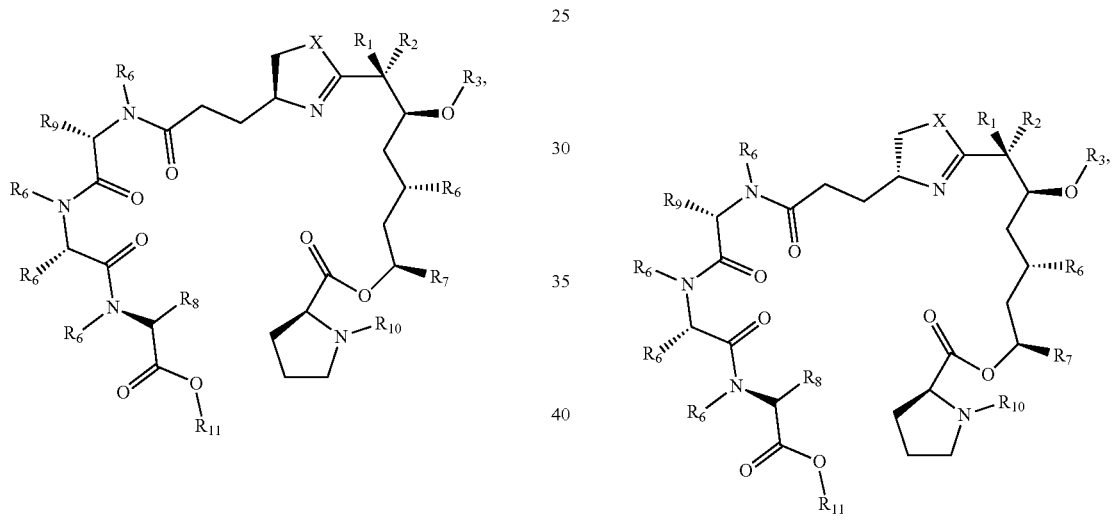
or formula 27b,
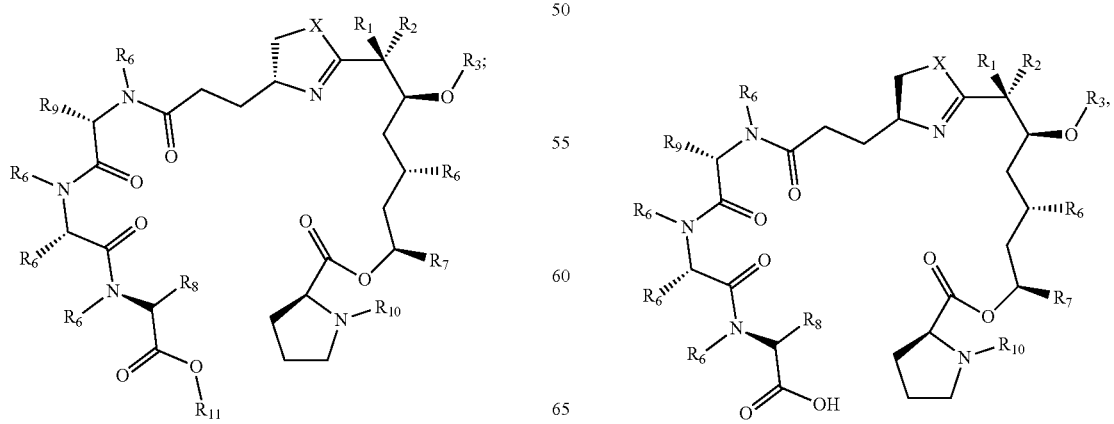
b) deprotecting carboxylic acid protecting group, $R_{11}$, from a compound of formula 27a,
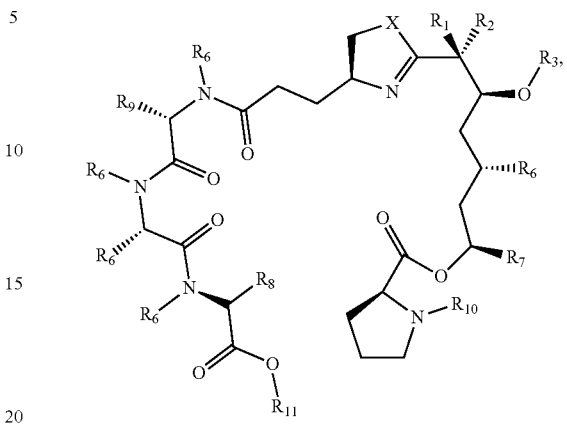
or formula 27b,
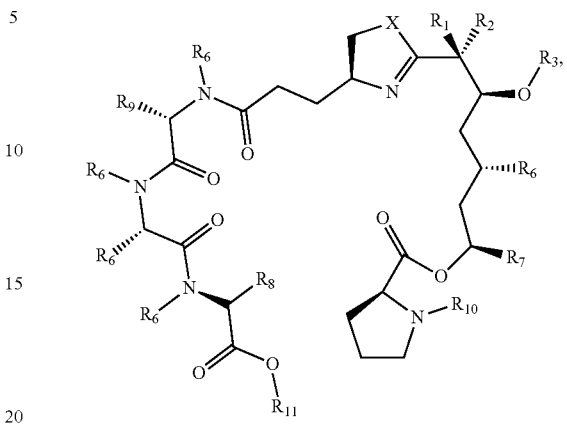
to afford a compound of formula 29a, or formula 29b,
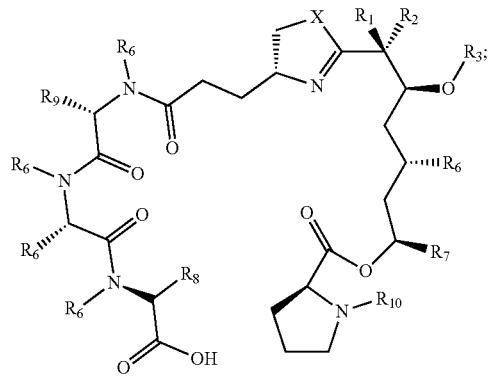
c) deprotecting amino protecting group, R$_{10}$, from a compound of formula 29a,
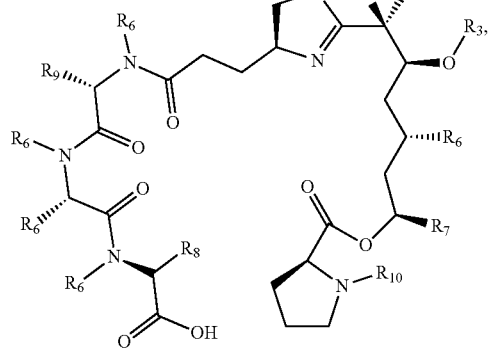
or formula 29b,
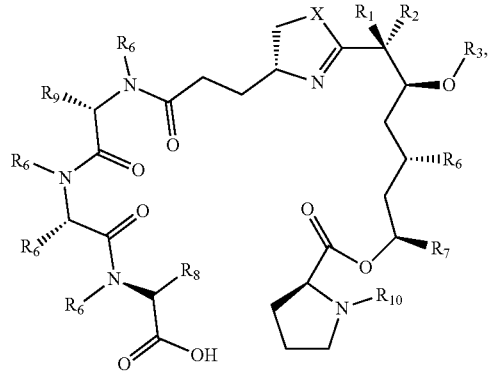
to afford a compound of formula 30a,
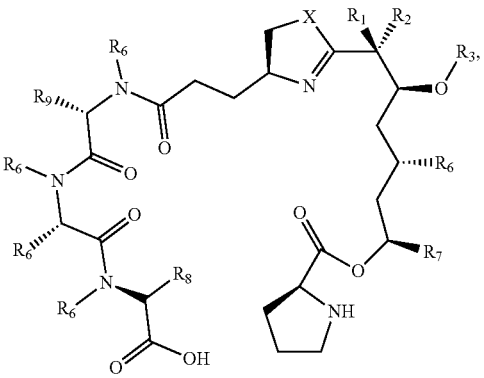
or formula 30b,
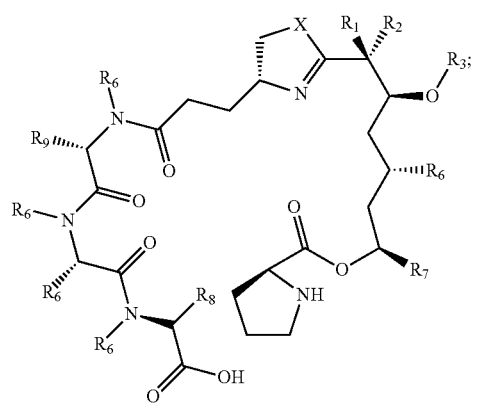
and
d) coupling the amino- and carboxylic acid moieties from a compound of formula 30a,
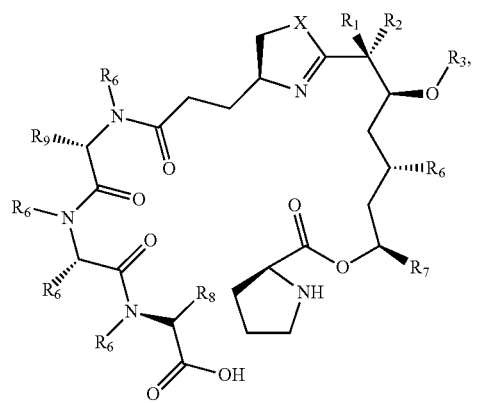

or formula 30b, (30b)

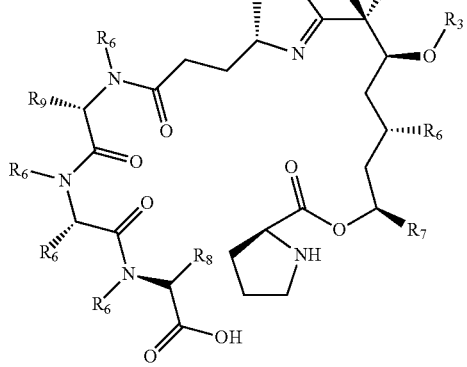

or formula 26b, (17)

comprising:

a) reacting (i) a compound of formula 26a, (26a)

using a coupling reagent (preferably, BOP, BEP, PyAOP, or DEPBT) to afford a compound of formula 16 or formula 17;

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group. In a further embodiment, the coupling agent in at least one of steps a) or d) is selected from the group consisting of BOP, BEP, PyAOP, and DEPBT.

In another aspect, the invention provides a process to prepare a compound of formula 16 or formula 17:

(16)

(26b)

(ii) a compound of formula 26,
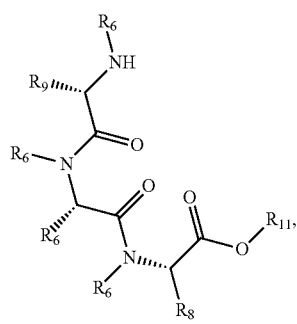
and (iii) a coupling reagent (preferably, BOP, BEP, PyAOP, or DEPBT) to afford a compound of formula 27a,
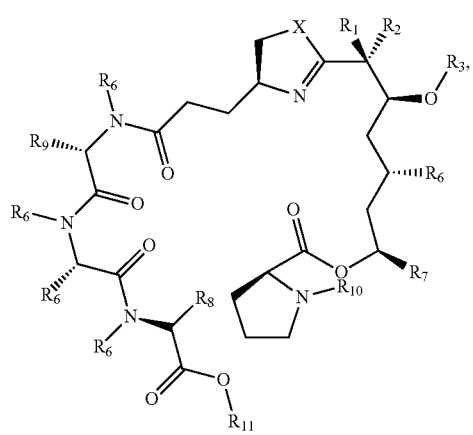
or formula 27b,
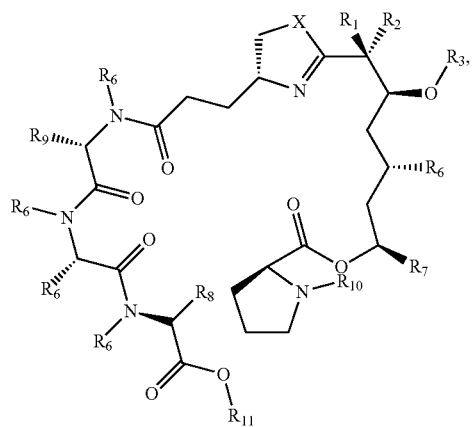
b) deprotecting amino protecting group, $R_{10}$, from a compound of formula 27a,
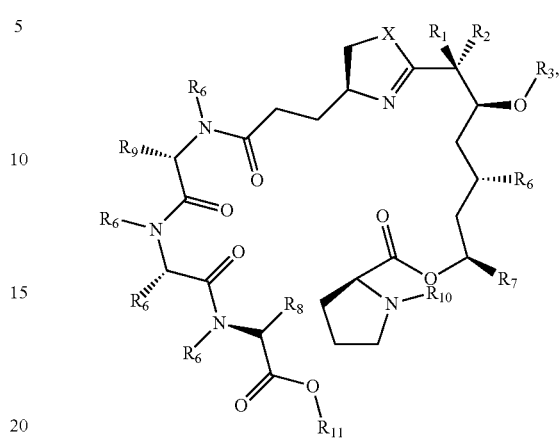
or formula 27b,
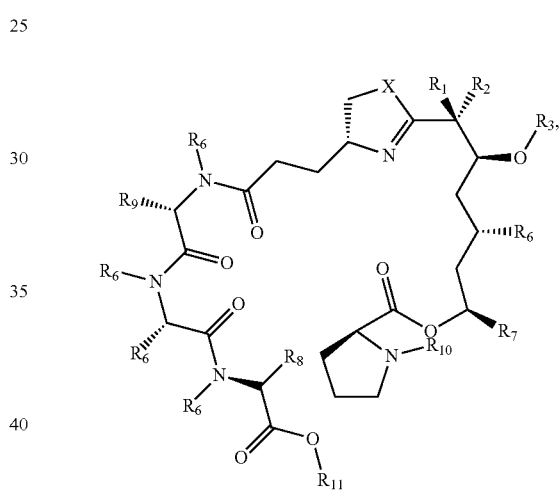
to afford a compound of formula 31a,
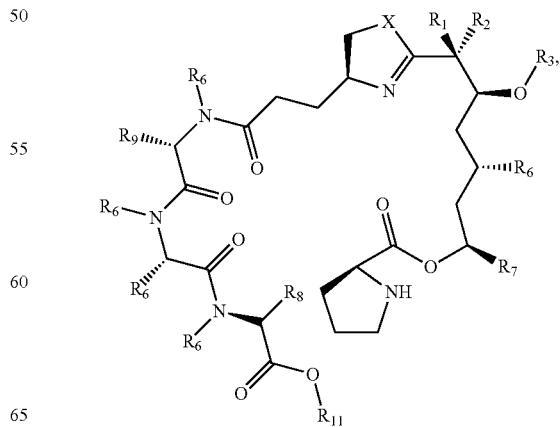

or formula 31b,
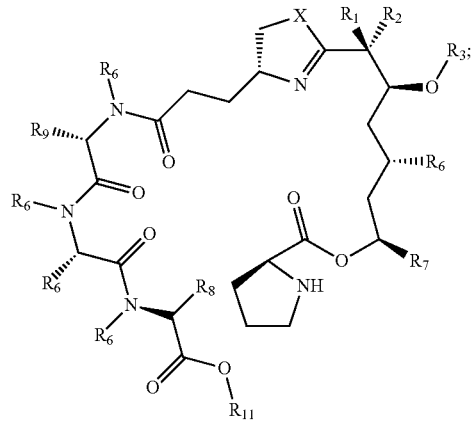
c) deprotecting carboxylic acid protecting group, $R_{11}$, from a compound of formula 31a,
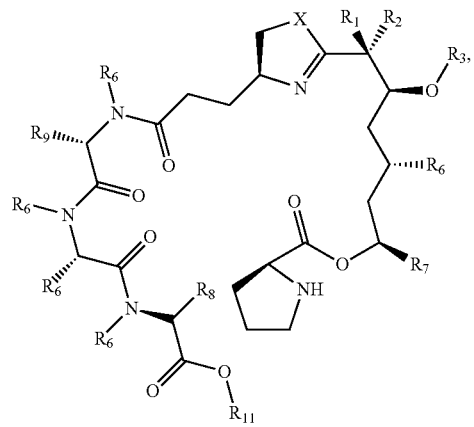
or formula 31b,
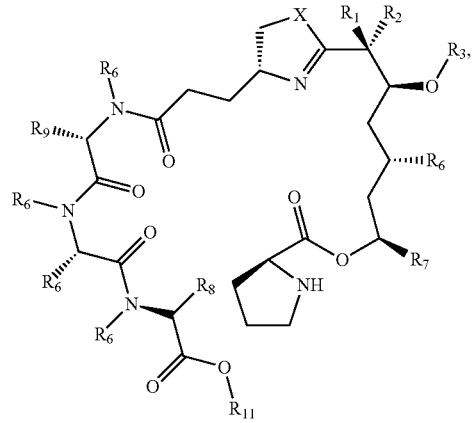
to afford a compound of formula 30a,
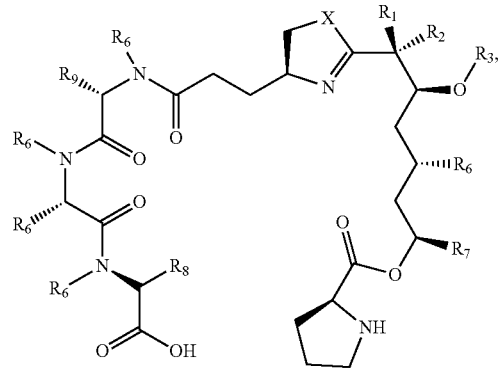
or formula 30b,
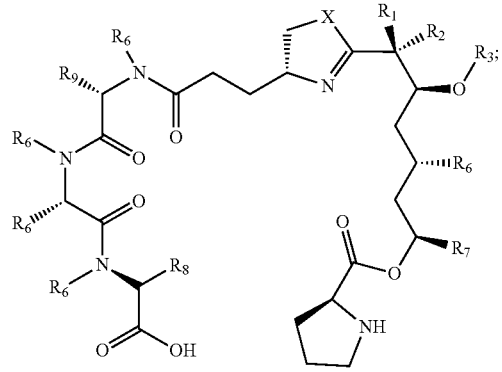
and
d) coupling the amino- and carboxylic acid moieties from a compound of formula 30a,
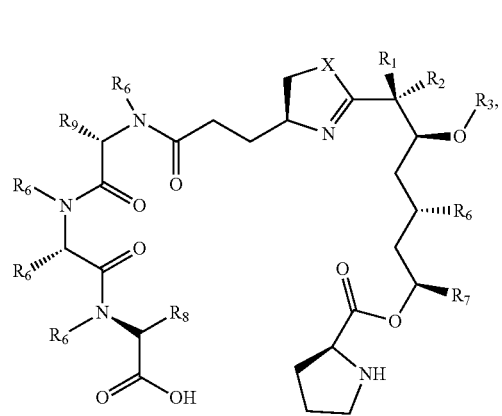

or formula 30b,

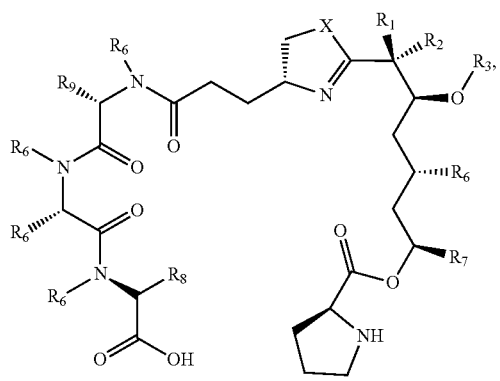

using a coupling reagent (preferably, BOP, BEP, PyAOP, or DEPBT) to afford a compound of formula 16 or formula 17;

wherein each X is S;

each $R_1$ and $R_2$ is independently H or optionally substituted alkyl;

each $R_3$ is independently H, optionally substituted alkyl, or —C(O)alkyl;

each $R_6$ is independently H, optionally substituted alkyl, or —C(O)alkyl;

each $R_7$ and $R_8$ is independently H or optionally substituted alkyl;

each $R_9$ is independently H, optionally substituted alkyl, or optionally substituted aralkyl;

each $R_{10}$ is independently an amino protecting group; and each $R_{11}$ is a carboxylic acid protecting group. In a further embodiment, the coupling agent in at least one of steps a) or d) is selected from the group consisting of BOP, BEP, PyAOP, and DEPBT.

In another aspect, the compound from any of the processes presented herein is a compound of formula 32a or 32b:

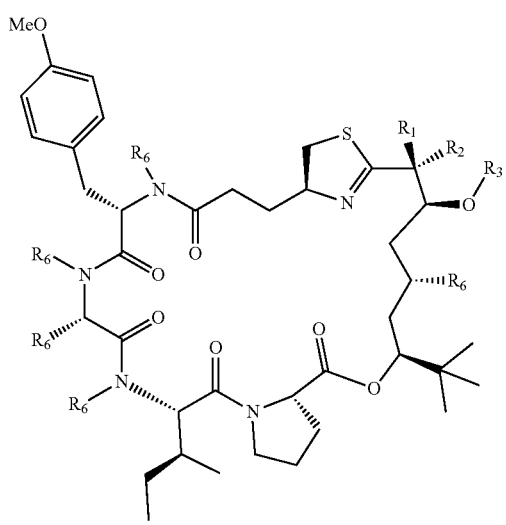

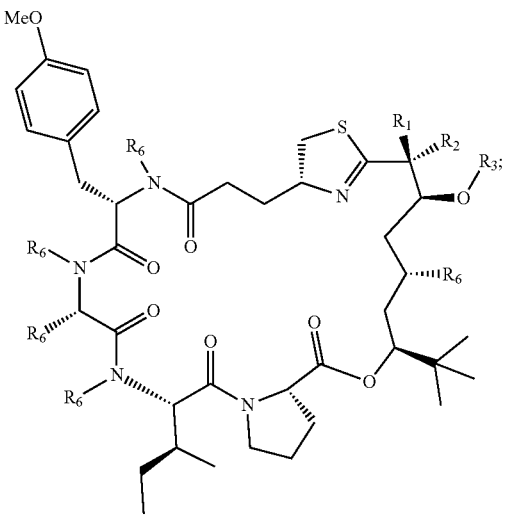

wherein each $R_1$ and $R_2$ is H or optionally substituted alkyl;

each $R_3$ is independently H, optionally substituted alkyl, or —C(O)alkyl; and each $R_6$ is independently H, optionally substituted alkyl, or —C(O)alkyl.

In another aspect, the compound from any of the processes presented herein is a compound selected from the following:

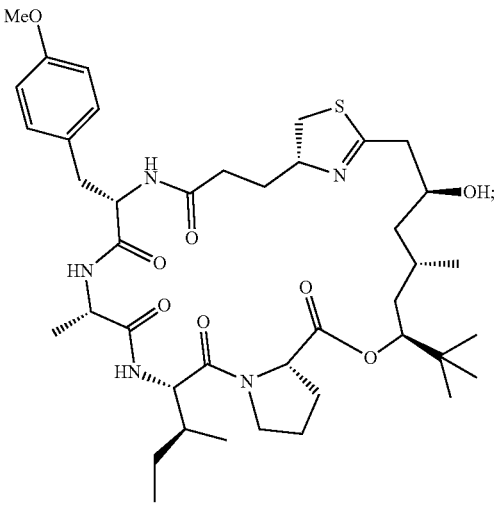

47
-continued
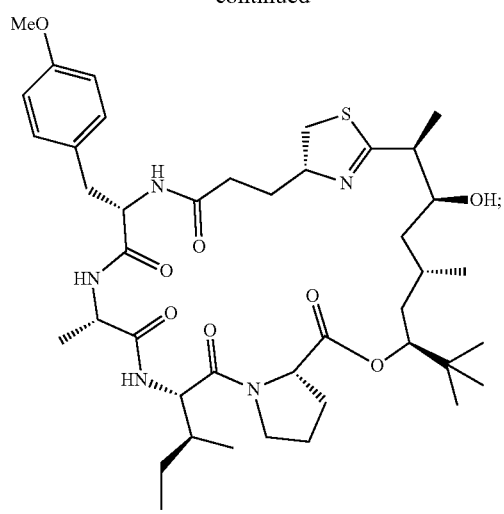
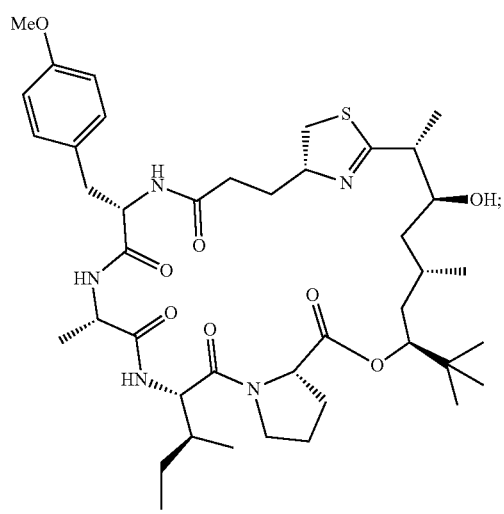
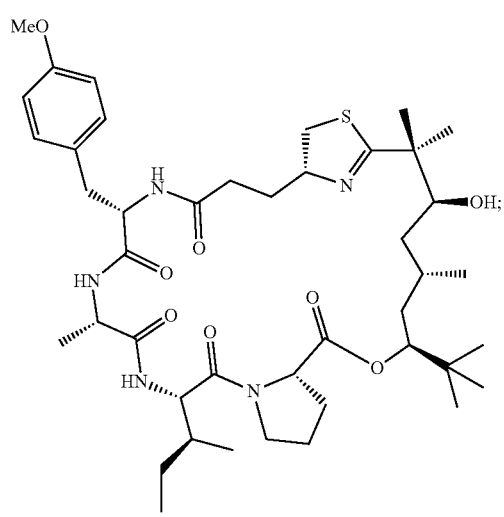
48
-continued
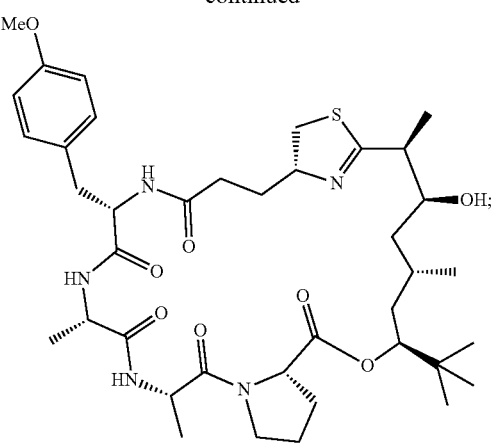
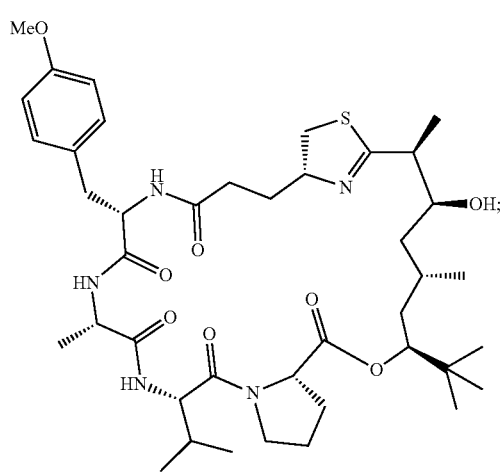
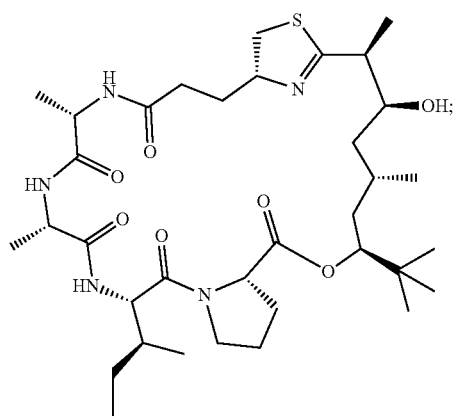

49
-continued
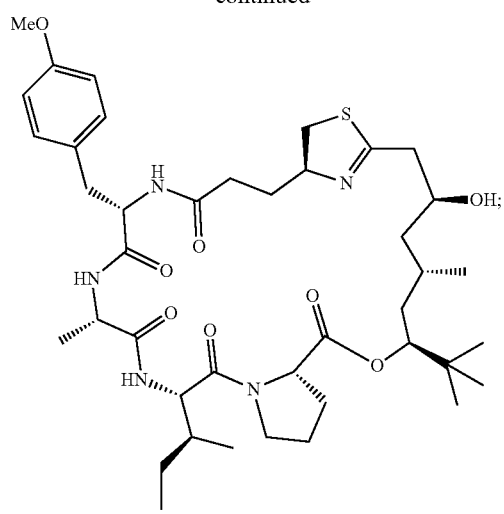
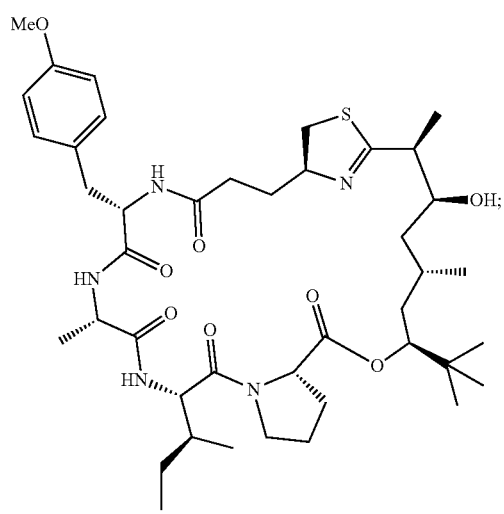
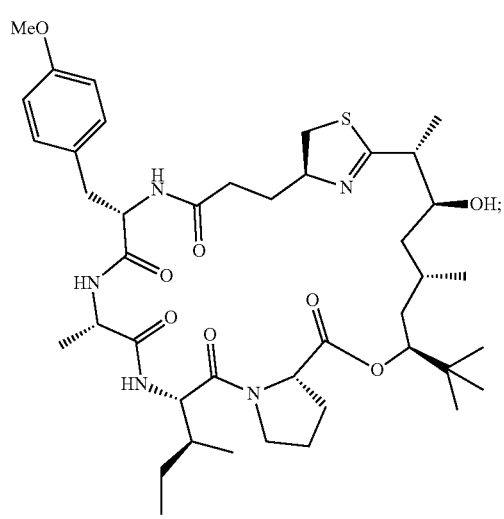
50
-continued
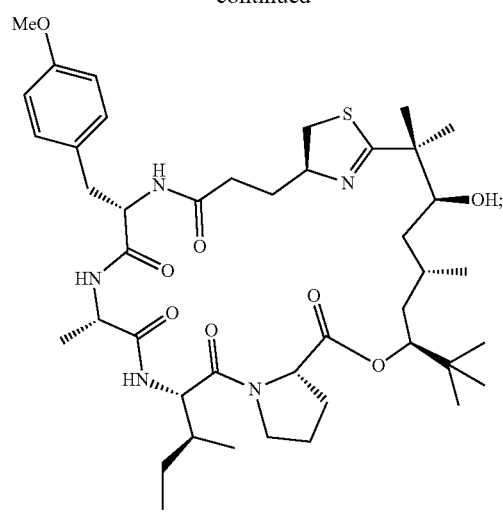
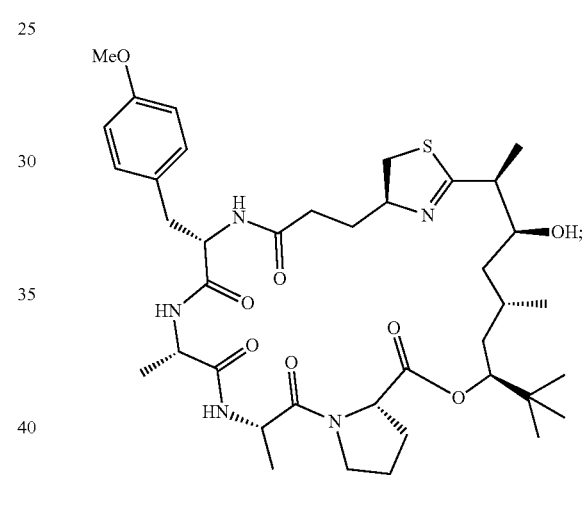
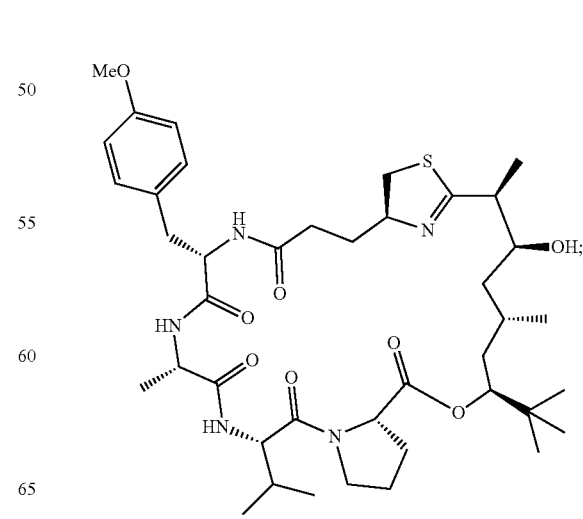

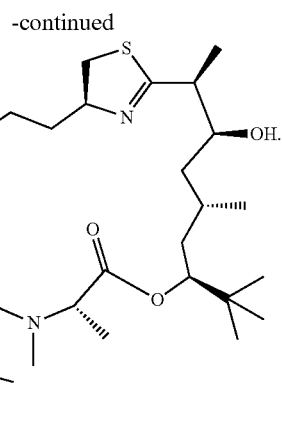

In another aspect, the Lewis acid from any of the processes presented herein is selected from the group consisting of TiCl$_4$, Ti(OiPr)$_4$, AlCl$_3$, BF$_3$, BCl$_3$, SnCl$_4$ (preferably TiCl$_4$).

In one aspect, the invention provides a method of treating a disease, disorder, or symptom thereof in a subject, comprising administering to said subject a compound of any of the formulae herein.

In another aspect, the invention provides a method of treating a subject suffering from or susceptible to a STAT3 activity and/or T-cell activation related disorder or disease, wherein the subject has been identified as in need of treatment for a STAT3 activity and/or T-cell activation related disorder or disease, comprising administering to said subject in need thereof, an effective amount of a compound or pharmaceutical composition any of the formulae herein, such that said subject is treated for said disease or disorder. In aspects, the disease or disorder is one wherein receptor downregulation may be beneficial, e.g., autoimmune diseases, some which may be associated with chemokine receptors (e.g., multiple sclerosis), or inflammation.

In another aspect, the invention provides a method of treating a subject suffering from or susceptible to a disorder or disease wherein inhibition of cotranslational translocation within the secretory pathway leads to downregulation of receptors, other membrane proteins, or secreted proteins. In one aspect the method is that wherein a subject has been identified as in need of treatment for a disorder or disease wherein inhibition of cotranslational translocation within the secretory pathway leads to downregulation of receptors, other membrane proteins, or secreted proteins, comprising administering to said subject in need thereof, an effective amount of a compound or pharmaceutical composition of any of the formulae herein, such that said subject is treated for said disease or disorder. In other aspects, the method comprises treatment of a subject having a disease identified as one wherein downregulation of a receptor (or other membrane proteins, or secreted proteins) and/or inhibition of growth factor/cytokine secretion is caused by inhibition of cotranslational translocation. In aspects, the disease or disorder is one wherein receptor tyrosine kinase (RTK) receptor downregulation may be beneficial, e.g., cancer, autoimmune diseases, some which may be associated with chemokine receptors (e.g., multiple sclerosis), or inflammation. In one aspect, the downregulated target is any growth factor or cytokine (e.g., FGF1-4, VEGF, IL-6) or FGFR, PDGFR, IGFR, VEGFR and other receptors (e.g., FGFR1-4, or VEGFR2). In another aspect the disease or disorder is one modulated by any growth factor, FGF, VEGF or other receptor (e.g., FGF1-4, FGFR2 or VEGFR2) or cytokine whose secretion is inhibited by the described compounds.

In one aspect the methods herein are those wherein inhibition of growth factor/cytokine secretion is caused by the compounds of any of the formulae herein. In another aspect the methods herein are those wherein both downregulation of a receptor (e.g., any cited herein) and inhibition of growth factor/cytokine secretion is caused by the compounds of any of the formulae herein.

In one aspect the methods herein are those wherein the compounds of any of the formulae herein inhibit a receptor (e.g., any cited herein; growth factor, cytokine, an RTK, etc.). In one aspect the methods herein are those wherein the compounds of any of the formulae herein inhibit a ligand of a receptor (e.g., any cited herein; growth factor, cytokine, an RTK, etc.). In one aspect the methods herein are those wherein the compounds of any of the formulae herein inhibit a receptor (e.g., any cited herein; growth factor, cytokine, an RTK, etc.) and inhibit a ligand of a receptor (e.g., any cited herein; growth factor, cytokine, an RTK, etc.). In one aspect the methods herein are those wherein the compounds of any of the formulae herein inhibit a receptor (e.g., any cited herein; growth factor, cytokine, an RTK, etc.) and/or inhibit a ligand of that receptor (e.g., any cited herein; growth factor, cytokine, an RTK, etc.).

In another aspect, inhibition of cotranslational translocation using the compounds herein results in the downregulation of certain ER proteins such as CANX, TXNDC5, PDI, CALR, BIP, or RPN1.

In another aspect, the disease or disorder is Hashimoto's thyroiditis, Pernicious anemia, Addison's disease, Type I diabetes, Rheumatoid arthritis, Systemic lupus erythematosus, Dermatomyositis, Sjogren syndrome, Lupus erythematosus, Multiple sclerosis, Myasthenia gravis, Reactive arthritis, Grave's disease, or Celiac disease—sprue. In another aspect, the disease or disorder is cystic fibrosis.

In other aspects, the invention provides a method of modulating the proliferation activity in a subject, comprising contacting the subject with a compound of any of the formulae herein, in an amount and under conditions sufficient to modulate proliferation activity.

In one aspect, the invention provides a method of treating a subject suffering from or susceptible to a proliferation related disorder or disease, comprising administering to the subject an effective amount of a compound or pharmaceutical composition any of the formulae herein.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of any of the formulae herein, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein, such that cell proliferation in said subject is modulated (e.g., down regulated). In another aspect, the compounds delineated herein preferentially target cancer cells over nontransformed cells.

In another aspect, the invention provides a method of treating a subject suffering from or susceptible to a disorder or disease, wherein the subject has been identified as in need of treatment for a disorder or disease, comprising administering to said subject in need thereof, an effective amount of a compound or pharmaceutical composition thereof wherein the compound inhibits a target (e.g., any cited herein; growth factor, cytokine, an RTK, etc.) and/or inhibits a ligand of that target (e.g., any cited herein; growth factor, cytokine, an RTK, etc.). In one aspect, the compound is any of the formulae herein, or composition thereof.

Another aspect is a kit comprising an effective amount of any the formulae herein identified as an inhibitor of cotranslational translocation of proteins destined for the secretory pathway, in unit dosage form, together with instructions for administering the compound to a subject suffering from or susceptible to a cell proliferation disorder.

Another aspect is a method of modulating the activity of cell proliferation in a subject, comprising identifying a subject in need of inhibition of cotranslational translocation of proteins destined for the secretory pathway with a compound identified as an inhibitor of cotranslational translocation of proteins destined for the secretory pathway, and administering to said subject in need thereof, an effective amount of a compound or pharmaceutical composition of any of the formulae herein, in an amount and under conditions sufficient to modulate cell proliferation. In aspects, the inhibition of cotranslational translocation of proteins destined for the secretory pathway can be through modulation of other targets, or can additionally affect targets in the endoplasmic reticulum (e.g., ER proteins, including those delineated herein).

Another aspect is a method of treating a subject suffering from or susceptible to a cell proliferation related disorder or disease (e.g., cancer), wherein the subject has been identified as in need of treatment for a cell proliferation related disorder or disease by downregulation of a receptor tyrosine kinase, comprising administering to said subject in need thereof, an effective amount of a compound of any of the formulae herein, such that said subject is treated for said disorder.

Another aspect is a method of treating a subject suffering from or susceptible to a disorder or disease wherein growth factor and cytokine (ligand) downregulation is beneficial, particularly diseases including cancers that are driven by autocrine loops (e.g., colon cancer), wherein the subject has been identified as in need of treatment for a such disorder or disease, comprising administering to said subject in need thereof, an effective amount of a compound herein (or composition thereof), such that said subject is treated for said disorder.

In a specific aspect, the invention provides a method of treating cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), comprising administering to said subject in need thereof, an effective amount of a compound delineated herein (e.g., any of the formulae herein), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other cancers that may be treated using the methods herein include, cervical, ovarian, bladder, pancreatic, colon, and brain.

BRIEF DESCRIPTION OF THE DRAWINGS

The present invention is further described below with reference to the following non-limiting examples and with reference to the following figures, in which.

Figure 1:
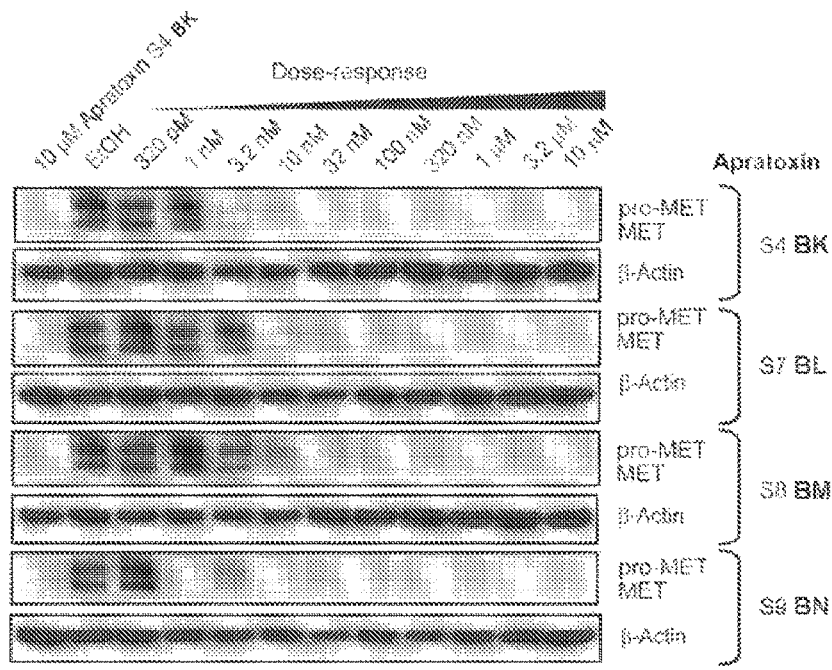
FIG. 1. depicts the SAR for synthetic apratoxins, BK, BL, BM, and BN by immunoblot analysis for RTK (MET) levels.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

The term "carboxylic acid protecting group," as used herein, refers to a labile chemical moiety which is known in the art to protect a carboxylic acid group against undesired reactions during synthetic procedures. After said synthetic procedure(s) the carboxylic acid protecting group as described herein may be selectively removed. Carboxylic acid protecting groups as known in the are described generally in T. H. Greene and P. G. M. Wuts, Protective Groups in Organic Synthesis, 3rd edition, John Wiley & Sons, New York (1999). Non-limiting examples of carboxylic acid protecting groups include methyl ester, heptyl ester, 9-fluorenylmethyl ester, methoxymethyl ester, methylthiomethyl ester, tetrahydropyranyl ester, tetrahydrofuranyl ester, methoxyethoxymethyl ester, 2-(trimethylsilyl)ethoxymethyl ester, benzyloxymethyl ester, pivaloyloxymethyl ester, phenylacetoxymethyl ester, triisopropylsilylmethyl ester, cyanomethyl ester, acetol ester, phenacyl ester, p-bromophenacyl ester, p-methoxyphenacyl ester, desyl ester, carboxamidomethyl ester, p-azobenzenecarboxamidomethyl ester, N-phthalimidomethyl ester, 2,2,2-trichloroethyl ester, 2-haloethyl ester, 2-(trimethylsilyl)ethyl ester, 2-methylthioethyl ester, 1,3-dithianyl-2-methyl ester, 2-(p-nitrophenylsulfenyl)ethyl ester, 2-(2'-pyridyl)ethyl ester, 2-(p-methoxyphenyl)ethyl ester, 2-(diphenylphosphino)ethyl ester, 1-methyl-1-phenethyl ester, 2-cyanoethyl ester, 3-methyl-3-pentyl ester, dicyclopropylmethyl ester, 2,4-dimethyl-3-pentyl ester, tert-butyl ester, phenyl ester, 2,6-dialkylphenyl esters, p-(methylthio)phenyl ester, pentafluorophenyl ester, benzyl ester, diphenylmethyl ester, bis(o-nitrophenyl)methyl ester, 9-anthrylmethyl ester, 2-(9,10-dioxo)anthrylmethyl ester, 5-dibenzosuberyl ester, 2-(trifluoromethyl)-6-chromonylmethyl ester, 2,4,6-trimethylbenzyl ester, triphenylmethyl ester, p-methoxybenzyl ester, 2,6,-dimethoxybenzyl ester, 4-(methylsulfinyl)benzyl ester, 4-sulfobenzyl ester, 4-azidomethoxybenzyl ester, piperonyl ester, 4-picolyl ester, p-bromobenzyl ester, o-nitrobenzyl ester, p-nitrobenzyl ester, trimethylsilyl ester, triethylsilyl ester, t-butyldimethylsilyl ester, i-propyldimethylsilyl ester, phenyldimethylsilyl ester, di-t-butylmethylsilyl ester, triisopropylsilyl ester, allyl ester, methallyl ester, 2-methylbut-3-en-2-yl ester, 3-methylbut-3-en-2-yl ester, 4-(trimethylsilyl)-2-buten-1-yl ester, cinnamyl ester, alpha-methylcinnamyl ester, propargyl ester, cyclopentyl ester, cyclohexyl ester, and the like.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, methyl carbamate, ethyl carbamate, 9-fluorenylmethyl carbamate, 2,2,2-trichloroethyl carbamate, 2-trimethylsilylethyl carbamate, 2-phenylethyl carbamate, 1-(1-adamanthyl)-1-methylethyl carbamate, 2-chloroethyl carbamate, 1,1-dimethyl-2-haloethyl carbamate, 2-(2'-pyridyl)ethyl carbamate, 2-(4'-pyridyl)ethyl carbamate, 1-adamanthyl carbamate, 2-adamanthyl carbamate, vinyl carbamate, allyl carbamate, cinnamyl carbamate, 3-(3'-pyridyl)prop-2-enyl carbamate, N-hydroxypiperidinyl carbamate, alkyldithio carbamate, benzyl carbamate, p-methoxybenzyl carbamate, p-nitrobenzyl carbamate, 4-methylsulfinylbenzyl carbamate, diphenylmethyl carbamate, 2-methylthioethyl carbamate, 2-methylsulfonylethyl carbamate, 2-(4-nitrophenyl)ethyl carbamate, 3',5'-dimethoxybenzoin carbamate, acetamide, chloroacetamide, trifluoroacetamide, phenylacetamide, 3-phenylpropanamide, pent-4-enamide, 3-pyridylcarboxamide, benzamide, p-phenylbenzamide, N-phthalimide, N-tetrachlorophthalimide, 4-nitro-N-phthalimide, N-dithiasuccinimide, N-t-butylamine, N-allylamine, N-benzylamine, N-4-methoxybenzylamine, N-2,4-dimethoxybenzylamine, N-(diphenylmethyl)amine, N-5-dibenzosuberylamine, N-triphenylmethylamine, N-9-phenylfluorenylamine, N-1,1-dimethylthiomethyleneamine, N-benzylideneamine, benzenesulfonamide, p-toluenesulfonamide, 2- or 4-nitrobenzenesulfonamide, 2,4-dinitrobenzenesulfonamide, trifluoromethylsulfonamide, phenacylsulfonamide, N,N-dimethylsulfonamide, mesitylenesulfonamide, p-methoxyphenylsulfonamide, t-butoxycarbonyl, 9-fluorenylmethoxycarbonyl, benzyloxycarbonyl, and the like.

The term "thiol protecting group," as used herein, refers to a labile chemical moiety which is known in the art to protect a thiol group against undesired reactions during synthetic procedures. After said synthetic procedure(s) the amino protecting group as described herein may be selectively removed. Thiol protecting groups as known in the are described generally in T. H. Greene and P. G. M. Wuts, Protective Groups in Organic Synthesis, 3rd edition, John Wiley & Sons, New York (1999). Examples of thiol protecting groups include, but are not limited to, alkyl, benzyl, p-methoxybenzyl, p-nitrobenzyl, 2,4,6-trimethylbenzyl, 2,4,6-trimethoxybenzyl, diphenylmethyl, bis(4-methoxyphenyl)phenylmethyl, diphenyl-4-pyridyl, 2,4-dinitrophenyl, trifluoroacetyl, 9-fluorenylmethyl, t-butyl, triphenylmethyl, phenyl, methoxymethyl, benzyloxymethyl, alkylcarbonyl, benzoyl, trifluoroacetyl, t-butoxycarbonyl, 2,2,2-trichloroethoxycarbonyl, benzyloxycarbonyl, alkylaminocarbonyl, and the like.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(OXOEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

LIST OF ABBREVIATIONS

In order that the invention may be more readily understood, certain abbreviations are first defined here for convenience.

BEP: 2-bromo-1-ethyl-pyridinium tetrafluoroborate
Boc: tert-butoxycarbonyl
BOP: (benzotriazol-1-yloxy)tris(dimethylamino)phosphonium hexafluorophosphate
BRSM: based on recovered starting material
Cys: cysteine
DEPBT: 3-(diethoxyphosphoryloxy)-1,2,3-benzotriazin-4(3H)-one
DIBAL-H: diisobutylaluminum hydride
DMAP: 4-(dimethylamino)pyridine
EDCI: N-(3-dimethylaminopropyl)-N'-ethylcarbodiimide hydrochloride
GSH: Glutathione
HATU: 1-[bis(dimethylamino)methylene]-1H-1,2,3-triazolo[4,5-b]pyridinium 3-oxid hexafluorophosphate
LiAlH$_4$: lithium aluminum hydride
moCys: modified cysteine
NAC: N-acetyl-L-cysteine
PMB: 4-methoxybenzyl
PyAOP: (7-azabenzotriazol-1-yloxy)tripyrrolidinophosphonium hexafluorophosphate
RCM: ring closing metathesis
TBAF: tetrabutylammonium fluoride
TBAI: tetrabutylammonium iodide
TBS: tert-butyldimethylsilyl
TfOH: trifluoromethanesulfonic acid
Troc: 2,2,2-trichloroethoxycarbonyl
TMSOTf: trimethylsilyl trifluoromethanesulfonate Compounds of the Invention Compounds delineated herein include salt, hydrate and solvates thereof. They include all compounds delineated in schemes herein, whether intermediate or final compounds in a process.

Compounds of the invention can be obtained from natural sources or made or modified made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database. For example, compounds of formulae herein can be made using methodology known in the art, including Doi et al., Org Lett. 2006 Feb. 2; 8(3):531-4; Ma, et al., Chemistry. 2006 Oct. 10; 12(29):7615-26; and Chen et al., Proc Natl Acad Sci USA. 2004 Aug. 17; 101(33):12067-72.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. All hydrate and solvate forms of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

The compounds of the formulae herein can be synthesized using methodology similar to that shown in the following schemes.

Scheme I illustrates the synthesis of aldehyde K starting from pivalaldehyde. β-Hydroxy ketone A was prepared via the D-proline catalyzed aldol reaction of pivalaldehyde with acetone. After protection of A as the TBS ether to afford B, reduction with NaBH$_4$ to C, elimination via the corresponding mesylate, C was transformed into allyl TBS ether D. The cleavage of the TBS moiety from D afforded allyl alcohol E, which is the most critical step in the preparation of K due to its volatile property [Kinnaird, J. W. A.; Ng, P. Y.; Kubota, K.; Wang, X.; Leighton, J. L. *J. Am. Chem. Soc.* 2002, 124, 7920-7921]. The solvent (Et$_2$O and THF) in E-containing fractions can be removed by distillation using a Vigreux fractionation column for small scale reaction under normal pressure; however, for large-scale reactions, this was not feasible and, thus, we used the combination of a cooling-concentration method under ambient reduced pressure and Vigreux fraction concentration.

Aldehyde K was prepared starting from allyl alcohol E through formation of acryloyl ester F, Grubbs' catalyst-effected RCM reaction (G), methylation with Me$_2$(CuCN)Li$_2$(H), Weinreb amide formation (I), protection of hydroxy group with PMB (J) and reduction with DIBAL-H (K). The yield was low (10-25%) when we used p-methoxybenzyl bromide (PMBBr) to protect the hydroxy group of I in the presence of NaH/tetra-n-butyl-ammonium iodide (TBAI) in THF or NaH in DMF. Fortunately, we found that the PMBOC(NH)CCl$_3$/TfOH method was effective in smoothly converting I into PMB ether J in moderate yield (56%) [Doi, T.; Numajiri, Y.; Munakata, A.; Takahashi, T. *Org. Lett.* 2006, 8, 531-534]. Furthermore, unreacted starting material I was recovered quantitatively and could be used in the next cycle.

Scheme I

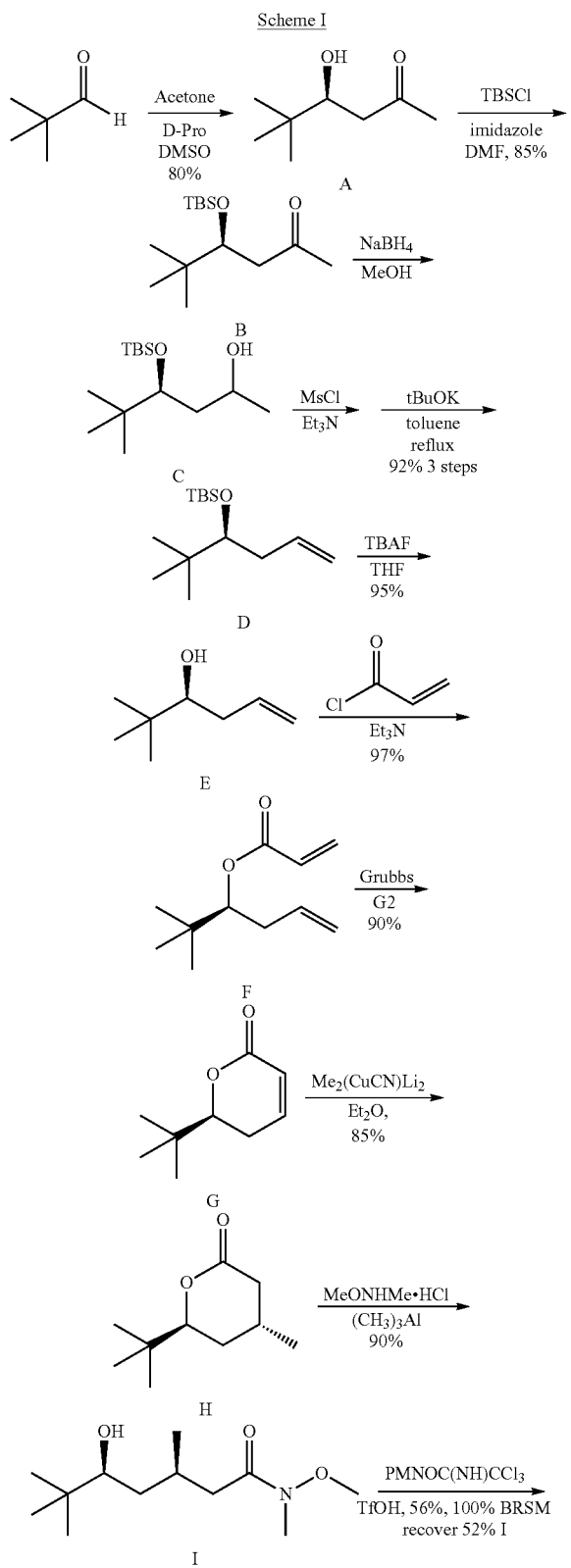

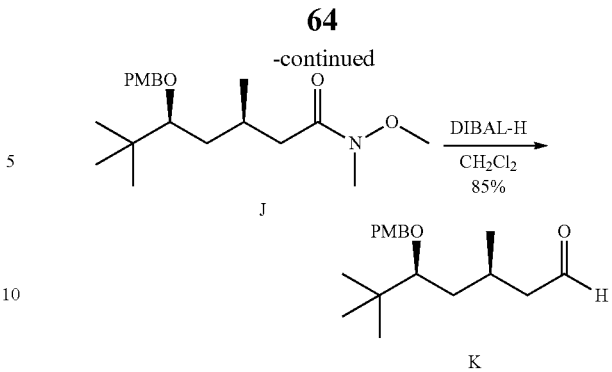

With aldehyde K in hand, aliphatic acids T, U, and AB were prepared as outlined in Scheme 2. Previous syntheses constructed the C34(Me)-C35(OH) chiral unit of N through Roush's crotylation with Roush's (E)-crotylborate at −78° C. in toluene following published procedures [Chen, Q.-Y.; Liu, Y.; Luesch, H. *ACS Med. Chem. Lett.* 2011, 2, 861-865; Numajiri, Y.; Takahashi, T.; Doi, T. *Chem. Asian J.* 2009, 4, 111-125; Roush, W. R.; Ando, K.; Powers, D. B.; Palkowitz, A. D.; Halterman, R. L. *J. Am. Chem. Soc.* 1990, 112, 6339-6348]. However, Roush's (E)-crotylborate is not commercially available, it is laborious to purify crude Roush's (E)-crotylborate prepared in the lab by distillation and, if the crude product was used without purification, the impurity reduced the yield to as low as 55%. However, Scheme 2 employs Leighton's silanes, L and M, instead of Roush's crotylborate to construct the C34-C35 units in N and O. Leighton's silanes, L and M, are commercially available and inexpensive; they are solid and easy to handle [Kim, H.; Ho, S.; Leighton, J. L. *J. Am. Chem. Soc.* 2011, 133, 6517-6520; Harrison, T. J. *J. Am. Chem. Soc.* 2011, 133, 7308-7311]. Chiral alcohols N and O were obtained smoothly at high yields when aldehyde K was treated with L and M along with $Sc(OTf)_3$ in $CH_2Cl_2$ at 0° C., respectively. N was converted into Troc ester P with 2,2,2-trichloroethoxycarbonyl (TrocCl) in the presence of pyridine and DMAP. The Troc ester of O was not stable and partly dehydrated to form a conjugated double bond, which led to low yield and complicated the purification. Therefore, the hydroxy group of O was protected with TBSOTf to smoothly afford the stable TBS ether Q. The removal of the PMB group and subsequent esterification with Fmoc-Pro-OH by the Yamaguchi method provided prolyl esters R and S [Doi, T.; Numajiri, Y.; Munakata, A.; Takahashi, T. *Org. Lett.* 2006, 8, 531-534; Numajiri, Y.; Takahashi, T.; Doi, T. *Chem. Asian J.* 2009, 4, 111-125; Inanaga, J.; Hirata, K.; Saeki, H.; Katsuki, T.; Yamaguchi, M. *Bull. Chem. Soc. Jpn.* 1979, 52, 1989-1993]. The combination of oxidants, $OsO_4$/oxone and $NaIO_4$ was effective to oxidize R to carboxylic acid T; however, when S was exposed to the same conditions, the TBS group was cleaved simultaneously and gave carboxylic acid U with a free hydroxy group. The cleavage of the TBS group may have resulted from the acidic nature of oxone which is a triple salt $2KHSO_5 \cdot KHSO_4 \cdot K_2SO_4$. Both of T and U were obtained in good yields (83% and 80%, respectively).

The enantioselective chiral borane-mediated aldol reaction developed by Kiyooka was used to construct the β-hydroxy-α,α-dimethyl acid part of C34-gem-dimethyl acid AB (Scheme 2b) [Kiyooka, S.-I.; Kaneko, Y.; Komura, M.; Matsuo, H.; Nakano, M. *J. Org. Chem.* 1991, 56, 2276-2278]. Treatment of aldehyde K with methyl trimethylsilyl dimethylketene acetal at −78° C. in the presence of chiral oxazaborolidinone V (derived from D-Val) provided (S)-β-hydroxy ester W. The hydroxyl group of W was protected with the Troc group, however, upon hydrolysis of the methyl ester with LiOH, a complex mixture including Troc-cleaved acid was generated. We therefore hydrolyzed W with LiOH in MeOH—H$_2$O to give β-hydroxy acid X smoothly. Hydroxy acid X was converted into ally ester Y with allyl bromide in the presence of K$_2$CO$_3$ in 93% yield. Hydroxy ester Y was protected with Troc, the PMB group was removed followed by esterification with Fmoc-Pro-OH to provide prolyl ester AA, which was transformed into the carboxylic acid AB by treatment with a Pd$^0$ catalyst and N-methylaniline. The yield for each step was greater than 90%.

Scheme 2 a) Synthesis of T, U

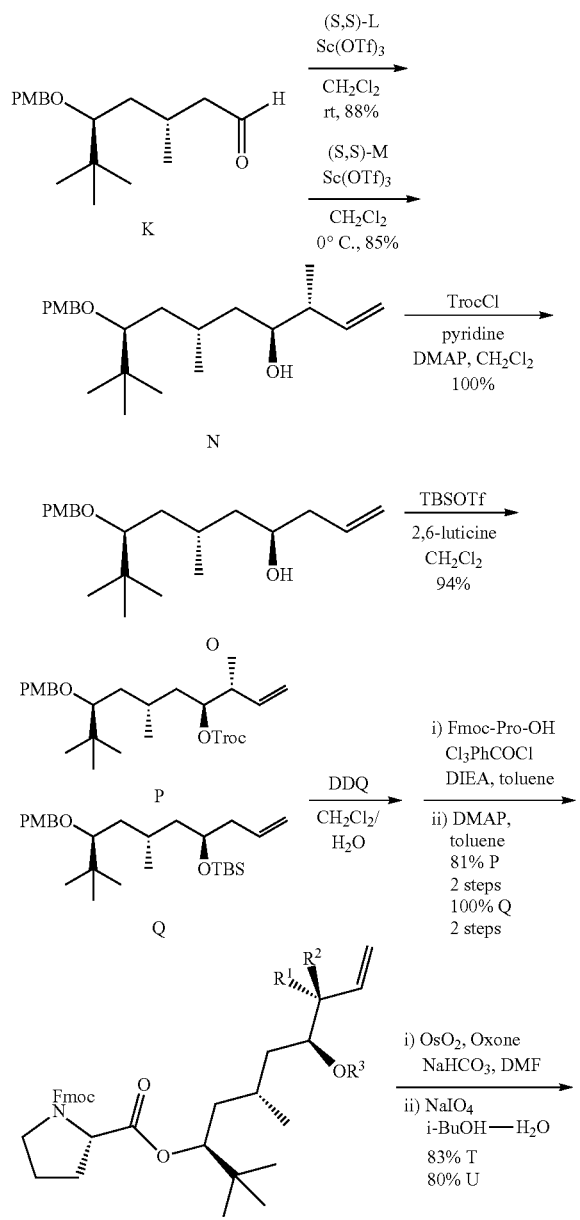

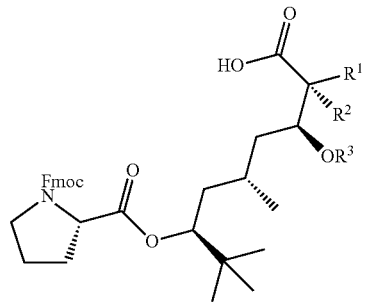

T R$^1$ = CH$_3$, R$^2$ = H, R$^3$ = Troc
U R$^1$ = R$^2$ = R$^3$ = H

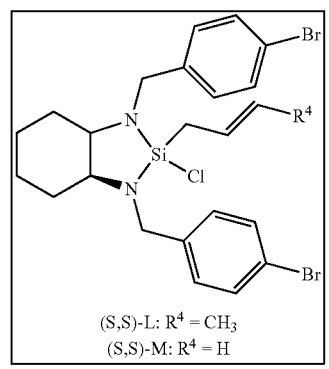

(S,S)-L: R$^4$ = CH$_3$
(S,S)-M: R$^4$ = H b) Synthesis of AB

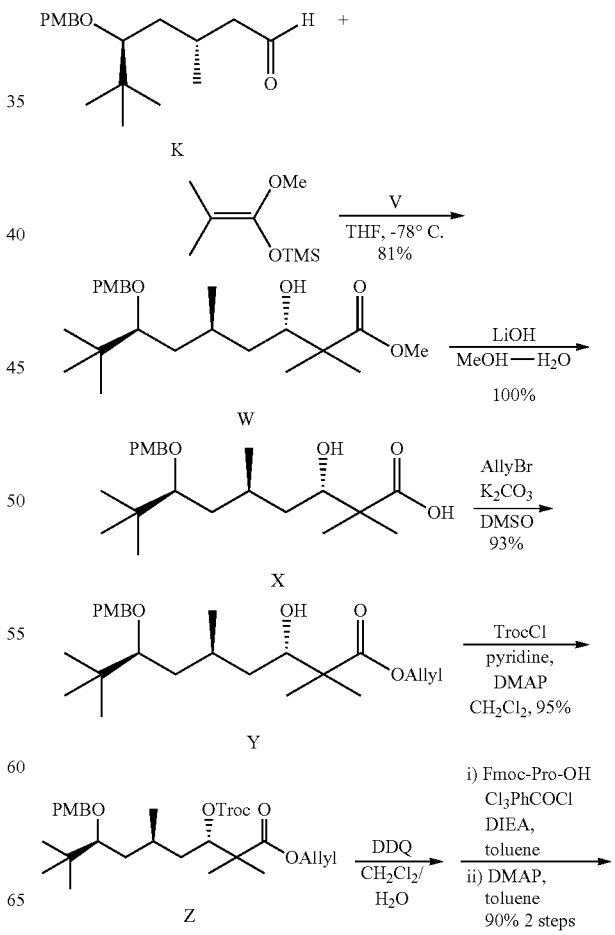

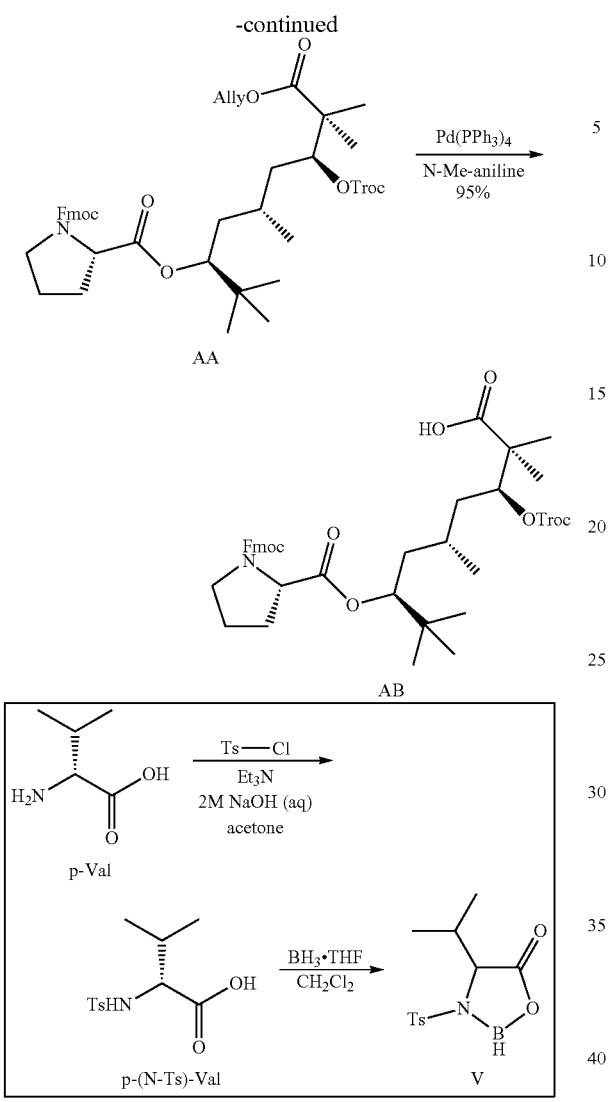

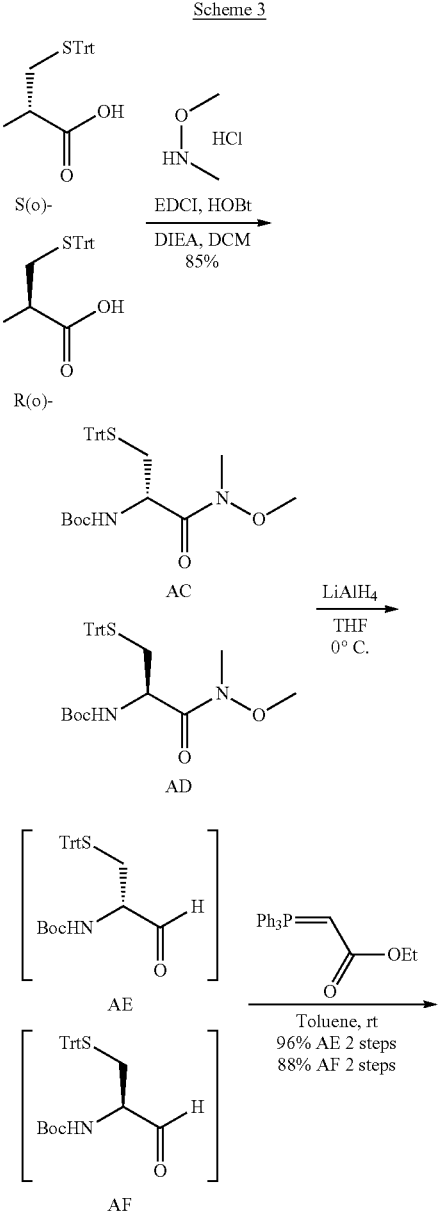

Scheme 3 wski, A. *Chem. Rev.* 1989, 89, 149-164; Fehrentz, J. A.; Castro, B. *Synthesis* 1983, 676-678; Mali, S. M.; Bandyopadhyay, A.; Jadhav, S. V.; Kumar, M. G; Gopi, H. N. *Org. Biomol. Chem.* 2011, 9, 6566-6574]. One possibility for the enhanced selectivity is that reduction with LiAlH$_4$ may produce a stable lithium-chelated intermediate [Rein, T.; Kreuder, R.; Zezschwitz P. V.; Wulff, C.; Reiser, O. *Angew. Chem. Int. Ed. Engl.* 1995, 34, 1023-1025; Reetz, M. T. *Angew. Chem. Int. Ed. Engl.* 1991, 30, 1531-1546]. Subsequent reduction of the conjugated double bond in AG and AH using NaBH$_4$ in 95% ethanol afforded saturated compounds AI and AJ in 35% yield. Similar yields were also observed for hydrogenation with RhC(PPH$_3$)$_3$/H$_2$ in toluene at 50° C., however, these also required harsh purification. Finally, ethyl esters AI and AJ were transformed into allyl esters AM and AN through hydrolysis and subsequent alkylation transformations.

The synthesis of modified cysteine units AM and its enantiomer AN was achieved by following published procedures with minor modifications, as depicted in Scheme 3[Chen, Q.-Y.; Liu, Y.; Luesch, H. *ACS Med. Chem. Lett.* 2011, 2, 861-865]. The Weinreb amides AC and AD from S- (or R-) N-Boc-Cys(S-Trt)-OH, respectively, were reduced to aldehydes AE and AF, which were selectively converted into chain-extended modified cysteines, (E)-AG and (E)-AH, by Witting olefination. During this conversion, the choice of reductant is of importance because α-amino aldehydes are known to beeasily racemized [Rein, T.; Kreuder, R.; Zezschwitz P. V.; Wulff, C.; Reiser, O. *Angew. Chem. In. Ed. Eng.* 195, 34, 1023-1025; Reetz, M. T. *Angew. Chem. Int. Ed. Eng.* 1991, 30, 1531-1546; Gryko, D.; Chalko, J.; Jurczak, J. *Chiralty,* 2003, 15, 514-541]. The method using lithium aluminum hydride (LiAlH$_4$) in THF at 0° C. appeared to have decreased the racemization rate compared with that using DIBAL-H in toluene at −78° C. in this preparation [Ma, D.; Zou, B.; Cai, G.; Hu, X.; Liu, J. *O. Chem. Eur. J.* 2006, 12, 7615-7626; Rein, T.; Kreuder, R.; Zezschwitz P. V.; Wulff, C.; Reiser, O. *Angew. Chem. Int. Ed. Engl.* 1995, 34, 1023-1025; Reetz, M. T. *Angew. Chem. Int. Ed. Engl.* 1991, 30, 1531-1546; Gryko, D.; Chalko, J.; Jurczak, J. *Chiralty,* 2003, 15, 514-541; Jurczak, J.; Golebio-

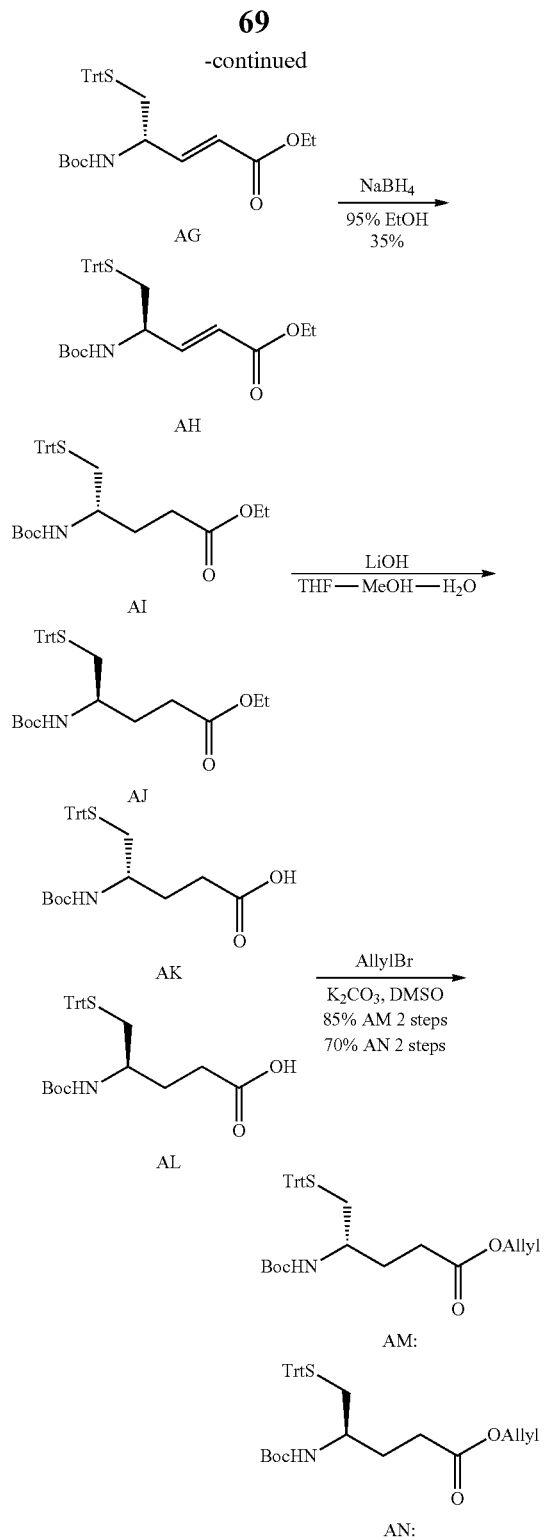

TABLE 1

Screening of coupling reagents for preparation of AO, AX and BB (% yield)

| Entry | EDCI | HATU | BOP | BEP | PyAOP |
|---|---|---|---|---|---|
| 1(T→AO) | 63% | 50% | 80% | 87% | —[a] |
| 2(AB→AX) | —[a] | 20% | — | 47%[b] | 89% |
| 3(T→BB) | —[a] | —[a] | 62% | —[a] | 91% |

[a] Coupling reagent was not tried.
[b] H NMR is complex.

Thiazoline ring formation proceeded smoothly for AO and AT to yield AP and AU, respectively, using $Ph_3P=O$/$Tf_2O$ in $CH_2Cl_2$ at 0° C. However, these same conditions required 3 h for complete starting material consumption to afford cyclized compound BC (from BB) and only afforded a 29% yield of AY from AX, and only with extended reaction times and elevated temperatures (Table 2, entry 5). Table 2 captures the conditions profiled in attempts to optimize the conversion of AX to AY. For $TiCl_4$ mediated thiazoline formation, at 25-40° C. in 5-40 h, only 30-34% yield was obtained (entries 6-7); however, the yield improved to 72% when the reaction temperature was increased to 60° C. (Table 2, entry 8).

TABLE 2

Exploring the conditions of thiazoline formation of AY from AX

| entry | reagents[a] | solvent | temp (° C.) | time (h)[c] | yield (%)[d] |
|---|---|---|---|---|---|
| 1 | $Ph_3PO$/$Tf_2O$ | $CH_2Cl_2$ | 0 | 0.5 | trace |
| 2 | $Ph_3PO$/$Tf_2O$ | $CH_2Cl_2$ | 0 | 24 | trace |
| 3 | $Ph_3PO$/$Tf_2O$ | $CH_2Cl_2$ | 25 | 24 | trace |
| 4 | $Ph_3PO$/$Tf_2O$ | $(ClCH_2)_2$ | 60 | 6 | trace |
| 5 | $Ph_3PO$/$Tf_2O$ | $(ClCH_2)_2$ | 60 | 15 | 29 |
| 6 | $TiCl_4$ | $CH_2Cl_2$ | 25 | 5 | 34 |
| 7 | $TiCl_4$ | $CH_2Cl_2$ | 25-40[b] | 24-40[b] | 30 |
| 8 | $TiCl_4$ | $(ClCH_2)_2$ | 60 | 2.5 | 72 |

[a] Reactions were carried out using $Ph_3P=O$ (8 eq.) and $Tf_2O$ (4 eq.) for entries 1-5. $TiCl_4$ (5 eq.) for entries 6-8 (10-mg scale reactions) or 2.5-3.0 eq. $TiCl_4$ used for >30-mg scale reactions).
[b] This reaction first was carried out at 25° C. for 24 h, when large amounts of starting material were still found by TLC and MS, and then this reaction was heated under reflux for another 16 h.
[c] Reactions were monitored by MS, the bands of starting material and product on TLC were very close.
[d] Products were isolated using preparative TLC plates.

AR, AW, BA, and BE were synthesized as depicted in Scheme 4. The N-Boc groups in T, U, and AB were selectively removed with TMSOTf in the presence of 2,6-lutidine and coupling with AM or AN afforded AO, AS, AX, and BB. Table 1 captures the coupling agent screen to affect the production of AO, AX and BB. Coupling with BEP gave the highest yield of 87% in the synthesis of AO, while PyAOP yielded the best results in the synthesis of AX and BB (i.e., 89% and 91%, respectively).

In order to minimize and/or avoid the elimination of the O-Troc group, thiazoline-containing intermediates AP, AU, AY, and BC were immediately treated with Zn—$NH_4OAc$ to remove the Troc group, which then provided AQ, AV, AZ, and BD in 55-90% yield. In the preparation of AV, 15.5% dehydration compound (e.g. dehyd-AV) was isolated; however, no dehydration compound was detected in the preparation of AQ, AZ, or BD. The removal of allyl ester of AQ, AV, AZ, and BD using $Pd(PPh_3)_4$/N-methylaniline provided acids AR, AW, BA, and BE.

Scheme 4 a) Synthesis of AO, AR

AM
↓ TMSOTf
2,6-lutidine
CH$_2$Cl$_2$

T
↓ BEP
DIEA
THF
87%

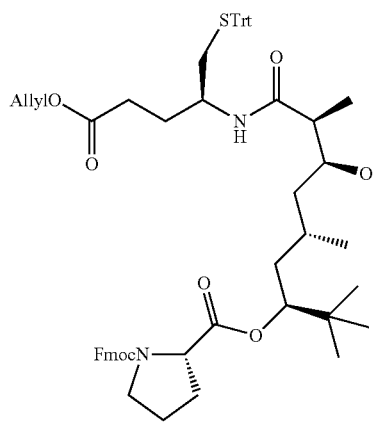

AO

Ph$_3$P=O
Tf$_2$O
CH$_2$Cl$_2$
0° C., 30 min
→

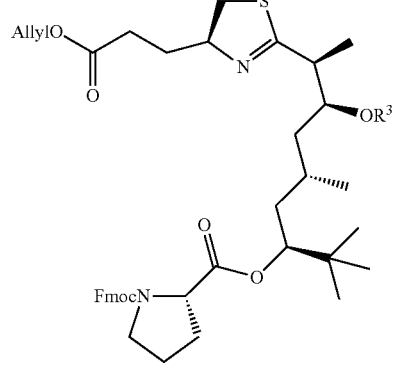

Pd(PhP$_3$)$_4$
N-methylaniline
THF, 95%
→

Zn, NH$_4$OAc (aq.)
THF, 90% 2 steps
AP: R$^3$ = Troc
AQ: R$^3$ = H

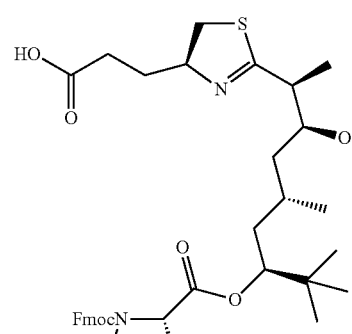

AR b) Synthesis of AT, AW

AM
↓ TMSOTf
2,6-lutidine
CH$_2$Cl$_2$

U
↓ HATU
DIEA
CH$_2$Cl$_2$
82%

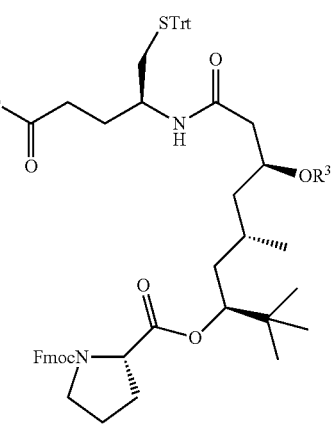

Ph$_3$P=O
Tf$_2$O
CH$_2$Cl$_2$
0° C., 30 min
→

TrocCl
pyridine, DMAP
CH$_2$Cl$_2$, 80%
AS: R$^3$ = H
AT: R$^3$ = Troc

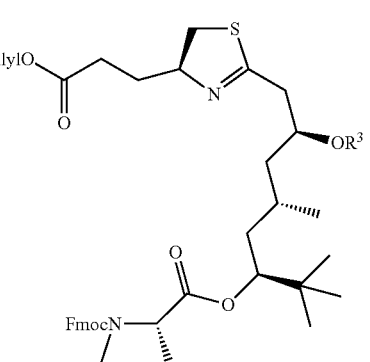

Pd(PhP$_3$)$_4$
N-methylaniline
THF, 95%
→

Zn, NH$_4$OAc (aq.)
THF, 76% 2 steps
AU: R$^3$ = Troc
AV: R$^3$ = H

73
-continued
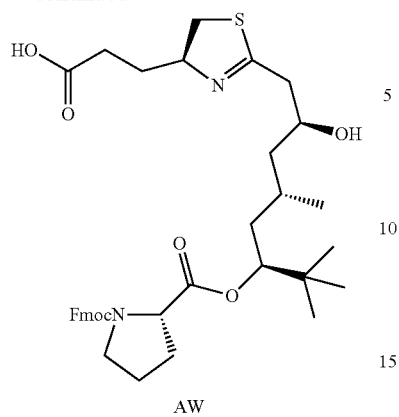
AW
c) Synthesis of AX, BA
AM
↓ TMSOTf
2,6-lutidine
CH₂Cl₂
AB  →  PyAOP
DIEA
THF
89%
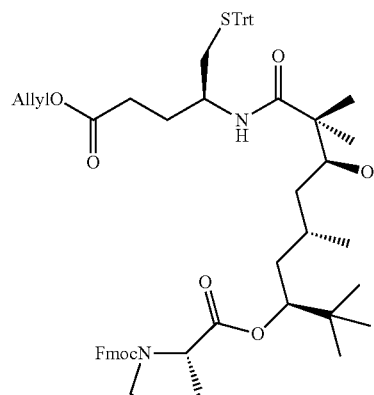
AX
→ TiCl₄
ClCH₂CH₂Cl
50° C., 2.5 h
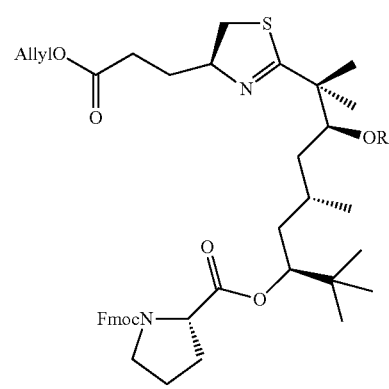
Zn, NH₄OAc (aq.)
THF, 55% 2 steps
⎯ AY: R³ = Troc
→ AZ: R³ = H
74
-continued
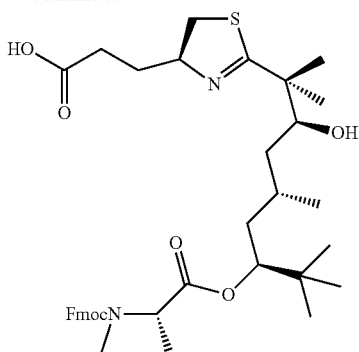
BA
d) Synthesis of BB, BE
AN
↓ TMSOTf
2,6-lutidine
CH₂Cl₂
T  →  PyAOP
DIEA
THF
91%
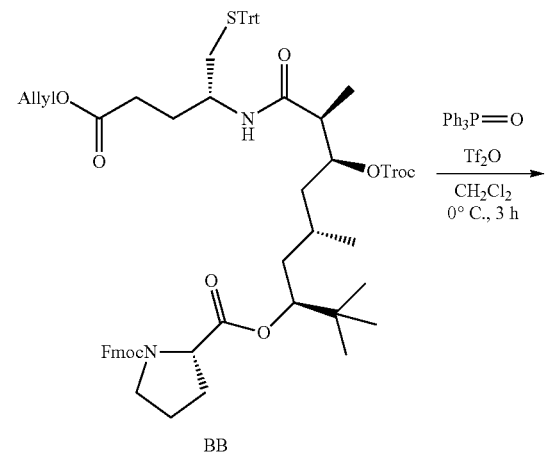
BB
→ Ph₃P=O
Tf₂O
CH₂Cl₂
0° C., 3 h
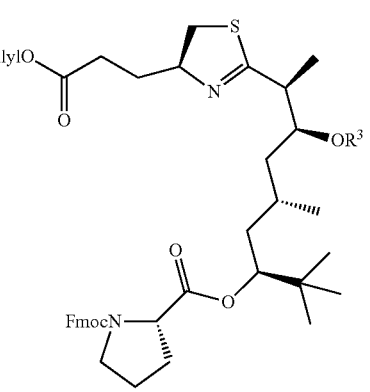
Zn, NH₄OAc (aq.)
THF, 79% 2 steps
⎯ BC: R³ = Troc
→ BD: R³ = H
→ Pd(PhP₃)₄
N-methylaniline
THF, 84%
→ Pd(PhP₃)₄
N-methylaniline
THF, 90%

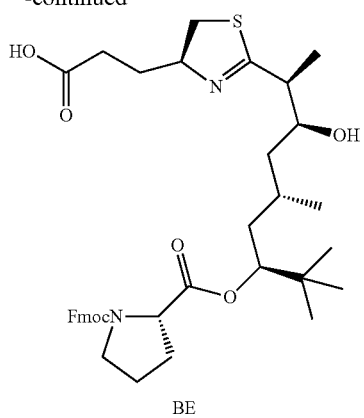

BE

BK, BL, BM, and BN were synthesized as depicted in Scheme 5. Fmoc-protected tripeptide BF was treated with Et₂NH in MeCN to liberate the corresponding amine, which was then coupled with acids AR, AW, BA, and BE to provide BG, BH, BI, and BJ, respectively, in yields of 71-95% [Chen, Q.-Y.; Liu, Y.; Luesch, H. *ACS Med. Chem. Let.* 2011, 2, 861-865; Doi, T.; Numajiri, Y.; Munakata, A.; Takahashi, T. *Org. Lett.* 2006, 8, 531-534; Numajiri, Y.; Takahashi, T.; Doi, T. *Chem. Asian J.* 2009, 4, 111-125]. PyAOP was chosen as coupling reagent in the preparation of BG, BI, and BJ with acceptable results [Doi, T.; Numajiri, Y.; Takahashi, T.; Takagi, M.; Shin-ya, K. *Chem. Asian J.* 2011, 6, 180-188; Chen, J.; Forsyth, C. J. *J. Am. Chem. Soc.* 2003, 125, 8734-8735]. However, for C34-non-methyl-acid AW (Table 3), PyAOP or HATU as coupling reagent gave yields of BH as low as 10-35%, 30-50% yields of starting material AW was dehydrated (via elimination to form a double bond at C34-C35 or intramolecular cyclization to form lactone between COOH and C35-OH of AW), and 5-20% of dehy-BH. However, coupling with DEPBT afforded the desired product BH in 72% yield along with 13% of dehydrated compound, while only trace amounts of AW were dehydrated to form a double bond or as a result of intramolecular cyclization. These results are summarized in Table 3.

TABLE 3

Screening of coupling reagents for reaction of AW and BF to BH

| entry | coupling reagent | yield of BH | yield of dehyd-BH | ratio AW to dehyd-AW |
|---|---|---|---|---|
| 1 | HATU | 10% | 5% | 1:1 |
| 2 | PyAOP | 35% | 20% | 3:1 |
| 3 | DEPBT | 72% | 13% | 20:1 |

Cleavage of the O-allyl esters from BG, BH, BI, and BJ with Pd(PPh₃)₄/N-methylaniline and Et₂NH/MeCN, followed by macrocyclization with PyAOP or DEPBT in diluted solution and subsequent purification by semi-preparative HPLC afforded final targets BK, BL, BM, and BN in yields of 60%, 25%, 70% and 45%, respectively. Along with BL and BN, there were 10% and 5% dehydrated cyclized compounds isolated, respectively. The yields of cyclization and final total yields for the longest linear sequence from pivalaldehyde are summarized in Table 4.

TABLE 4

Summary of yields of final products BK, BL, BM, and BN

| | apratoxin S4 (BK) | apratoxin S7 (BL) | apratoxin S8 (BM) | apratoxin S9 (BN) |
|---|---|---|---|---|
| Yield$^a$ of cyclization | 60.0%$^c$ | 25.0% | 70.0% | 45.0% |
| Total yield | 5.0%$^d$ | 1.2% | 3.0% | 2.4% |

Note:
$^a$Yield over 3 steps.

For final total yields, BK has the most optimized yield of 5.0%. The lower yields of BL and BN resulted mainly from their dehydration propensity at C35 in the formation of the thiazoline ring and/or macrocyclization steps. However, the lower total yield of BM is due to the lower efficiency of the thiazoline ring formation presumably as a result of steric hindrance of gem-dimethyl at C34. Nevertheless, the prevention of dehydration of gem-dimethyl in the formation of the thiazoline ring (AZ) and the best yield (70%) during macrocyclization (BM) supported the design of gem-dimethyl analogue at C34 (i.e., minimizing and/or preventing dehydration at C34-C35).

Scheme 5

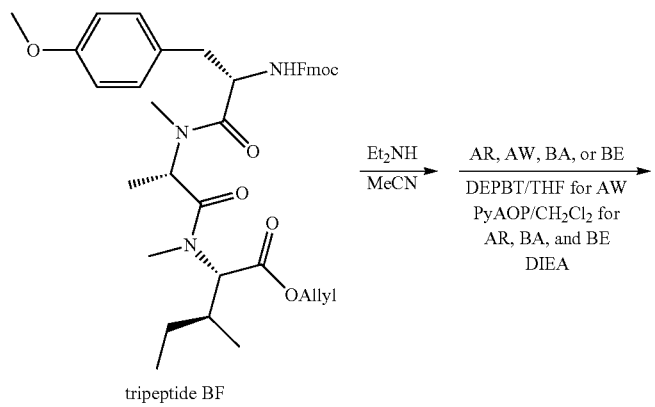

tripeptide BF

-continued

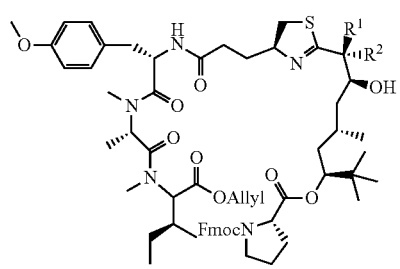

BG: R¹ = CH₃, R² = H (from AR, 95%)
BH: R¹ = R² = H (from AW 72%)
BI: R¹ = R² = CH₃ (from BA 90%)

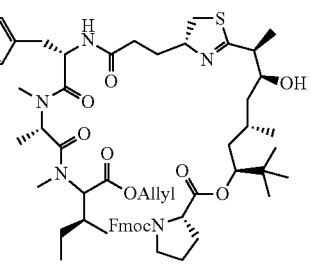

BJ: (from BE 71%)

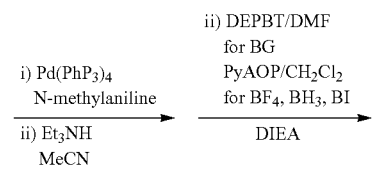

i) Pd(PhP₃)₄
N-methylaniline
ii) Et₃NH
MeCN ii) DEPBT/DMF
for BG
PyAOP/CH₂Cl₂
for BF₄, BH₃, BI
DIEA

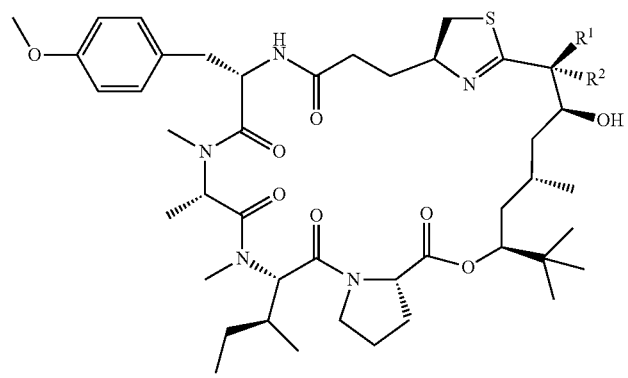

BK (Apratoxin S4): R¹ = CH₃, R² = H (from BH) (60% 3 steps)
BL (Apratoxin S7): R¹ = R² = H (from BI) (25% 3 steps)
BM (Apratoxin S8): R¹ = R² = CH₃ (from BJ) (70% 3 steps)

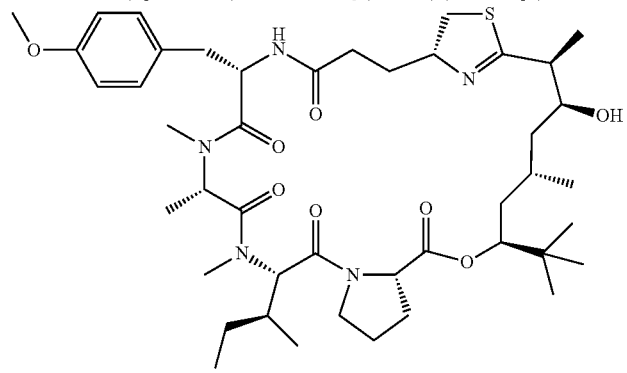

BN (Apratoxin S9) (from BK)
(45% 3 steps)

Methods of Treatment

In one aspect, the invention provides a method of treating a disease, disorder, or symptom thereof in a subject, comprising contacting the subject with a compound any of the formulae herein, in an amount and under conditions sufficient to treat the disease, disorder, or symptom thereof in the subject.

In one aspect, the invention provides a method of treating a disease, disorder, or symptom thereof in a subject, wherein the disorder is Hashimoto's thyroiditis, Pernicious anemia, Addison's disease, Type I diabetes, Rheumatoid arthritis, Systemic lupus erythematosus, Dermatomyositis, Sjogren syndrome, Lupus erythematosus, Multiple sclerosis, Myasthenia gravis, Reactive arthritis, Grave's disease, Celiac disease—sprue or cystic fibrosis.

In one aspect, the invention provides a method of modulating the proliferation activity of a cell in a subject, comprising contacting the subject with a compound of any of the formulae herein, in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of any of the formulae herein.

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein, such that said subject is treated for said disorder.

In certain embodiments, the invention provides a method of treating a disorder, wherein the disorder is cancer (e.g., breast, colon, pancreas) or solid tumor.

In certain embodiments, the subject is a mammal, preferably a primate or human.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In another embodiment, the invention provides a method as described above, wherein the effective amount of the compound of any of the formulae herein ranges from about 0.005 µg/kg to about 200 mg/kg. In certain embodiments, the effective amount of the compound of any of the formulae herein ranges from about 0.1 mg/kg to about 200 mg/kg. In a further embodiment, the effective amount of compound of any of the formulae herein ranges from about 10 mg/kg to 100 mg/kg.

In other embodiments, the invention provides a method as described above wherein the effective amount of the compound of any of the formulae herein ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of any of the formulae herein is administered intravenously, intramuscularly, subcutaneously, intracerebroventricularly, orally or topically.

In other embodiments, the invention provides a method as described above, wherein the compound of any of the formulae herein is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease. Another object of the present invention is the use of a compound as described herein (e.g., of any formulae herein) for use in the treatment of a cell proliferation disorder or disease.

Pharmaceutical Compositions

In one aspect, the invention provides a pharmaceutical composition comprising the compound of any of the formulae herein and a pharmaceutically acceptable carrier.

In another embodiment, the invention provides a pharmaceutical composition wherein the compound of any of the formulae herein is a compound of any of Formula I and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae herein, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific apratoxin compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

All commercial reagents were used without further purification unless otherwise noted. Solvents were purified according to the guidelines in *Purification of Laboratory Chemicals* (5$^{th}$ edition, W. L. F. Armarego, Christina L. L. Chai, Butterworth-Heinemann: Oxford, 2003). Tetrahydrofuran (THF) and diethyl ether (Et$_2$O) were distilled from sodium chips in the presence of a small amount of benzophenone; CH$_2$Cl$_2$ and toluene were distilled from CaH$_2$; MeCN, N,N-dimethylformamide (DMF) were dried with 4 Å molecular sieves (MS) and MeOH dried with 3 Å MS; 4 M Hydrochloric acid (HCl) solution in ethyl acetate was prepared by dissolving HCl gas (yielding by dropping aqueous hydrochloric acid (34%) to concentrated sulfuric acid (98%)) to ethyl acetate. All reactions were performed in heat-gun dried flasks (400° C. under reduced pressure) under an inert atmosphere of anhydrous Ar unless otherwise noted. Thin layer chromatography was performed on EMD silica gel 60 Å F$_{254}$ glass plates and preparative thin layer chromatography was performed on Whatman silica gel 60 Å F$_{254}$ glass plates (layer thick 1000 μm). Flash column chromatography was performed with Fisher 170-400 mesh silica gel. Nuclear magnetic resonance (NMR) spectra were recorded on a Varian Mercury 400 MHz, Bruker Avance 11600, Bruker Avance 111600 MHz or Aligent VNMR 600 MHz spectrometer as indicated in the data list. Chemical shifts for proton nuclear magnetic resonance ($^1$H NMR) spectra are reported in parts per million relative to the signal residual CDCl$_3$ at 7.26 ppm; Chemicals shifts for carbon nuclear magnetic resonance ($^{13}$C NMR) spectra are reported in parts per million relative to the center line of the CDCl$_3$ triplet at 77.16 ppm; The abbreviations s, d, dd, ddd, dddd, t, q, br and m stand for the resonance multiplicity singlet, doublet, doublet of doublets, doublet of doublet of doublets, doublet of doublet of doublet of doublets, triplet, quartet, broad and multiplet, respectively. Optical rotation was measured on a Perkin-Elmer 341 polarimeter (Na D line) using a microcell of 1-dm path length. High resolution mass spectra (HRMS) data were obtained using an Agilent-LC-TOF mass spectrometer with an APCI/ESI multimode ion source detector LR-MS data was obtained using a 3200 QTrap triple quadrupole mass spectrometer and detection by electrospray ionization-MS in the positive ion mode.

Example 1: Preparation of Aldehyde K (S)-5,5-dimethyl-4-hydroxyhexan-2-one (A)

D-proline (4.082 g, 35.46 mmol) was added to the mixture of acetone (208 mL) and DMSO (800 mL) at room temperature and the mixture was stirred at the same temperature for 1 h before pivalaldehyde (10.18 g/13 mL, 118.2 mmol) was added. After stirring at room temperature for 4 days, the mixture was cooled to 0° C. with an ice-water bath and a saturated aqueous NH$_4$C solution (800 mL) was added to quench the reaction. The mixture was extracted with ethyl acetate (1000 mL×3) and the extract was concentrated under reduced pressure to remove most of the ethyl acetate and acetone. Then the concentrated mixture was diluted with another 800 mL of ethyl acetate and washed with small portions of water (50 mL×5) to remove most of the DMSO. The organic layer was dried with anhydrous MgSO$_4$ and concentrated under reduced pressure. The residue was purified by column chromatography on silica gel (8-20% ethyl acetate in hexane) to give product A (14 g, 82%) as a colorless liquid [Luesch, H.; Yoshida, W. Y.; Moore, R. E.; Paul, V. J.; Corbett, T. H. *J. Am. Chem. Soc.* 2001, 123, 5418-5423; Luesch, H.; Yoshida, W. Y.; Moore, R. E.; Paul, V. J., *Bioorg. Med. Chem.* 2002, 10, 1973-1978; Matthew, S.; Schupp, P. J.; Luesch, H. *J. Nat. Prod.* 2008, 71, 1113-1116; Gutierrez, M.; Suyama, T. L.; Engene, N.; Wingerd, J. S.; Matainaho, T.; Gerwick, W. H. *J. Nat. Prod.* 2008, 71, 1099-1103; Tidgewell, K.; Engene, N.; Byrum, T.; Media, J.; Doi, T.; Valeriote, F. A.; Gerwick, W. H. *Chem Bio Chem* 2010, 11, 1458-1466; Thornburg, C. C.; Cowley, E. S.; Sikorska, J.; Shaala, L. A.; Jane E. Ishmael, J. E.; Youssef, D. T. A.; McPhail, K. L. *J. Nat. Prod.* 2013, 76, 1781-1788; Chen, Q.-Y.; Liu, Y.; Luesch, H. *ACS Med. Chem. Lett.* 2011, 2, 861-865; Doi, T.; Numajiri, Y.; Munakata, A.; Takahashi, T. *Org. Lett.* 2006, 8, 531-534; Numajiri, Y.; Takahashi, T.; Doi, T. *Chem. Asian J.* 2009, 4, 111-125; Xu, Z.; Chen, Z.; Ye, T. *Tetrahedron: Asymmetry* 2004, 15, 355-363; Doi, T.; Numajiri, Y.; Takahashi, T.; Takagi, M.; Shin-ya, K. *Chem. Asian J.* 2011, 6, 180-188; Chen, J.; Forsyth, C. J. *J. Am. Chem. Soc.* 2003, 125, 8734-8735; Ma, D.; Zou, B.; Cai, G.; Hu, X.; Liu, J. O. *Chem. Eur. J.* 2006, 12, 7615-7626; Zou, B.; Wei, J.; Cai, G.; Ma, D. *Org. Lett.* 2003, 5, 3503-3506; Gilles, A.; Martinez, J.; Cavelier, F. *J. Org. Chem.* 2009, 74, 4298-4304; Robertson, B. D.; Wengryniuk, S. E.; Coltart, D. M. *Org. Lett.*, 2012, 14, 5192-5195]. $^1$H NMR (400 MHz, CDCl$_3$): δ 3.72 (ddd, J=10.8, 3.6, 2.0 Hz, 1H), 2.85 (brm, 1H), 2.63 (dd, J=17.6, 2.4 Hz, 1H), 2.48 (dd, J=17.2, 10.8 Hz, 1H), 2.20 (s, 3H), 0.90 (s, 9H).

(S)-5,5-Dimethyl-4-(tert-butyldimethylsilyloxy)hexan-2-one (B)

tert-Butyldimethylsilyl chloride (TBS-Cl) (32.184 g, 213.533 mmol) and imidazole (28.166 g, 413.72 mmol) were added to the solution of compound A (19.246 g, 133.458 mmol) in DMF (30 mL). After stirring at room temperature for 24 h under Ar, the reaction was quenched by addition of 55 mL methanol and 450 mL water. The mixture was extracted with ethyl acetate (500 mL×3), the combined organic layers were concentrated in vacuo and purified by column chromatography on silica gel (5% ethyl acetate in hexane) to give product B (30 g, 87%) as a colorless liquid [Liu, Y.; Law, B. K.; Luesch, H., *Mol. Pharmacol.* 2009, 76, 91-104; Lurje, G.; Lenz, H.-J. *Oncology* 2009, 77, 400-410; Hurwitz, H.; Fehrenbacher, L.; Novotny, W.; Cartwright, T.; Hainsworth, J.; Heim, W.; Berlin, J.; Baron, A.; Griffing, S.; Holmgren, E.; Ferrara, N.; Fyfe, G.; Rogers, B.; Ross, R.; Kabbinavar, F. *N. Engl. J. Med.* 2004, 350, 2335-2342; Koutras, A. K.; Starakis, I.; Kyriakopoulou, U.; Katsaounis, P.; Nikolakopoulos, A.; Kalofonos, H. P. *Curr. Med. Chem.* 2011, 18, 1599-1612]. $^1$H NMR (400 MHz, CDCl$_3$): δ 3.95 (dd, J=6.0, 4.0 Hz, 1H), 2.61 (dd, J=17.2 Hz, 1H), 2.49 (dd, J=17.6, 6.4 Hz, 1H), 2.15 (s, 3H), 0.86 (s, 9H), 0.84 (s, 9H), 0.06 (s, 3H), 0.06 (s, 3H) ppm. $^{13}$C NMR (100 MHz, CDCl$_3$): δ 207.9, 75.1, 48.2, 35.7, 31.43, 26.2, 26.0, 18.4, −4.0, −4.8 ppm.

(S)-tert-Butyl (1-tert-butylbut-3-enyloxy)dimethylsilane (D)

NaBH$_4$ (8.8 g, 232.4 mmol) was added to the solution of compound B (30.0 g, 116.2 mmol) in MeOH (300 mL) at 0° C. After being stirred at the 0° C. for 40 min, the reaction was concentrated and then 300 mL water was added at 0° C. The mixture was extracted with ethyl acetate (300 mL×3), washed sequentially with brine (300 mL×2) and water (200 mL×2), dried with anhydrous MgSO$_4$, and evaporated in vacuo to give the crude alcohol C, which was used in the next step without further purification.

Et$_3$N (32.2 ml, 232.4 mmol) and MsCl (18 ml, 232.4 mmol) were added to the solution of the above crude C in dry CH$_2$Cl$_2$ (300 mL) at 0° C. under an Ar atmosphere. After stirring at the same temperature for 2.5 h, this reaction was quenched by brine (150 mL). The organic layer was separated and the water layer was extracted with CH$_2$Cl$_2$ (100 mL×2). The combined CH$_2$Cl$_2$ fractions were washed with water (100 mL×2), dried with anhydrous MgSO$_4$ and evaporated in vacuo to give the crude mesylate.

tBuOK (43.0 g, 383.5 mmol) was added to the solution of the above crude mesylate in dried toluene (400 mL). The suspended mixture was heated to reflux for 1 h, cooled to room temperature and 200 mL water was added. The organic layer was separated and the water layer was extracted with heptane (300 mL×3). The combined toluene and heptane layers were washed with brine (200 mL×3) and water (200 mL×2), dried with anhydrous MgSO$_4$, evaporated in vacuo and purified by column chromatography (100% hexane) to give product D (26 g, 92.5% 3 steps) as a colorless liquid [Liu, Y.; Law, B. K.; Luesch, H., *Mol. Pharmacol.* 2009, 76, 91-104; Lurje, G.; Lenz, H.-J. *Oncology* 2009, 77, 400-410; Hurwitz, H.; Fehrenbacher, L.; Novotny, W.; Cartwright, T.; Hainsworth, J.; Heim, W.; Berlin, J.; Baron, A.; Griffing, S.; Holmgren, E.; Ferrara, N.; Fyfe, G.; Rogers, B.; Ross, R.; Kabbinavar, F. *N. Engl. J. Med.* 2004, 350, 2335-2342; Koutras, A. K.; Starakis, I.; Kyriakopoulou, U.; Katsaounis, P.; Nikolakopoulos, A.; Kalofonos, H. P. *Curr. Med. Chem.* 2011, 18, 1599-1612]. $^1$H NMR (400 MHz, CDCl$_3$): δ 5.88 (dddd, J=16.8, 9.6, 7.2, 7.2 Hz, 1H), 5.00 (m, 1H), 3.32 (dd, J=8.0, 4.0 Hz, 1H), 2.35 (m, 1H), 2.13 (m, 1H), 0.90 (s, 9H), 0.87 (s, 9H), 0.04 (s, 3H), 0.03 (s, 3H) ppm. $^{13}$C NMR (100 MHz, CDCl$_3$): δ 137.9, 115.7, 80.2, 38.5, 36.3, 26.7, 26.3, 18.5, −3.1, −4.1 ppm.

(S)-2,2-Dimethyl-5-hexen-3-ol (E)

The solution of tetra-n-butylammonium fluoride trihydrate (TBAF) (82.07 g, 260.116 mmol) in THF (220 mL) was added to the mixture of compound D (21.0 g, 86.705 mmol) and 4 Å molecular sieves (22 g, pre-dried at 450° C. under reduced pressure 1 h) in anhydrous THF (300 mL) at 0° C. Then the reaction mixture was stirred at room temperature overnight, filtered through a small pad of Celite (washed with diethyl ether). The filtrate was quenched with 200 mL water, extracted with diethyl ether (300 mL×3), washed with brine (200 mL×2), dried over anhydrous MgSO$_4$, concentrated with cooling/condensing fraction distillation system under moderate vacuum, and further concentrated by Vigreux fraction distillation column. The concentrated mixture was purified by column chromatography and eluted by 3%-5% diethyl ether in pentane. The eluted product fractions were also concentrated by cooling/condensing fraction distillation system under moderate vacuum to give product E and further distilled by Vigreux fraction distillation column to provide product E (10.5 g, 95%) [Xu, Z.; Chen, Z.; Ye, T. *Tetrahedron: Asymmetry* 2004, 15, 355-363; Doi, T.; Numajiri, Y.; Takahashi, T.; Takagi, M.; Shin-ya, K. *Chem. Asian J.* 2011, 6, 180-188; Chen, J.; Forsyth, C. J. *J. Am. Chem. Soc.* 2003, 125, 8734-8735; Ma, D.; Zou, B.; Cai, G.; Hu, X.; Liu, J. O. *Chem. Eur. J.* 2006, 12, 7615-7626; Zou, B.; Wei, J.; Cai, G.; Ma, D. *Org. Lett.* 2003, 5, 3503-3506; Kinnaird, J. W. A.; Ng, P. Y.; Kubota, K.; Wang, X.; Leighton, J. L. *J. Am. Chem. Soc.* 2002, 124, 7920-7921]. $^1$H NMR (400 MHz, CDCl$_3$): δ 5.86 (dddd, J=14.4, 10.4, 8.8, 6.0 Hz, 1H), 5.14 (m, 2H), 3.25 (dd, J=10.4, 2.0 Hz, 1H), 2.39-2.33 (m, 1H), 1.98 (ddd, J=13.6, 9.6, 9.6 Hz, 1H), 0.91 (s, 9H) ppm. $^{13}$C NMR (100 MHz, CDCl$_3$): δ136.7, 117.9, 78.2, 36.7, 34.7, 25.9 ppm.

(S)-Acrylic acid 1-tert-butyl-but-3-enyl ester (F)

Acryloyl chloride (8.7 mL, 106.6 mmol) and triethylamine (34 mL, 246.0 mmol) were added sequentially to the solution of compound E (10.5 g, 82.0 mmol) in anhydrous diethyl ether (300 mL) at 0° C. The reaction was warmed to room temperature and stirred at room temperature for 4 h, then poured into cold water (300 mL) and extracted with diethyl ether (300 mL×4). The combined organic layers were washed with saturated NaHCO$_3$ (300 mL×2), saturated NH$_4$Cl (300 mL), brine (300 mL), dried with anhydrous MgSO$_4$, concentrated (first by cooling/condensing fraction distillation system under moderate vacuum and further by Vigreux fraction distillation column) and purified by column chromatography to give product F (14.5 g, 97%) [Liu, Y.; Law, B. K.; Luesch, H., *Mol. Pharmacol.* 2009, 76, 91-104; Ruan, W.-J.; Lai, M.-D. *Med. Oncol.* 2004,21, 1-7; Luesch, H.; Chanda, S. K.; Raya, R. M.; DeJesus, P. D.; Orth, A. P.; Walker, J. R.; Izpisdá Belmonte, J. C.; Schultz, P. G. *Nat Chem Biol.* 2006, 2, 158-167]. *Because the compound easily evaporates along with solvent, the product fractions from the column chromatography were also concentrated first by cooling/condensing fraction distillation system under moderate vacuum and further by Vigreux fraction distillation column.*

(6S)-6-tert-Butyl-5,6-dihydro-pyran-2-one (G)

Ti(OiPr)$_4$ (1.3 mL, 4.39 mmol) was added to the solution of F (4.0 g, 21.96 mmol) in CH$_2$Cl$_2$ (600 mL, degassed) under Ar. The resulting solution was refluxed for 1 h, then Grubb's second generation catalyst (0.932 g, 1.098 mmol) in CH$_2$Cl$_2$ (30 mL, degassed) was added under refluxing conditions. The reaction mixture continued to reflux for another 4 h, was then cooled to room temperature, evaporated in vacuo and purified by column chromatography (eluted by diethyl ether/pentane 2:7) to give product G (3.05 g, 90%) as a colorless oil [Liu, Y.; Law, B. K.; Luesch, H., *Mol. Pharmacol.* 2009, 76, 91-104; Lurje, G.; Lenz, H.-J. *Oncology* 2009, 77, 400-410; Hurwitz, H.; Fehrenbacher, L.; Novotny, W.; Cartwright, T.; Hainsworth, J.; Heim, W.; Berlin, J.; Baron, A.; Griffing, S.; Holmgren, E.; Ferrara, N.; Fyfe, G.; Rogers, B.; Ross, R.; Kabbinavar, F. *N. Engl. J. Med.* 2004, 350, 2335-2342; Koutras, A. K.; Starakis, I.; Kyriakopoulou, U.; Katsaounis, P.; Nikolakopoulos, A.; Kalofonos, H. P. *Curr. Med. Chem.* 2011, 18, 1599-1612; Ruan, W.-J.; Lai, M.-D. *Med. Oncol.* 2004, 21, 1-7; Luesch, H.; Chanda, S. K.; Raya, R. M.; DeJesus, P. D.; Orth, A. P.; Walker, J. R.; Izpisúa Belmonte, J. C.; Schultz, P. G. *Nat*

*Chem Biol.* 2006, 2, 158-167]. $^1$H NMR (400 MHz, CDCl$_3$): δ 6.91 (ddd, J=11.0, 6.4, 2.8 Hz, 1H), 6.01 (m, 1H), 4.06 (dd, J=12.0, 4.4 Hz, 1H), 2.39-2.24 (m, 1H), 1.00 (s, 9H) ppm. $^{13}$C NMR (100 MHz, CDCl$_3$): δ165.1, 145.7, 121.3, 85.4, 34.0, 25.6, 24.7 ppm.

(4R,6S)-6-tert-Butyl-4-methyl-tetrahydro-pyran-2-one (H)

Methyllithium (1.6 M in diethyl ether, 131 mL, 209.21 mmol) was added slowly (over 1 h) to the suspension of CuCN (9.37 g, 96.56 mmol) in diethyl ether at −78° C. After the mixture was stirred at the same temperature for 40 min, it was transferred to an ice-bath for another 40 min, then re-cooled to −78° C. before compound G (12.4 g, 80.47 mmol) was added slowly (over 1 h) in dried diethyl ether (150 mL). The reaction mixture was kept at −78° C. 40 min, warmed to −50-−40° C. for 40 min, −20° C. for 1 h, was then quenched with 5% FeCl$_3$ (300 mL), extracted with diethyl ether (300 mL×3), washed with brine (300 mL×3), dried with anhydrous MgSO$_4$, concentrated in vacuo, and purified by column chromatography (eluted by dietyl ether/pentane 1:4) to give product H (11.6 g, 85%) as a colorless oil [Liu, Y.; Law, B. K.; Luesch, H., *Mol. Pharmacol.* 2009, 76, 91-104; Lurje, G.; Lenz, H.-J. *Oncology* 2009, 77, 400-410; Hurwitz, H.; Fehrenbacher, L.; Novotny, W.; Cartwright, T.; Hainsworth, J.; Heim, W.; Berlin, J.; Baron, A.; Griffing, S.; Holmgren, E.; Ferrara, N.; Fyfe, G.; Rogers, B.; Ross, R.; Kabbinavar, F. *N. Engl. J. Med.* 2004, 350, 2335-2342; Koutras, A. K.; Starakis, I.; Kyriakopoulou, U.; Katsaounis, P.; Nikolakopoulos, A.; Kalofonos, H. P. *Curr. Med. Chem.* 2011, 18, 1599-1612; Ruan, W.-J.; Lai, M.-D. *Med. Oncol.* 2004, 21, 1-7; Luesch, H.; Chanda, S. K.; Raya, R. M.; DeJesus, P. D.; Orth, A. P.; Walker, J. R.; Izpisúa Belmonte, J. C.; Schultz, P. G. *Nat Chem Biol.* 2006, 2, 158-167]. $^1$H NMR (400 MHz, CDCl$_3$): δ 3.97 (dd, J=11.8, 3.6 Hz, 1H), 2.53-2.46 (m, 1H), 2.21-2.16 (m, 1H), 1.80 (dddd, J=14.0, 11.6, 7.2 Hz, 1H), 1.49 (ddd, J=14.4, 3.2, 3.2 Hz, 1H), 1.09 (d, J=6.4, 3H), 0.95 (s, 9H) ppm. $^{13}$C NMR (100 MHz, CDCl$_3$): δ173.4, 83.8, 37.1, 34.1, 29.9, 25.6, 24.1 ppm.

(3R,5S)-5-Hydroxy-3,6,6-trimethyl-heptanoic acid methoxy-methyl-amide (I)

Trimethylaluminum ((CH$_3$)$_3$Al) (2M in hexane, 102.5 ml, 205.90 mmol) was added to a solution of N,O-dimethylhydroxylamine hydrochloride (20.00 g, 204.90 mmol) in CH$_2$Cl$_2$ (300 mL) at −78° C., then warmed to room temperature and maintained at room temperature overnight. The solution of compound H (11.62 g, 68.30 mmol) in CH$_2$Cl$_2$ (150 mL) was added slowly to the above solution over 1 h at 0° C. The reaction mixture was stirred at 0° C. for 40 min and at room temperature for another 5 h, was then concentrated to about 300 mL, quenched with a sodium potassium tartrate (Rochelle's salt) solution (240 g in 500 mL water), extracted with ethyl acetate (500 mL×3), washed with brine (300 mL×2), dried with anhydrous MgSO$_4$ and purified by column chromatography (eluted by ethyl acetate/hexane 1:2) to give product I (14.2 g, 90%) as a thick colorless oil [Ruan, W.-J.; Lai, M.-D. *Med. Oncol.* 2004, 21, 1-7]. $^1$H NMR (400 MHz, CDCl$_3$): δ 3.68 (s, 3H), 3.18 (s, 3H), 3.13 (dd, J=10.4, 2.4 Hz, 1H), 2.71 (br, 1H), 2.47-2.41 (m, 1H), 2.31-2.28 (m, 2H), 1.43-1.29 (m, 2H), 1.02 (d, J=6.4 Hz, 3H), 0.87 (s, 9H) ppm. $^{13}$C NMR (100 MHz, CDCl$_3$): δ175.0, 76.5, 61.3, 39.6, 38.3, 34.8, 32.4, 26.4, 26.0, 22.5 ppm.

(3R,5S)-5-(4-Methoxy-benzyloxy)-3,6,6-trimethyl-heptanoic acid methoxy-methyl-amide (J)

4-Methoxybenzyl-2,2,2-trichloroacetimidate (3.7 mL, 17.8 mmol) and trifluoromethane sulfonic acid (TfOH) (7.9 µL, 0.089 mmol) was added sequentially to the solution of I (2.05 g, 8.9 mmol) in THF (20 mL) at 0° C. The resulting mixture was stirred at room temperature overnight and was then diluted with ethyl acetate (20 mL), quenched with saturated NaHCO$_3$ (20 ml), extracted with ethyl acetate (20 mL×3), dried with anhydrous MgSO$_4$ and evaporated in vacuo. Hexane (100 mL) was added to the residue, which resulted in the precipitation of a white solid (2,2,2-trichloroacetimidate). The solid was filtered off and the filtrate was concentrated and purified by column chromatography (eluted by 20-50% ethyl acetate in hexane) to give product J (1.74 g, 56%, 100% BRSM) (Recovered starting material 1.08 g and used in next cycle). [Xu, Z.; Chen, Z.; Ye, T. *Tetrahedron: Asymmetry* 2004, 15, 355-363; Ruan, W.-J.; Lai, M.-D. *Med. Oncol.* 2004, 21, 1-7] $^1$H NMR (400 MHz, CDCl$_3$): δ 7.31 (d, J=8.4 Hz, 2H), 6.86 (d, J=8.4 Hz, 2H), 4.60 (d, J=10.4 Hz, 1H), 4.49 (d, J=10.4, 1H), 3.78 (s, 3H), 3.67 (s, 3H), 3.19 (s, 3H), 3.07 (dd, J=8.4, 2.8 Hz, 1H), 2.52-2.50 (m, 1H), 2.32-2.22 (m, 2H), 1.54-1.40 (m, 2H), 1.01 (d, J=6.4 Hz, 3H), 0.93 (s, 9H) ppm. $^{13}$C NMR (100 MHz, CDCl$_3$): δ174.2, 159.0, 131.5, 129.5, 129.3, 113.8, 113.6, 85.7, 74.2, 61.3, 55.3, 39.1, 38.7, 36.3, 32.2, 27.8, 26.6, 21.7 ppm.

(3R,5S)-5-(4-Methoxy-benzyloxy)-3,6,6-trimethyl-heptanal (K)

Diisobutylaluminum hydride (M in toluene, 7.0 ml, 7.1 mmol) was added dropwise to a solution of J (996 mg, 2.836 mmol) in THF (60 mL) at −78° C. The reaction mixture was quenched with 10% Rochelle's salt solution (100 mL) and diethyl ether (100 mL) and was then stirred at −78° C. for 30 min. After the two phased mixture had been stirred vigorously at room temperature for 2 h, it was extracted with ethyl acetate (100 mL×3), washed with brine (60 mL×3), dried with anhydrous MgSO$_4$, concentrated in vacuo and purified by column chromatography (eluted by 8% ethyl acetate in hexane) to give the titled compound 700 mg (85%) as a colorless oil [Ruan, W.-J.; Lai, M.-D. *Med. Oncol.* 2004, 21, 1-7]. $^1$H NMR (400 MHz, CDCl$_3$): δ 9.68 (s, 1H), 7.28 (d, J=8.4 Hz, 2H), 6.87 (d, J=8.4 Hz, 2H), 4.57 (d, J=10.8 Hz, 1H), 4.48 (d, J=10.8, 1H), 3.79 (s, 3H), 2.45-2.49 (m, 1H), 2.21-2.10 (m, 2H), 1.50-1.38 (m, 2H), 1.00 (d, J=6.4 Hz, 3H), 0.94 (s, 9H) ppm. $^{13}$C NMR (100 MHz, CDCl$_3$): δ 202.9, 159.1, 131.2, 129.3, 113.8, 85.3, 74.5, 55.3, 50.2, 38.8, 36.3, 26.6, 25.7, 21.7 ppm.

Example 2: Preparation of Carboxylic Acid T (3R,4S,6S,8S)-8-(4-methoxybenzyloxy)-3,6,9,9-tetramethyldec-1-en-4-ol (N)

To the solution of K (234.1 mg, 0.801 mmol) in CH$_2$Cl$_2$ (8 mL) was added (S,S)-trans EZ-CrotylMix (mixture of L and Sc(OTf)$_3$) (943 mg, 1.602 mmol) at room temperature. This mixture was stirred vigorously at the same temperature for 2.5 h, then it was treated with 12 mL Et$_2$O and 12 ml 1 N aq. HCl. After this quenched mixture was stirred at room temperature for 30 min, it was filtered off to remove the precipitated solid, extracted with Et$_2$O (15 mL×3), washed with saturated NaHCO$_3$ (20 mL×2) and brine (20 mL), dried with anhydrous MgSO$_4$, evaporated in vacuo and purified by chromatography column (eluted by 3.5-4.5% ethyl acetate in hexane) to give product N (245.7 mg, 88%) as a colorless oil [Chen, Q.-Y.; Liu, Y.; Luesch, H. *ACS Med. Chem. Lett.* 2011, 2, 861-865; Numajiri, Y.; Takahashi, T.; Doi, T. *Chem. Asian J.* 2009, 4, 111-125]. $^1$H NMR (400 MHz, CDCl$_3$): δ 7.32 (d, J=8.4 Hz, 2H), 6.87 (d, J=8.8 Hz, 2H), 5.82-5.73 (m, 1H), 5.15-5.08 (m, 2H), 4.66 (d, J=10.4 Hz, 1H), 4.53 (d, J=10.4, 1H), 3.79 (s, 3H), 3.52-3.49 (m, 1H), 3.14 (dd, J=8.8, 2.4 Hz, 1H), 2.23-2.14 (m, 1H), 2.05-1.95 (br m, 1H), 1.72 (br, 1H), 1.60 (ddd, J=13.6, 10.4, 2.8 Hz, 1H), 1.50 (ddd, J=14.0, 8.8, 4.0 Hz, 1H), 1.38 (ddd, J=14.0, 9.6, 2.4 Hz, 1H), 1.13 (ddd, J=12.4, 10.4, 1.6 Hz, 1H), 1.05 (d, J=6.8 Hz, 3H), 0.99 (d, J=6.8 Hz, 3H), 0.96 (s, 9H) ppm. $^{13}$C NMR (100 MHz, CDCl$_3$): δ 159.0, 140.7, 131.7, 129.2, 116.2, 113.7, 85.2, 74.2, 72.3, 55.3, 45.3, 40.8, 39.8, 36.2, 26.6, 21.0, 16.2 ppm.

(3R,4S,6S,8S)-8-(4-methoxybenzyloxy)-3,6,9,9-tetramethyldec-1-en-4-yl 2,2,2-trichloroethyl carbonate (P)

To the solution of N (201.2 mg, 0.578 mmol) and pyridine (280 μL, 3.466 mmol) in CH$_2$Cl$_2$ (4.0 ml) was added 2,2,2-trichloroethoxylcarbonyl chloride (Troc-Cl) (367.2 mg/233.2 μL, 1.733 mmol) and 4-dimethylaminopyridine (DMAP) (3.5 mg, 28.9 μmol) at 0° C. After being stirred at the same temperature for 1 h, the reaction was quenched with aqueous HCl (1 M, 4 mL). The water layer was extracted with ethyl acetate (10 mL×4). The combined organic layers were washed with saturated NaHCO$_3$, brine, dried with MgSO$_4$ and concentrated in vacuo. The residue was purified by silica gel column chromatography (4.5% ethyl acetate in hexane) to give P (426.4 mg, 100%) [Kinnaird, J. W. A.; Ng, P. Y.; Kubota, K.; Wang, X.; Leighton, J. L. *J. Am. Chem. Soc.* 2002, 124, 7920-7921]. $^1$H NMR (400 MHz, CDCl$_3$): δ 7.29 (d, J=8.8 Hz, 2H), 6.86 (d, J=8.4 Hz, 2H), 5.80-5.71 (m, 1H), 5.14-5.07 (m, 2H), 4.91-4.86 (m, 2H), 4.78 (d, J=11.6 Hz, 1H), 4.58 (d, J=10.8 Hz, 1H), 4.51 (d, J=10.4 Hz, 1H), 4.50 (d, J=12 Hz, 1H), 3.79 (s, 3H), 3.07 (dd, J=9.4, 2.4 Hz, 1H), 2.51-2.46 (m, 1H), 1.91 (ddd, J=14.2, 11.3, 2.4 Hz, 1H), 1.79 (br m, 1H), 1.48 (ddd, J=14.3, 9.4, 3.9 Hz, 1H), 1.36 (ddd, J=14.2, 9.7, 2.5, 1H), 1.18 (ddd, J=14.3, 9.4, 2.1 Hz, 1H), 1.08 (d, J=6.8 Hz, 3H), 1.00 (d, J=6.8 Hz, 3H), 0.93 (s, 9H) ppm. $^{13}$C NMR (100 MHz, CDCl$_3$): δ 159.0, 154.3, 139.0, 131.6, 129.0, 116.5, 113.8, 94.8, 85.2, 80.8, 77.4, 76.6, 74.6, 55.4, 42.8, 39.8, 37.7, 36.2, 26.6, 26.4, 21.0, 15.8 ppm.

Pyrrolidine-1,2-dicarboxylic acid-(2S)-2-[(3R,4S,6S,8S)-8-tert-butyl-4-(2,2,2-trichloroethoxy-carbonyloxy)-3,6-dimethyloct-1-en-8-yl]ester 1-(9H-fluoren-9-ylmethyl)ester (R) (from P) (81%)

To a solution of P (0.806 mmol) in the mixture of CH$_2$Cl$_2$ (5.0 mL) and H$_2$O (0.5 mL) was added 2,3-dichloro-5,6-dibenzoquinone (DDQ) (220 mg, 0.968 mmol) at 0° C. The reaction mixture was stirred at the same temperature for 1 h, quenched with saturated aqueous NaHCO$_3$ (10 mL) and filtered in vacuo. The organic layer was separated and water layer was extracted with CH$_2$Cl$_2$ (30 mL×3). The organic phases were combined and washed with brine (20 mL×2), dried with anhydrous MgSO$_4$, filtered and concentrated in vacuo. This residue was used for the next reaction without further purification.

To the suspended solution of Fmoc-Pro-OH (549.5 mg, 1.629 mmol) in toluene (5.0 mL) were added N,N-diisopropylethylamine (DIEA) (435 μL, 2.5 mmol), 2,4,6-trichlorobenzoyl chloride (390 μL, 2.5 mmol) at room temperature under argon, and stirred at the same temperature for 30 min. Then the crude alcohol in toluene (3.0 mL) and DMAP (350 mg, 2.862 mmol) were added to the above mixture at 10° C. After being stirred at room temperature for 3 h, the reaction mixture was quenched and extracted with diethyl ether (10 mL×3). The combined organic layer was washed with saturated NH$_4$Cl (15 mL×2), saturated NaHCO$_3$ (15 mL×2), brine (15 mL), dried over MgSO$_4$ and concentrated in vacuo. The residue was purified by silica gel column chromatography (eluted by 10% ethyl acetate in hexane) to give ester R [Kinnaird, J. W. A.; Ng, P. Y.; Kubota, K.; Wang, X.; Leighton, J. L. *J. Am. Chem. Soc.* 2002, 124, 7920-7921]. $^1$H NMR (400 MHz, CDCl$_3$, mixture of rotamers): δ 7.78-7.72 (m, 2H), 7.67-7.59 (m, 2H), 7.42-7.38 (m, 2H), 7.34-7.29 (m, 2H), 5.77-5.66 (m, 1H), 5.11-5.02 (m, 2H), 4.86-4.69 (m, 4H), 4.51 (dd, J=8.4, 2.4 Hz, 0.5H), 4.46 (dd, J=8.4, 2.4 Hz, 0.5H), 4.44-4.11 (m, 3H), 3.67-3.49 (m, 2H), 2.49 (m, 0.5H), 2.42 (m, 0.5H), 2.35-2.07 (m, 2H), 2.04-1.93 (m, 2H), 1.86-1.80 (m, 1H), 1.60-1.34 (m, 3H), 1.26 (ddd, J=14.2, 10.2, 2.8 Hz, 0.5H), 1.12 (ddd, J=13.2, 10.4, 2.1 Hz, 0.5H), 1.04 (d, J=7.2 Hz, 1.5H), 1.03 (d, J=6.8 Hz, 1.5H), 0.96 (d, J=6.4 Hz, 1.5H), 0.88 (s, 4.5H), 0.87 (s, 4.5H), 0.74 (d, J=6.4 Hz, 1.5H) ppm. $^{13}$C NMR (100 MHz, CDCl$_3$, mixture of rotamers): δ 172.6, 1724, 154.8, 154.4, 154.3, 154.1, 144.3, 144.0, 143.9, 141.4, 141.4, 141.3, 141.3, 139.0, 138.9, 127.8, 127.8, 127.2, 127.1, 127.1, 127.1, 125.5, 125.4, 125.3, 125.2, 120.1, 120.0, 116.4, 80.6, 80.4, 79.6, 79.4, 76.7, 67.9, 67.5, 59.9, 59.5, 47.3, 47.3, 47.1, 46.5, 42.7, 42.5, 38.0, 37.8, 37.2, 37.0, 35.0, 34.8, 31.4, 30.1, 26.6, 26.5, 25.9, 25.9, 24.5, 23.5, 20.4, 20.4, 15.6, 15.6 ppm.

Pyrrolidine-1,2-dicarboxylic acid (2S)-2-[(1S,3S,5S,6S)-1-tert-butyl-6-carboxy-5-(2,2,2-trichloroethoxy-carbonyloxy)-3-methylhept-1-yl]ester 1-(9H-fluoren-9-ylmethyl)ester (T) (from R) (83%)

To the solution of R (0.646 mmol) in DMF (6.0 ml) were added Oxone (1.588 g, 2.583 mmol), NaHCO$_3$ (217.0 mg, 2.583 mmol) and OsO$_4$ (2.5% solution in tert-BuOH) (81 μL, 6.5 μmol) at room temperature. After being stirred at the same temperature for 15 h, the reaction mixture was diluted with water (4 mL) and tert-BuOH (7.5 mL), and then NaIO$_4$ (276.3 mg, 1.292 mmol) was added. The reaction mixture was stirred at room temperature for an additional 5 h and poured into aqueous 1M HCl and CH$_2$Cl$_2$ (25 mL). The water layer was extracted with CH$_2$Cl$_2$ (50 mL×3). The combined CH$_2$Cl$_2$ layers were washed with 10 wt % Na$_2$S$_2$O$_3$ (50 mL×3), brine (50 mL×1), dried over MgSO$_4$ and concentrated in vacuo. The residue was purified by silica gel column chromatography eluting with 17-25% ethyl acetate in hexane to give product T as a white solid. $^1$H NMR (400 MHz, CDCl$_3$, mixture of rotamers): δ 7.77-7.74 (m, 2H), 7.66-7.59 (m, 2H), 7.41-7.38 (m, 2H), 7.34-7.29 (m, 2H), 5.18-5.09 (m, 1H), 4.88-4.66 (m, 3H), 4.52-4.15 (m, 4H), 3.67-3.47 (m, 2H), 2.94 (dq, J=7.2, 7.2 Hz, 0.6H), 2.86 (dq, J=7.2, 7.2 Hz, 0.4H), 2.36-2.07 (m, 2H), 2.00-1.82 (m, 3H), 1.62 (m, 0.6H), 1.54-1.49 (m, 1.4H), 1.43-1.22 (m, 2H), 1.21 (d, J=7.2 Hz, 3H), 0.99 (d, J=6.8 Hz, 1.6H), 0.88 (s, 1.5H), 0.86 (s, 1.5H), 0.76 (d, J=6.4 Hz, 1.4H) ppm. $^{13}$C NMR (100 MHz, CDCl$_3$, mixture of rotamers): δ 178.5, 178.1, 172.7, 172.3, 154.9, 154.5, 153.8, 153.7, 144.2, 144.1, 143.9, 143.8, 141.3, 141.3, 141.3, 127.8, 127.2, 127.1, 127.1, 125.5, 125.4, 125.2, 125.2, 120.0, 120.0, 120.0, 79.6, 79.2, 77.9, 77.4, 76.9, 76.8, 67.9, 67.6, 59.8, 59.5, 47.3, 47.1, 46.5, 43.6, 43.2, 38.0, 37.6, 36.7, 36.3, 35.0, 34.7, 31.3, 30.1, 29.8, 26.2, 26.1, 25.9, 24.4, 23.4, 20.4, 20.2, 12.2, 12.1 ppm.

Example 3: Preparation of Carboxylic Acid U (4S,6S,8S)-8-(4-methoxybenzyloxy)-6,9,9-tetramethyldec-1-en-4-ol (O)

To the solution of K (203.3 mg, 0.696 mmol) in $CH_2Cl_2$ (7 mL) was added (S,S)-M (772.1 mg, 1.392 mmol) and $Sc(OTf)_3$ (28.5 mg, 0.058 mmol) at 0° C. This mixture was stirred vigorously at the same temperature for 2.0 h, then it was treated with 12 mL $Et_2O$ and 12 mL 1N aq. HCl. Afterwards the quenched mixture was stirred at room temperature for 30 min, filtered to remove the precipitate, extracted with $Et_2O$ (15 mL×3), washed with saturated $NaHCO_3$ (20 mL×2) and brine (20 mL), dried with anhydrous $MgSO_4$, evaporated in vacuo and purified by column chromatography (eluted by 4.2% ethyl acetate in hexane) to give product O (197.6 mg, 85%) as a colorless oil. $[\alpha]^{20}_D$ −57.8 (c 0.32, $CH_2Cl_2$). $^1H$ NMR (400 MHz, $CDCl_3$): δ 7.30 (d, J=8.4 Hz, 2H), 6.86 (d, J=8.4 Hz, 2H), 5.89-5.79 (m, 1H), 5.17-5.13 (m, 2H), 4.63 (d, J=10.4 Hz, 1H), 4.52 (d, J=10.4, 1H), 3.79 (s, 3H), 3.79-3.74 (m, 1H), 3.11 (dd, J=9.2, 2.4 Hz, 1H), 2.30-2.24 (m, 1H), 2.21-2.14 (m, 1H), 2.00-1.90 (br m, 1H), 1.65 (ddd, J=13.6, 10.6, 2.8 Hz, 1H), 1.46 (ddd, J=14.0, 8.8, 4.0 Hz, 1H), 1.35 (ddd, J=14.0, 9.2, 2.4 Hz, 1H), 1.09 (ddd, J=13.6, 10.4, 2.0 Hz, 1H), 0.97 (d, J=6.4 Hz, 3H), 0.94 (s, 9H) ppm. $^{13}C$ NMR (100 MHz, $CDCl_3$): δ 159.0, 135.0, 131.7, 129.2, 118.1, 113.7, 85.3, 74.3, 68.4, 55.3, 43.5, 43.3, 39.8, 36.2, 26.6, 21.1 ppm. HRMS (ESI) m/z calcd for $C_{21}H_{34}O_3Na$ (M+Na)$^+$ 357.2400, found 357.2409.

tert-Butyl [(4S,6S,8S)-8-(4-methoxybenzyloxy)-6,9,9-tetramethyldec-1-en-4-yloxy]dimethyl-silane (Q)

To the solution of O (178.6 mg, 0.534 mmol) in $CH_2Cl_2$ (8 ml) were added 2,6-lutidine (310 μL, 2.672 mmol) and tert-butyldimethylsilyl trifluoromethanesulfonate (TBSOTf) (368.2 μL, 1.603 mmol) at 0° C. under Ar. After being stirred at the same temperature for 1.5 h, the reaction was quenched with MeOH (5 mL) and saturated aq. $NH_4C$ (7 mL), extracted with ethyl acetate (10 mL×4), washed with brine (10 mL×2), dried with anhydrous $MgSO_4$, evaporated in vacuo and purified by column chromatography (eluted by 3.6% ethyl acetate in hexane) to give product Q (224.4 mg, 94%) as a colorless oil. $[\alpha]^{20}_D$ −49.0 (c 0.31, $CH_2Cl_2$). $^1H$ NMR (400 MHz, $CDCl_3$): δ 7.28 (d, J=8.4 Hz, 2H), 6.86 (d, J=8.8 Hz, 2H), 5.86-5.76 (m, 1H), 5.07-5.03 (m, 2H), 4.65 (d, J=10.8 Hz, 1H), 4.45 (d, J=10.8 Hz, 1H), 3.86-3.80 (m, 1H), 3.80 (s, 3H), 3.08 (dd, J=7.2, 3.6 Hz, 1H), 2.31-2.20 (m, 2H), 1.87 (br m, 1H), 1.66 (ddd, J=13.2, 9.2, 2.8 Hz, 1H), 1.46-1.34 (m, 2H), 1.06 (d, J=6.8 Hz, 3H), 0.91 (s, 9H), 0.86 (s, 9H) ppm. $^{13}C$ NMR (100 MHz, $CDCl_3$): δ 159.0, 135.2, 131.9, 128.9, 117.0, 113.7, 85.6, 73.9, 69.8, 55.4, 43.9, 43.4, 40.5, 36.2, 26.8, 26.6, 26.1, 21.0, 18.2, −4.1, −4.3 ppm. HRMS (ESI) m/z calcd for $C_{27}H_{48}O_3SiNa$ (M+Na)$^+$ 471.3265, found 471.3264.

Pyrrolidine-1,2-dicarboxylic acid-(2S)-2-[(4S,6S,8S)-8-tert-butyl-4-(tert-butyldimethylsilyl-oxy)-6-dimethyloct-1-en-8-yl]ester 1-(9H-fluoren-9-ylmethyl)ester (S) (from Q) (100%)

To a solution of Q (0.806 mmol) in the mixture of $CH_2Cl_2$ (5.0 mL) and $H_2O$ (0.5 mL) was added 2,3-dichloro-5,6-dibenzoquinone (DDQ) (220 mg, 0.968 mmol) at 0° C. The reaction mixture was stirred at the same temperature for 1 h, quenched with saturated aqueous $NaHCO_3$ (10 mL) and filtered in vacuo. The organic layer was separated and the water layer was extracted with $CH_2Cl_2$ (30 mL×3). The organic phases were combined and washed with brine (20 mL×2), dried with anhydrous $MgSO_4$, filtered and concentrated in vacuo. This residue was used for the next reaction without further purification.

To the suspended solution of Fmoc-Pro-OH (549.5 mg, 1.629 mmol) in toluene (5.0 mL) was added N,N-diisopropylethylamine (DIEA) (435 μL, 2.5 mmol), 2,4,6-trichlorobenzoyl chloride (390 μL, 2.5 mmol) at room temperature under argon, and stirred at the same temperature for 30 min. Then the crude alcohol in toluene (3.0 mL) and DMAP (350 mg, 2.862 mmol) were added to the above mixture at 10° C. After being stirred at room temperature for 3 h, the reaction mixture was quenched and extracted with diethyl ether (10 mL×3). The combined organic layers were washed with saturated $NH_4C$ (15 mL×2), saturated $NaHCO_3$ (15 mL×2), brine (15 mL), dried over $MgSO_4$ and concentrated in vacuo. The residue was purified by silica gel column chromatography (eluted by 10% ethyl acetate in hexane) to give ester S. $[\alpha]^{20}_D$ −66.4 (c 0.11, $CH_2Cl_2$). $^1H$ NMR (400 MHz, $CDCl_3$, mixture of rotamers): δ 7.78-7.75 (m, 2H), 7.67-7.55 (m, 2H), 7.42-7.38 (m, 2H), 7.33-7.30 (m, 2H), 5.85-5.71 (m, 1H), 5.05-4.99 (m, 2H), 4.80 (dd, J=8.4, 2.0 Hz, 1H), 4.53-4.40 (m, 2H), 4.35-4.17 (m, 2H), 3.81-3.71 (m, 1H), 3.70-3.62 (m, 1H), 3.60-3.50 (m, 1H), 2.32-2.15 (m, 3H), 2.14-1.93 (m, 3H), 1.62-1.49 (m, 3H), 1.39-1.30 (m, 1H), 1.20-1.03 (m, 1H), 0.95 (d, J=6.4 Hz, 2H), 0.87 (s, 9H), 0.87 (s, 9H), 0.82 (d, J=6.4 Hz, 1H), 0.05-0.02 (m, 6H) ppm. $^{13}C$ NMR (100 MHz, $CDCl_3$, mixture of rotamers): δ 172.2, 172.1, 154.7, 154.5, 144.3, 144.2, 144.1, 143.8, 141.4, 141.4, 141.3, 135.6, 135.3, 127.8, 127.8, 127.2, 127.1, 127.1, 125.5, 125.3, 125.2, 120.0, 116.9, 116.8, 80.6, 80.4, 77.5, 77.2, 76.8, 70.2, 70.0, 67.8, 67.5, 59.8, 59.6, 47.4, 47.0, 46.4, 44.2, 44.0, 42.6, 42.5, 39.3, 39.1, 35.2, 35.1, 31.3, 30.1, 27.1, 27.0, 26.1, 26.0, 26.0, 24.4, 23.4, 20.9, 20.6, 18.2 ppm. HRMS (ESI) m/z calcd for $C_{39}H_{57}NO_5SiNa$ (M+Na)$^+$ 670.3898, found 670.3920.

Pyrrolidine-1,2-dicarboxylic acid (2S)-2-[(1S,3S,5S)-1-tert-butyl-6-carboxy-5-hydroxy-3-methylhept-1-yl]ester 1-(9H-fluoren-9-ylmethyl)ester (U) (from S)

To the solution of S (0.646 mmol) in DMF (6.0 ml) were added Oxone (1.588 g, 2.583 mmol), $NaHCO_3$ (217.0 mg, 2.583 mmol) and $OsO_4$ (2.5% solution in tert-BuOH) (81 μL, 6.5 μmol) at room temperature. After being stirred at the same temperature for 15 h, the reaction mixture was diluted with water (4 mL) and tert-BuOH (7.5 mL), and then $NaIO_4$ (276.3 mg, 1.292 mmol) was added. The reaction mixture was stirred at room temperature for an additional 5 h and poured into aqueous HCl (0.5M to pH 1; 25 mL) and $CH_2Cl_2$ (25 mL). The water layer was extracted with $CH_2Cl_2$ (50 mL×3). The combined $CH_2Cl_2$ layers were washed with 10 wt % $Na_2S_2O_3$ (50 mL×3), brine (50 mL×1), dried over $MgSO_4$ and concentrated in vacuo. The residue was purified by silica gel column chromatography eluting with 2.5-10% MeOH in $CH_2Cl_2$ to give product U as a white solid. $[\alpha]^{20}_D$ −46.2 (c 0.119, $CH_2Cl_2$). $^1H$ NMR (400 MHz, $CDCl_3$, mixture of rotamers, major): δ 7.75 (d, J=7.6 Hz, 2H), 7.62-7.55 (m, 2H), 7.39 (dd, J=7.6, 7.4 Hz, 2H), 7.33-7.29 (m, 2H), 5.40 (br, 1H), 4.91 (d, J=10.8 Hz, 1H), 4.42-4.38 (m, 1H), 4.34-4.29 (m, 1H), 4.12-4.06 (m, 1H), 3.68-3.62

(m, 1H), 3.52-3.47 (m, 1H), 2.44-2.43 (m, 2H), 2.33-2.23 (m, 1H), 2.08-1.91 (m, 3H), 1.86-1.80 (m, 1H), 1.75 (dd, J=13.6, 2.4 Hz, 1H), 1.66 (dd, J=14.4, 2.0 Hz, 1H), 1.33-1.26 (m, 1H), 1.04-0.98 (m, 1H), 0.98 (d, J=6.4 Hz, 3H), 0.89 (s, 9H) ppm. $^{13}$C NMR (100 MHz, CDCl$_3$, mixture of rotamers, major): δ 174.6, 172.4, 155.4, 144.0, 143.7, 127.9, 127.8, 127.3, 127.2, 125.3, 125.2, 120.1, 120.1, 78.5, 68.0, 66.0, 59.6, 47.2, 46.7, 42.7, 41.7, 37.2, 34.8, 30.0, 26.1, 25.0, 24.6, 20.6 ppm. HRMS (ESI) m/z calcd for C$_{32}$H$_{41}$NO$_7$Na (M+Na)$^+$ 574.2775, found 574.2970.

Example 4: Preparation of Carboxylic Acid AB

Methyl (3S,5S,7S)-3-hydroxy-7-(4-methoxybenzyloxy)-2,2,5,8,8-pentamethylnonanoate (W)

To the solution of N-tosyl-D-Val-OH (145.6 mg, 0.537 mmol) in CH$_2$Cl$_2$ (7 mL) at 0° C. under argon was added the solution of BH$_3$ in THF (M, 537 μL, 0.537 mmol) dropwise. The resulting mixture was stirred at room temperature for 20 min and then cooled to −78° C. Aldehyde K (157.0 mg, 0.537 mmol), methyl trimethylsilyl dimethylketene acetal (120.0 μL, 0.591 mmol) were added successively to the above mixture at −78° C. After being stirred at −78° C. for 3 h, the reaction mixture was quenched with buffer (pH 7; 8 mL) and then it was warmed to room temperature and another 5 mL of buffer (pH 7) was added. The quenched reaction mixture was extracted with Et$_2$O (25 mL×3), washed with saturated NaHCO$_3$ (15 mL×2) and brine (15 mL×2), dried with anhydrous MgSO$_4$ and purified by column chromatography (eluted by 8.5% ethyl acetate in hexane) to give product W as a colorless oil (171.5 mg, 81%). [α]$^{20}_D$ −55.8 (c 0.12, CH$_2$Cl$_2$). $^1$H NMR (400 MHz, CDCl$_3$): δ 7.29 (d, J=8.4 Hz, 2H), 6.85 (d, J=8.4 Hz, 2H), 4.63 (d, J=10.4 Hz, 1H), 4.50 (d, J=10.4 Hz, 1H), 3.77 (s, 3H), 3.74 (br m, 1H), 3.69 (s, 3H), 3.09 (dd, J=9.2, 2.4 Hz, 1H), 2.47 (br, 1H), 2.03-1.95 (br m, 1H), 1.58-1.45 (m, 2H), 1.37-1.30 (m, 1H), 1.18 (s, 6H), 1.03-1.00 (m, 1H), 0.96 (d, J=6.4 Hz, 3H), 0.93 (s, 9H) ppm. $^{13}$C NMR (100 MHz, CDCl$_3$): δ 178.3, 159.0, 131.6, 129.2, 113.7, 85.2, 74.4, 74.2, 55.3, 51.9, 47.3, 39.7, 38.2, 36.2, 26.8, 26.6, 22.1, 20.9, 20.6 ppm. HRMS (ESI) m/z calcd for C$_{23}$H$_{38}$O$_5$Na (M+Na)$^+$ 417.2611, found 417.2628.

(3S,5S,7S)-3-Hydroxy-7-(4-methoxybenzyloxy)-2,2,5,8,8-pentamethylnonanoic acid (X)

To the solution of W (223.8 mg, 0.568 mmol) in the mixture of THF-MeOH—H$_2$O (7 mL-3.5 mL-0.7 mL) was added aq. LiOH (119.1 mg in 2.8 mL H$_2$O, 2.838 mmol). After being stirred at room temperature for 5 h, the reaction mixture was diluted with 10 mL water, neutralized by addition of aq HCl (2M) to pH 2, extracted with ethyl acetate (10 mL×4), washed with brine (10 mL×2), dried with anhydrous MgSO$_4$ and purified by column chromatography (eluted by 8.5-17% acetone in hexane) to give X (225 mg, 100%) as a white solid. [α]$^{20}_D$ −52.3 (c 0.26, CH$_2$Cl$_2$). $^1$H NMR (400 MHz, CDCl$_3$): δ 7.30 (d, J=8.4 Hz, 2H), 6.86 (d, J=8.4 Hz, 2H), 4.63 (d, J=10.4 Hz, 1H), 4.53 (d, J=10.4 Hz, 1H), 3.80 (d, J=13.0, 1H), 3.78 (s, 3H), 3.13 (dd, J=8.0, 2.0 Hz, 1H), 1.80 (br m, 1H), 1.62-1.49 (m, 2H), 1.40-1.34 (m, 1H), 1.21 (s, 3H), 1.19 (s, 3H), 1.09 (dd, J=12.4, 12.4), 0.98 (d, J=6.4 Hz, 3H), 0.95 (s, 9H) ppm. $^{13}$C NMR (100 MHz, CDCl$_3$): δ 182.9, 159.0, 131.4, 129.3, 113.7, 85.2, 74.3, 74.3, 55.3, 47.1, 39.4, 37.9, 36.2, 26.8, 26.6, 22.3, 20.8, 20.2 ppm. HRMS (ESI) m/z calcd for C$_{22}$H$_{36}$O$_5$Na (M+Na)$^+$ 403.2455, found 403.2472.

Allyl (3S,5S,7S)-3-hydroxy-7-(4-methoxybenzyloxy)-2,2,5,8,8-pentamethylnonanoate (Y)

To the solution of compound X (222.4 mg, 0.585 mmol) in dimethyl sulfoxide (DMSO) (5.0 mL) were added K$_2$CO$_3$ (242.5 mg, 1.754 mmol) and allyl bromide (AllyBr) (99 μL, 1.170 mmol) at room temperature. After being stirred at the same temperature overnight, the reaction was quenched with water (10 mL) and extracted with ethyl acetate (20 mL×4). The combined organic layers were washed with brine (10 mL×5), filtered, concentrated in vacuo and purified by silica gel column chromatography (eluted by 6.5% ethyl acetate in hexane) to give product Y (228.6 mg, 93%) as a colorless oil. [α]$^{20}_D$ −56.0 (c 0.175, CH$_2$Cl$_2$). $^1$H NMR (400 MHz, CDCl$_3$): δ 7.30 (d, J=8.4 Hz, 2H), 6.85 (d, J=8.4 Hz, 2H), 5.96-5.86 (m, 1H), 5.35-5.22 (m, 2H), 4.64 (d, J=10.4 Hz, 1H), 4.60 (d, J=5.6 Hz, 2H), 4.50 (d, J=10.4 Hz, 1H), 3.78 (br m, 1H), 3.77 (s, 3H), 3.10 (dd, J=8.0, 2.0 Hz, 1H), 2.54 (br, 1H), 2.0 (br m, 1H), 1.61-1.55 (m, H), 1.49 (ddd, J=17.6, 9.6, 4.0 Hz, 1H), 1.37-1.31 (m, 1H), 1.21 (s, 6H), 1.05-0.98 (m, 1H), 0.97 (d, J=6.8 Hz, 3H), 0.94 (s, 9H) ppm. 13C NMR (100 MHz, CDCl$_3$): δ 177.3, 158.9, 132.0, 131.5, 129.1, 118.2, 113.6, 85.0, 74.3, 74.2, 65.2, 55.2, 47.3, 39.7, 38.1, 36.1, 26.6, 26.5, 21.9, 20.9, 20.7 ppm. HRMS (ESI) m/z calcd for C$_{25}$H$_{40}$O$_5$Na (M+Na)$^+$ 443.2768, found 443.2769.

Allyl (3S,5S,7S)-3-(2,2,2-trichloroethoxycarbonyloxy)-7-(4-methoxybenzyloxy)-2,2,5,8,8-pentamethylnonanoate (Z)

To the solution of Y (220.0 mg, 0.523 mmol) in CH$_2$Cl$_2$ (5.0 ml) at 0° C. under Ar were added 4-dimethylaminopyridine (DMAP) (1.3 mg, 10.5 μmol), pyridine (423 μL, 5.234 mmol) and 2,2,2-trichloroethoxylcarbonyl chloride (Troc-Cl) (554.5 mg/360.0 μL, 2.617 mmol). After being stirred at 0° C. for 10 min and at room temperature for 1 h, the reaction was quenched with water (10 mL) and extracted with ethyl acetate (15 mL×4). The combined organic layers were washed with saturated NaHCO$_3$ and brine, dried with MgSO$_4$, concentrated in vacuo and purified by silica gel column chromatography (2.5-10-15% ethyl acetate in hexane) to give Z (295.1 mg, 95.0%). [α]$^{20}_D$ −7.6 (c 0.37, CH$_2$Cl$_2$). $^1$H NMR (400 MHz, CDCl$_3$): δ 7.27 (d, J=8.4 Hz, 2H), 6.86 (d, J=8.4 Hz, 2H), 5.96-5.86 (m, 1H), 5.37-5.23 (m, 3H), 4.78 (d, J=12.0 Hz, 1H), 4.59 (d, J=5.6 Hz, 2H), 4.55 (d, J=10.8 Hz, 1H), 4.49 (d, J=10.8 Hz, 1H), 4.30 (d, J=12.0 Hz, 1H), 3.78 (s, 3H), 3.05 (dd, J=9.6, 2.0 Hz, 1H), 1.99-1.93 (m, 1H), 1.75 (br m, 1H), 1.50 (ddd, J=17.2, 9.2, 3.0 Hz, 1H), 1.35-1.29 (m, 1H), 1.27 (s, 3H), 1.25 (s, 3H), 1.08-1.01 (m, 4H), 0.92 (s, 9H) ppm. $^{13}$C NMR (100 MHz, CDCl$_3$): δ 174.8, 159.0, 154.4, 131.9, 131.5, 128.7, 118.6, 113.7, 94.6, 85.0, 80.9, 76.6, 74.4, 65.6, 55.3, 47.0, 39.8, 36.8, 36.1, 26.5, 26.4, 22.4, 20.8, 19.7 ppm. HRMS (ESI) m/z calcd for C$_{28}$H$_{41}$C$_{13}$O$_7$Na (M+Na)$^+$ 617.1810, found 617.1832.

Pyrrolidine-1,2-dicarboxylic acid (2S)-2-[(1S,3S,5S)-1-tert-butyl-6-allyloxycarbonyl-5-(2,2,2-trichloroethoxycarbonyloxy)-3,6-dimethylhept-1-yl]ester 1-(9H-fluoren-9-ylmethyl)ester (AA)

To a solution of Z (291.5 mg, 0.491 mmol) in a mixture of CH$_2$Cl$_2$ (5.0 ml) and H$_2$O (0.5 mL) was added 2,3-dichloro-5,6-dibenzoquinone (DDQ) (133.6 mg, 0.589 mmol) at 0° C. The reaction mixture was stirred at the same temperature for 1 h, quenched with saturated aqueous NaHCO$_3$ (6 mL) and filtered in vacuo. The organic layer was separated and the water layer was extracted with CH$_2$Cl$_2$ (15 mL×4). The organic phases were combined and washed with brine (3×15 mL), dried with anhydrous MgSO$_4$, filtered and concentrated in vacuo. This residue was used for the next reaction without further purification.

To the suspended solution of Fmoc-Pro-OH (334.3 mg, 0.991 mmol) in toluene (3.0 ml) was added N,N-diisopropylethylamine (DIEA) (0.26 mL, 1.49 mmol), 2,4,6-trichlorobenzoyl chloride (233 µL, 1.491 mmol) at room temperature under argon, and stirred at the same temperature for 10 min. Then the crude alcohol in toluene (1.5 mL) and DMAP (212.8 mg, 1.742 mmol) were added to the above mixture. After being stirred at room temperature overnight, the reaction mixture was quenched with water and extracted with diethyl ether (20 mL×4). The combined organic layers were washed with saturated NH$_4$Cl (20 mL×2), saturated NaHCO$_3$ (20 mL×2), brine (20 mL), dried over MgSO$_4$ and concentrated in vacuo. The residue was purified by silica gel column chromatography (eluted by 10% ethyl acetate in hexane) to give ester AA (360.8 mg, 90.4%) as a colorless oil. [α]$^{20}_D$ −58.9 (c 0.124, CH$_2$Cl$_2$). $^1$H NMR (400 MHz, CDCl$_3$, mixture of rotamers): δ 7.77-7.75 (m, 2H), 7.67-7.62 (m, 2H), 7.40 (dd, J=7.4, 7.2 Hz, 2H), 7.34-7.29 (m, 2H), 6.00-5.79 (m, 1H), 5.34-5.12 (m, 3H), 4.97 (d, J=12.0 Hz, 0.6H), 4.87 (d, J=12.0 Hz, 0.4H), 4.78 (d, J=10.0 Hz, 1H), 4.69 (d, J=12.0 Hz, 0.4H), 4.64 (d, J=12.0 Hz, 0.6H), 4.59-4.16 (m, 6H), 3.67-3.61 (m, 1H), 3.59-3.48 (m, 1H), 2.38-2.28 (m, 0.6H), 2.24-2.16 (m, 0.4H), 2.15-2.06 (m, 1H), 2.04-1.93 (m, 2H), 1.92-1.80 (m, 1H), 1.55-1.48 (m, 1H), 1.46-1.42 (m, 1H), 1.38-1.29 (m, 1H), 1.25-1.19 (m, 6H), 1.15-1.07 (m, 0.6H), 1.00-0.96 (m, 1.6H), 0.89 (s, 5.4H), 0.86 (s, 3.6H), 0.67 (d, J=6.4 Hz, 1.8H) ppm. $^{13}$C NMR (100 MHz, CDCl$_3$, mixture of rotamers): δ 175.0, 175.0, 172.9, 172.4, 154.7, 154.5, 154.3, 154.2, 144.4, 144.3, 144.0, 143.9, 141.4, 141.4, 141.3, 141.3, 132.0, 131.9, 127.8, 127.2, 127.1, 125.5, 125.4, 125.3, 125.2, 120.0, 120.0, 118.6, 94.9, 94.8, 80.8, 80.6, 79.8, 79.5, 77.1, 76.9, 68.0, 67.5, 65.7, 65.6, 59.9, 59.4, 47.3, 47.3, 47.2, 47.1, 46.5, 38.2, 38.0, 37.3, 36.8, 34.9, 34.8, 34.7, 31.7, 31.4, 30.1, 26.9, 26.7, 25.9, 25.9, 25.4, 23.5, 22.8, 22.0, 22.0, 20.5, 20.4, 19.8, 19.7, 14.2 ppm. HRMS (ESI) m/z calcd for C$_{40}$H$_{50}$Cl$_3$NO$_9$Na (M+Na)$^+$ 816.2443, found 816.2420.

Pyrrolidine-1,2-dicarboxylic acid (2S)-2-[(1S,3S, 5S)-1-tert-butyl-6-carboxy-5-(2,2,2-trichloroethoxycarbonyloxy)-3,6-dimethylhept-1-yl]ester 1-(9H-fluoren-9-ylmethyl)ester (AB)

To a solution of AA (349.3 mg, 0.440 mmol) in THF (8 ml) were added Pd(PPh$_3$)$_4$ (76.3 mg, 0.066 mmol) and N-methyl aniline (144.3 µL, 1.321 mmol) at room temperature under argon. This reaction was protected with aluminum foil. After being stirred at the room temperature for 1 h, the reaction mixture was concentrated in vacuo and purified by column chromatography (eluted by acetone/hexane 1:3) to give acid AB (354.1 mg, 95%) as a pale yellow solid. [α]$^{20}_D$ −51.1 (c 0.131, CH$_2$Cl$_2$). $^1$H NMR (400 MHz, CDCl$_3$, mixture of rotamers): δ 9.90 (br, 1H), 7.77-7.74 (m, 2H), 7.68-7.63 (m, 2H), 7.42-7.38 (m, 2H), 7.34-7.29 (m, 2H), 5.23 (d, J=10.4 Hz, 0.4H), 5.13 (d, J=10.4 Hz, 0.6H), 5.01 (d, J=12.0 Hz, 0.6H), 4.90 (d, J=12.0 Hz, 0.4H), 4.85-4.79 (m, 1H), 4.70 (d, J=12.0 Hz, 0.4H), 4.63 (d, J=12.0 Hz, 0.6H), 4.52-4.17 (m, 4H), 3.67-3.48 (m, 1H), 2.37-2.27 (m, 0.6H), 2.24-2.19 (m, 0.4H), 2.16-2.10 (m, 1H), 2.01-1.83 (m, 3H), 1.78-1.69 (m, 0.4H), 1.62-1.49 (M, 1.6H), 1.43-1.35 (m, 1H), 1.31-1.20 (m, 6H), 1.09-1.00 (m, 1H), 1.01 (d, J=6.4 Hz, 1.2H), 0.94 (s, 5.4H), 0.87 (s, 3.6H), 0.69 (d, J=6.4 Hz, 1.8H) ppm. $^{13}$C NMR (100 MHz, CDCl$_3$, mixture of rotamers): δ 181.1, 180.7, 172.8, 172.3, 154.8, 154.4, 154.2, 144.3, 144.1, 143.9, 143.7, 141.3, 141.3, 141.2, 141.2, 135.1, 135.0, 135.0, 130.6, 128.1, 128.1, 128.0, 127.7, 127.1, 127.1, 127.0, 125.5, 125.3, 125.2, 125.1, 120.0, 119.9, 94.9, 94.8, 80.5, 80.3, 79.8, 79.4, 77.0, 76.8, 68.0, 67.6, 59.8, 59.3, 47.2, 47.1, 46.9, 46.4, 38.1, 37.5, 37.1, 36.7, 34.9, 34.7, 34.6, 34.5, 31.6, 31.3, 30.0, 29.1, 29.1, 26.7, 26.5, 25.9, 25.3, 24.3, 23.5, 22.7, 22.2, 21.9, 20.8, 20.4, 19.9, 19.6, 19.4, 18.8, 14.2, 11.5 ppm. HRMS (ESI) m/z calcd for C$_{37}$H$_{46}$Cl$_3$NO$_9$Na (M+Na)$^+$ 776.2130, found 776.2149.

Example 5: Preparation of Allyl Ester AM (S)—N-methyl-N-methoxy-2-tert-butoxycarbonylamino-3-(triphenylmethylthio)propionamide (AC) (2.322 g, 85%)

To the solution of N-Boc-Cys(S-Trt)-OH (2.5 g, 5.393 mmol) in CH$_2$Cl$_2$ (25 mL) was added N,O-dimethylhydroxyamine hydrochloride (0.631 g, 6.471 mmol), N,N-diisopropylethylamine (DIEA) (2.34 mL, 13.482 mmol), EDCI-HCl (1.344 g, 7.011 mmol) and HOBt-H$_2$O (1.074 g, 7.011 mmol) at room temperature. The resulting mixture was stirred at the same temperature for 3 h, evaporated in vacuo, re-dissolved in ethyl acetate (20 mL), quenched with 1N aq. HCl (20 mL) and extracted with ethyl acetate (30 mL×3). The combined organic layers were washed with 1N aq. HCl (30 mL×2), saturated NaHCO$_3$ (30 mL×2) and brine (30 mL), dried with anhydrous MgSO$_4$, evaporated in vacuo and purified by column chromatography (eluted by ethyl acetate/hexane 1:2) to give product AC [Kinnaird, J. W. A.; Ng, P. Y.; Kubota, K.; Wang, X.; Leighton, J. L. *J. Am. Chem. Soc.* 2002, 124, 7920-7921; Rodolfo T.-A.; Tara D. N.; William A. M. *J. Org. Chem.* 2012, 77, 6271-6289].

Ethyl (S,E-)-4-tert-butoxycarbonylamino-5-(triphenylmethylthio)-penta-2-enoate (AG) (96% 2 Steps)

To the solution of Weinreb amide AC (2.505 g, 4.945 mmol) in THF (50 mL) was added LiAlH$_4$ (234.6 mg, 6.182 mmol) in one portion at 0° C. After being stirred at 0° C. for 30 min, the reaction mixture was quenched with 0.2N aq. KHSO$_4$ (30 mL) and extracted with Et$_2$O (50 mL×3). The combined organic layers were washed with 1N aq. HCl (30 mL×3), brine (30 mL×3), dried with anhydrous MgSO$_4$ and evaporated in vacuo to give the crude aldehyde AE, which was used in the next step without further purification. To the crude aldehyde AE in toluene (30 mL) was added Ph$_3$P=CHCO$_2$Et (3.101 g, 8.901 mmol) at 0° C. under Ar. After being stirred at room temperature for 3 h, the reaction mixture was concentrated in vacuo and purified by column chromatography (eluted by 12-17% ethyl acetate in hexane) to give product AG as a colorless oil [Chen, Q.-Y.; Liu, Y.; Luesch, H. *ACS Med. Chem. Lett.* 2011, 2, 861-865; Doi, T.; Numajiri, Y.; Munakata, A.; Takahashi, T. *Org. Lett.* 2006, 8, 531-534; Numajiri, Y.; Takahashi, T.; Doi, T. *Chem. Asian J.* 2009, 4, 111-125]. $^1$H NMR (400 MHz, CDCl$_3$): δ 7.41-7.40 (m, 6H), 7.31-7.28 (m, 6H), 7.24-7.21 (m, 3H), 6.69 (dd, J=15.6, 4.4 Hz, 1H), 5.81 (dd, J=15.6, 1.2 Hz, 1H), 4.62 (br, 1H), 4.27 (br, 1H), 4.17 (q, J=7.2 Hz, 2H), 2.49-2.39 (m, 2H), 1.43 (s, 9H), 1.28 (t, J=7.2 Hz, 3H) ppm. $^{13}$C NMR (100 MHz, CDCl$_3$): δ 166.1, 154.9, 146.7, 144.5, 129.6, 128.1, 127.0, 121.7, 80.0, 67.2, 60.6, 50.6, 36.4, 28.5, 14.3 ppm.

Ethyl (S)-4-tert-butoxycarbonylamino-5-(triphenylmethylthio)pentanoate (AI) (35%)

To the solution of compound AG (3.379 g, 6.532 mmol) in 95% EtOH (35 mL) was added NaBH$_4$ (247.1 mg, 6.532 mmol) at room temperature. The resulting mixture was stirred at room temperature for 30 h, and then quenched with water (50 mL) and extracted with Et$_2$O (50 mL×4). The combined organic layers were dried with anhydrous MgSO$_4$, evaporated in vacuo and purified by column chromatography (eluted with the mixture of CH$_2$Cl$_2$/hexane/acetone from 50:148:2→50:98:2→50:48:2) to give product AI (1.187 g, 35%) as a thick colorless oil [Chen, Q.-Y.; Liu, Y.; Luesch, H. ACS Med. Chem. Lett. 2011, 2, 861-865; Kinnaird, J. W. A.; Ng, P. Y.; Kubota, K.; Wang, X.; Leighton, J. L. J. Am. Chem. Soc. 2002, 124, 7920-7921; Rodolfo T.-A.; Tara D. N.; William A. M. J. Org. Chem. 2012, 77, 6271-6289]. $^1$H NMR (400 MHz, CDCl$_3$): δ 7.42-7.40 (m, 6H), 7.30-7.26 (m, 6H), 7.23-7.19 (m, 3H), 4.50 (d, J=8.0 Hz, 1H), 4.10 (q, J=7.2 Hz, 2H), 3.64 (br, 1H), 2.36-2.30 (m, 2H), 2.21 (t, J=7.6 Hz, 2H), 1.79-1.63 (m, 2H), 1.43 (s, 9H), 1.23 (t, J=7.2 Hz, 3H) ppm. $^{13}$C NMR (100 MHz, CDCl$_3$): δ 173.2, 155.3, 144.7, 129.7, 128.0, 126.8, 79.4, 66.7, 60.5, 49.6, 37.2, 31.1, 29.7, 28.5, 14.3 ppm.

Allyl (S)-4-tert-butoxycarbonylamino-5-(triphenylmethylthio)pentanoate (AM)(0.963 g, 90%)

To the solution of AI (1.045 g, 2.013 mmol) in 95% ethanol (7.5 ml) was added aq. LiOH (1M, 4.0 mL) at room temperature. After being stirred at the same temperature for 2 h, the reaction mixture was diluted with water (10 mL), acidified with 1M to 0.5 M aq. HCl to pH 4-5, and extracted with diethyl ether (20 mL×3). The combined organic layer was dried over MgSO$_4$, filtered and concentrated in vacuo to give crude acid AK, which was used in the next step without further purification. To the above crude acid AK solution in DMSO (15 mL) was added K$_2$CO$_3$ (556.5 mg, 4.027 mmol) and allyl bromide (255.5 μL, 3.020 mmol) at room temperature. After being stirred at room temperature for 5 h, the reaction was quenched with water (30 mL) and extracted with ethyl acetate (50 mL×3). The combined organic layers were washed with brine, filtered, concentrated in vacuo and the residue was purified by column chromatography on silica gel (eluted by 10% ethyl acetate in hexane) to give product AM as a colorless oil [Chen, Q.-Y.; Liu, Y.; Luesch, H. ACS Med. Chem. Lett. 2011, 2, 861-865; Kinnaird, J. W. A.; Ng, P. Y.; Kubota, K.; Wang, X.; Leighton, J. L. J. Am. Chem. Soc. 2002, 124, 7920-7921; Rodolfo T.-A.; Tara D. N.; William A. M. J. Org. Chem. 2012, 77, 6271-6289]. $^1$H NMR (400 MHz, CDCl$_3$): δ 7.42-7.40 (m, 6H), 7.30-7.27 (m, 6H), 7.23-7.19 (m, 3H), 5.94-5.85 (m, 1H), 5.31-5.21 (m, 2H), 4.55 (d, J=5.6 Hz, 2H), 4.48 (d, J=8.8 Hz, 1H), 3.64 (br, 1H), 2.33 (br m, 2H), 2.27 (t, J=7.6 Hz, 2H), 1.78-1.65 (m, 2H), 1.43 (s, 9H) ppm. $^{13}$C NMR (100 MHz, CDCl$_3$): δ 172.9, 155.3, 144.7, 132.3, 129.7, 128.0, 126.9, 118.4, 79.4, 66.7, 65.3, 49.5, 37.2, 31.0, 29.7, 28.5 ppm.

Example 6: Preparation of Allyl Ester AN

(R)—N-methyl-N-methoxy-2-tert-butoxycarbonylamino-3-(triphenylmethylthio)propionamide (AD) (2.505 g, 92%)

AD was prepared according to the procedure outlined for AC. [α]$^{20}_D$ −21.8 (c 0.101, CH$_2$Cl$_2$). $^1$H NMR (400 MHz, CDCl$_3$): δ 7.42-7.40 (m, 6H), 7.29-7.25 (m, 6H), 7.22-7.18 (m, 3H), 5.17 (d, J=8.8 Hz, 1H), 4.76 (br m, 1H), 3.63 (s, 3H), 3.14 (s, 3H), 2.56 (dd, J=12.0, 4.4 Hz, 1H), 2.39 (dd, J=12.0, 1H), 1.44 (s, 9H) ppm. $^{13}$C NMR (100 MHz, CDCl$_3$, mixture of rotamers): δ 171.2, 155.2, 129.6, 128.0, 126.8, 79.8, 66.7, 61.6, 49.8, 34.7, 34.2, 32.2, 28.4 ppm. HRMS (ESI) m/z calcd for C$_{29}$H$_{34}$N$_2$O$_4$SNa (M+Na)$^+$ 529.2131, found 529.2133.

Ethyl (R,E-)-4-tert-butoxycarbonylamino-5-(triphenylmethylthio)-penta-2-enoate (AH) (88% 2 Steps)

AH was prepared according to the procedure outlined for AG. [α]$^{20}_D$: +6.0 (c 0.20, CH$_2$Cl$_2$). $^1$H NMR (400 MHz, CDCl$_3$): δ 7.44-7.42 (m, 6H), 7.31-7.27 (m, 6H), 7.24-7.20 (m, 3H), 6.72 (dd, J=15.6, 4.4 Hz, 1H), 5.84 (d, J=15.6 Hz, 1H), 4.80 (d, J=8.4 Hz, 1H), 4.29 (br, 1H), 4.17 (q, J=7.2 Hz, 2H), 2.53-2.41 (m, 2H), 1.45 (s, 9H), 1.27 (t, J=7.2 Hz, 3H) ppm. $^{13}$C NMR (100 MHz, CDCl$_3$): δ 169.9, 154.7, 146.6, 144.3, 129.5, 128.0, 126.8, 121.5, 79.7, 67.0, 60.4, 50.5, 36.2, 28.5, 14.2 ppm. HRMS (ESI) m/z calcd for C$_{31}$H$_{35}$NO$_4$SNa (M+Na)$^+$ 540.2210, found 540.2223.

Ethyl (R)-4-tert-butoxycarbonylamino-5-(triphenylmethylthio)pentanonate (AJ)

AJ was prepared according to the procedure outlined for AI. [α]$^{20}_D$: +4.5 (c 0.20, CH$_2$Cl$_2$). $^1$H NMR (400 MHz, CDCl$_3$): δ 7.42-7.40 (m, 6H), 7.30-7.27 (m, 6H), 7.23-7.19 (m, 3H), 4.49 (d, J=9.2 Hz, 1H), 4.10 (q, J=7.2 Hz, 2H), 3.64 (br, 1H), 2.34 (br m, 2H), 2.21 (t, J=7.6 Hz, 2H), 1.78-1.59 (m, 2H), 1.43 (s, 9H), 1.23 (t, J=7.2 Hz, 3H) ppm. $^{13}$C NMR (100 MHz, CDCl$_3$): δ 173.3, 155.3, 144.7, 129.7, 128.0, 126.8, 79.4, 66.7, 60.5, 49.6, 37.2, 31.1, 29.7, 28.5, 14.3 ppm. HRMS (ESI) m/z calcd for C$_{31}$H$_{37}$NO$_4$SNa (M+Na)$^+$ 542.2336, found 542.2331.

Allyl (R)-4-tert-butoxycarbonylamino-5-(triphenylmethylthio)pentanoate (AN) (0.75 g, 70%)

AN was prepared according to the procedure outlined for AM. [α]$^{20}_D$+10.0 (c 0.16, CH$_2$Cl$_2$). $^1$H NMR (400 MHz, CDCl$_3$): δ 7.42-7.41 (m, 6H), 7.31-7.27 (m, 6H), 7.23-7.20 (m, 3H), 5.95-5.85 (m, 1H), 5.32-5.21 (m, 2H), 4.55 (d, J=5.6 Hz, 2H), 4.49 (d, J=8.8 Hz, 1H), 3.65 (br m, 1H), 2.34 (br m, 2H), 2.26 (t, J=7.6 Hz, 2H), 1.80-1.62 (m, 2H), 1.44 (s, 9H) ppm. $^{13}$C NMR (100 MHz, CDCl$_3$): δ 172.9, 155.3, 144.7, 132.2, 129.6, 128.1, 126.8, 118.3, 79.4, 66.7, 65.3, 49.5, 37.2, 31.0, 29.7, 28.5 ppm. HRMS (ESI) m/z calcd for C$_{32}$H$_{37}$NO$_4$SNa ((M+Na)$^+$ 554.2336, found 554.2341.

Example 7: General Procedure for the Preparation of AO, AS, AX, and BB

To the solution of AM or AN (169.6 mg, 0.319 mmol) in CH$_2$Cl$_2$ (4 mL) were added 2,6-lutidine (556 μL, 4.790 mmol) and trimethylsilyl trifluoromethanesulfonate (TMSOTf) (694 μL, 3.832 mmol) dropwise at room temperature under argon. After being stirred at the same temperature for 1.5 h, the reaction mixture was quenched with MeOH (6 mL) and water (10 mL) at 0° C., and extracted with CH$_2$Cl$_2$ (15 mL×4). The combined organic layers were washed with brine, dried over anhydrous MgSO$_4$ and evaporated in vacuo to give the crude free amine of AM or AN, which was used in next step without further purification.

To the crude free amine of AM or AN (1.3 eq.) in CH$_2$Cl$_2$ (4 ml) were added thr corresponding acid T, U, or AB (based on Scheme 5) (0.245 mmol, 1 eq.), coupling reagent (CR, 0.368 mmol, 1.5 eq.), and DIEA (140 µL, 0.735 mmol, 3.0 eq.) at room temperature or 0° C. After being stirred at room temperature for 2.5-24 h. the resulting reaction mixture was evaporated in vacuo and purified by column chromatography, eluting with ethyl acetate in hexane to give product AO, AS, AX, or BB as a colorless oil.

Pyrrolidine-1,2-dicarboxylic acid (2S)-2-{(1S,3S, 5S,6S)-6-[(1S)-3-allyloxycarbonyl-1-(triphenylmethylthio)methyl-propylcarbamoyl]-1-tert-butyl-5-(2,2, 2-trichloroethoxy-carbonyloxy)-3-methylhept-1-yl}ester 1-(9H-fluoren-9-ylmethyl)ester (AO)

(from T, AM; CR BEP added at 0° C.; reaction time 2.5 h) (245.6 mg, 87%). $^1$H NMR (400 MHz, CDCl$_3$, mixture of rotamers): δ 7.77-7.74 (m, 2H), 7.68 (d, J=7.2 Hz, 0.4H), 7.68 (d, J=7.2 Hz, 1.6H), 7.41-7.36 (m, 8H), 7.33-7.26 (m, 8H), 7.21-7.18 (m, 3H), 6.15 (d, J=8.0 Hz, 0.6H), 5.91-5.78 (m, 1H), 5.43 (d, J=8.8 Hz, 0.4H), 5.30-5.17 (m, 2H), 5.0 (br m, 0.6H), 4.86-4.83 (m, 0.4H), 4.78 (d, J=12.4 Hz, 1.2H), 4.72 (d, J=12.4 Hz, 0.4H), 4.62 (d, J=12.4H, 0.4H), 4.52-4.47 (m, 4H), 4.42-4.38 (m, 1H), 4.30-4.18 (m, 2H), 3.87-3.78 (m, 1H), 3.68-3.61 (m, 1H), 3.59-3.47 (m, 1H), 2.58-2.51 (m, 0.2H), 2.44-2.38 (m, 0.2H), 2.35-2.26 (m, 3H), 2.19-1.12 (m, 4H), 2.00-1.78 (m, 2.6H), 1.74-1.56 (m, 3H), 1.37-1.26 (m, 1H), 1.24-1.18 (m, 1H), 1.12 (d, J=6.4 Hz, 1.8H), 1.11 (d, J=6.0 Hz, 1.2H), 0.94 (d, J=6.4 Hz, 1.8H), 0.88 (s, 3.6H), 0.86 (s, 5.4H), 0.75 (d, J=6.4 Hz, 1.2H) ppm. $^{13}$C NMR (100 MHz, CDCl$_3$, mixture of rotamers): δ 172.9, 172.8, 172.6, 172.2, 172.1, 154.8, 154.5, 153.9, 153.9, 144.7, 144.6, 144.4, 144.2, 144.0, 143.8, 141.4, 141.3, 132.2, 132.2, 129.7, 129.7, 129.6, 128.1, 128.1, 127.8, 127.3, 127.2, 127.1, 126.9, 126.9, 125.7, 125.4, 125.2, 120.1, 118.5, 118.4, 94.9, 94.9, 79.4, 79.1, 78.9, 78.5, 77.4, 76.7, 76.6, 67.9, 67.6, 66.9, 66.8, 65.3, 65.3, 59.9, 59.5, 48.5, 48.4, 47.3, 47.1, 46.5, 45.5, 45.0, 38.2, 37.6, 36.8, 36.6, 36.4, 35.1, 34.8, 31.7, 31.4, 30.9, 30.1, 29.2, 26.2, 26.1, 26.0, 25.9, 24.4, 23.5, 22.8, 20.4, 20.0, 13.7, 13.1 ppm.

Pyrrolidine-1,2-dicarboxylic acid (2S)-2-{(1,3,5)-6-[(1)-3-allyloxycarbonyl-1-(triphenylmethylthio) methyl-propylcarbamoyl]-1-tert-butyl-5-hydroxy-3-methylhex-1-yl}ester 1-(9H-fluoren-9-ylmethyl) ester (AS)

(from U, AM; CR HATU added at rt, reaction time 3.0 h) (193.8 mg, 82%). [α]$^{20}$$_D$ –31.2 (c 0.24, CH$_2$Cl$_2$). $^1$H NMR (400 MHz, CDCl$_3$, mixture of rotamers): δ 7.74 (d, J=7.6 Hz, 2H), 7.63-7.54 (m, 2H), 7.41-7.36 (m, 8H), 7.30-7.15 (m, 11H), 6.69 (d, J=8.8 Hz, 0.84H), 6.06 (d, J=8.4 Hz, 0.16H), 5.92-5.77 (m, 1H), 5.30-5.15 (m, 2H), 4.89 (d, J=11.2 Hz, 0.84H), 4.79 (d, J=10.4 Hz, 0.16H), 4.53-4.44 (m, 2H), 4.39-4.29 (m, 2H), 4.23-4.16 (m, 1H), 4.01 (br m, 1H), 3.95-3.85 (m, 1H), 3.79 (br, 1H), 3.66-3.61 (m, 1H), 3.58-3.44 (m, 1H), 2.40-2.15 (m, 6H), 2.11-2.01 (m, 3H), 1.98-1.88 (m, 2H), 1.85-1.75 (m, 2H), 1.71-1.60 (m, 3H), 1.55-1.47 (m, 1H), 1.40-1.30 (m, 1H), 1.04-0.97 (m, 1H), 0.96 (d, J=6.8 Hz, 2.52H), 0.88 (s, 9H), 0.77 (d, J=6.8 Hz, 0.48H) ppm. $^{13}$C NMR (100 MHz, CDCl$_3$, mixture of rotamers): δ 172.7, 172.3, 172.0, 155.2, 144.8, 144.7, 144.0, 143.9, 141.4, 132.3, 129.7, 128.1, 128.0, 127.8, 127.3, 127.2, 126.9, 126.8, 125.2, 125.2, 120.1, 120.1, 118.3, 78.7, 67.7, 66.6, 66.3, 65.2, 59.6, 47.9, 47.3, 46.6, 44.3, 42.9, 42.2, 41.4, 38.0, 37.1, 36.8, 34.9, 34.6, 31.7, 31.3, 31.0, 30.0, 29.8, 29.3, 26.1, 25.2, 24.5, 23.5, 22.8, 20.7, 14.3 ppm. HRMS (ESI) m/z calcd for C$_{59}$H$_{68}$N$_2$O$_8$SNa (M+Na)$^+$ 987.4589, found 987.4628.

Pyrrolidine-1,2-dicarboxylic acid (2S)-2-{(1,3,5)-6-[(1)-3-allyloxycarbonyl-1-(triphenylmethylthio) methyl-propylcarbamoyl]-1-tert-butyl-3,6-dimethyl-5-(2,2,2-trichloroethoxycarbonyloxy)hept-1-yl}ester 1-(9H-fluoren-9-ylmethyl)ester (AX)

(from AB, AM; CR PyAOP added at rt, reaction time 24 h) (254.3 mg, 89%). [α]$^{20}$$_D$ –48.5 (c 0.20, CH$_2$Cl$_2$). $^1$H NMR (400 MHz, CDCl$_3$, mixture of rotamers): δ 7.78-7.75 (m, 2H), 7.67 (d, J=7.6 Hz, 0.6H), 7.62 (d, J=7.2 Hz, 1.4H), 7.41-7.38 (m, 8H), 7.34-7.27 (m, 8H), 7.22-7.20 (m, 3H), 6.02 (d, J=8.0 Hz, 0.4H), 5.96 (d, J=8.4 Hz, 0.6H), 5.92-5.80 (m, 1H), 5.30-5.18 (m, 2H), 5.13 (d, J=10.0 Hz, 0.4H), 5.04 (d, J=10.0 Hz, 0.6H), 4.95 (d, J=12.0 Hz, 0.6H), 4.83 (d, J=12.0 Hz, 0.4H), 4.79-4.75 (m, 1H), 4.70 (d, J=12.0 Hz, 0.4H), 4.66 (d, J=12.0 Hz, 0.6H), 4.52-4.34 (m, 4.4H), 4.28-4.23 (m, 1H), 4.20-4.16 (m, 0.6H), 3.99-3.87 (m, 1H), 3.67-3.45 (m, 2H), 2.36-2.27 (m, 2.6H), 2.24-2.16 (m, 2.4H), 2.12 (br m, 1H), 2.01-1.90 (m, 2H), 1.85-1.74 (m, 3H), 1.53-1.44 (m, 2H), 1.37-1.27 (m, 1H), 1.19-1.16 (m, 6H), 1.06-1.00 (m, 1H), 0.97 (d, J=6.4 Hz, 1.8H), 0.88 (s, 5.4H), 0.85 (s, 3.6H), 0.69 (d, J=6.4 Hz, 1.2H) ppm. $^{13}$C NMR (100 MHz, CDCl$_3$, mixture of rotamers): δ 174.2, 172.7, 172.6, 172.2, 154.6, 154.3, 154.2, 154.1, 144.5, 144.5, 144.3, 144.1, 143.9, 143.7, 141.3, 141.2, 132.1, 132.0, 129.5, 128.0, 127.7, 127.1, 127.0, 126.8, 125.4, 125.3, 125.1, 125.1, 120.0, 119.9, 118.3, 94.8, 94.8, 81.6, 81.4, 79.6, 79.4, 79.3, 76.7, 67.8, 67.4, 66.5, 65.2, 59.8, 59.3, 48.3, 47.2, 47.0, 46.8, 46.3, 38.1, 37.8, 36.8, 36.3, 36.3, 34.8, 34.7, 34.5, 31.6, 31.3, 30.8, 30.0, 26.8, 26.5, 25.8, 25.8, 25.3, 24.4, 23.4, 23.1, 22.7, 20.4, 20.3, 20.1, 14.2 ppm. HRMS (ESI) m/z calcd for C$_{64}$H$_{73}$Cl$_3$N$_2$O$_{10}$SNa (M+Na)$^+$ 1189.3944, found 1189.3964.

Pyrrolidine-1,2-dicarboxylic acid (2S)-2-{(1S,3S, 5S,6S)-6-[(1R)-3-allyloxycarbonyl-1-(triphenylmethylthio)methyl-propylcarbamoyl]-1-tert-butyl-3-methyl-5-(2,2,2-trichloro-ethoxycarbonyloxy)hept-1-yl}ester 1-(9H-fluoren-9-ylmethyl)ester (BB)

(from T, AN; CR PyAOP added at rt, reaction time 24 h) (257.0 mg, 91%). [α]$^{20}$$_D$ –40.0 (c 0.05, CH$_2$Cl$_2$). $^1$H NMR (400 MHz, CDCl$_3$, mixture of rotamers): δ 7.87-7.78 (m, 2H), 7.71-7.67 (dd, J=8.4, 8.0 Hz, 2H), 7.51-7.46 (m, 8H), 7.40-7.28 (m, 11H), 6.17 (d, J=8.4 Hz, 0.6H), 6.02-5.92 (m, 1H), 5.51 (d, J=8.4 Hz, 0.4H), 5.40-5.30 (m, 2H), 5.10 (ddd, J=7.6, 7.4, 7.2 Hz, 1H), 4.97-4.80 (m, 2.4H), 4.75 (d, J=12.0 Hz, 0.6H), 4.62-4.30 (m, 6H), 4.00 (br m, 1H), 3.74-3.55 (m, 2H), 2.60-2.57 (m, 0.4H), 2.42-2.23 (m, 6.6H), 2.06 (br m, 2H), 1.98-1.86 (m, 1H), 1.82-1.70 (m, 3H), 1.66-1.58 (m, 2H), 1.55-1.30 (m, 1H), 1.24 (d, J=6.8 Hz, 1.8H), 1.20 (d, J=7.2 Hz, 1.2H), 1.07 (d, J=6.0 Hz, 1.8H), 0.98 (s, 3.6H), 0.96 (s, 5.4H), 0.88 (d, J=6.4 Hz, 1.2H) ppm. $^{13}$C NMR (100 MHz, CDCl$_3$, mixture of rotamers): δ 172.8, 172.8, 172.6, 172.5, 172.4, 172.3, 154.9, 154.5, 153.7, 153.7, 144.6, 144.5, 144.2, 144.0, 143.8, 141.4, 141.2, 132.2, 129.8, 129.6, 128.1, 128.0, 127.8, 127.3, 127.2, 127.1, 126.9, 126.9, 125.7, 125.5, 125.2, 120.0, 118.6, 118.5, 79.5, 79.2, 79.0, 78.7, 76.7, 68.0, 67.5, 66.8, 66.7, 65.4, 65.4, 59.8, 59.5, 48.1, 47.3, 47.3, 47.1, 46.4, 45.7, 45.4, 38.3, 37.6, 37.1, 36.6, 36.5, 35.1, 34.8, 34.8, 31.7, 31.4, 29.9, 30.1, 29.8, 29.2, 29.2, 26.2, 26.1, 26.0, 25.9, 25.4, 24.4, 23.5, 22.8, 20.6, 20.2, 14.3, 14.0, 13.8 ppm. HRMS (ESI) m/z calcd for C$_{63}$H$_{71}$C$_3$N$_2$O$_{10}$SNa (M+Na)$^+$ 1175.3787, found 1175.3805.

Example 8: Preparation of AT

Pyrrolidine-1,2-dicarboxylic acid (2S)-2-{(1,3,5)-6-[(1)-3-allyloxycarbonyl-1-(triphenylmethylthio)methyl-propylcarbamoyl]-1-tert-butyl-3-methyl-5-(2,2,2-trichloroethoxycarbonyloxy)hex-1-yl}ester 1-(9H-fluoren-9-ylmethyl)ester (AT)

To the solution of compound AS (166.3 mg, 0.172 mmol) and pyridine (140 µL, 1.742 mmol) in $CH_2Cl_2$ (5.0 ml) were added 2,2,2-trichloroethoxylcarbonyl chloride (Troc-Cl) (182.6 mg/118.7 µL, 0.862 mmol) and 4-dimethylaminopyridine (DMAP) (0.36 mg, 2.93 µmol) at 0° C. After being stirred at the same temperature for 1 h, the reaction was quenched with water (15 mL). The water layer was extracted with ethyl acetate (20 mL×4). The combined organic layers were washed with 5% $NaHCO_3$ (20 mL×2), brine (20 mL), dried with $MgSO_4$ and concentrated in vacuo. The residue was purified by chromatography column on silica gel (20-30% ethyl acetate in hexane) to give AT (156.5 mg, 80%). $[\alpha]^{20}_D$ −45.0 (c 0.111, $CH_2Cl_2$). $^1H$ NMR (400 MHz, $CDCl_3$, mixture of rotamers): δ 7.77-7.74 (m, 2H), 7.67 (d, J=7.6 Hz, 0.4H), 7.60 (d, J=7.6 Hz, 1.6H), 7.41-7.37 (m, 8H), 7.33-7.17 (m, 11H), 6.13 (d, J=8.4 Hz, 0.6H), 5.92-5.80 (m, 1H), 5.62 (d, J=8.4 Hz, 0.4H), 5.30-5.18 (m, 2.4H), 4.85-4.80 (m, 1.2H), 4.77 (d, J=12.0 Hz, 0.4H), 4.61 (d, J=12.0 Hz, 0.4H), 4.54 (d, J=12.0 Hz, 0.6H), 4.53-4.45 (m, 3H), 4.40-4.30 (m, 1.4H), 4.26-4.18 (m, 1.6H), 3.93-3.82 (m, 1H), 3.66-3.60 (m, 1H), 3.58-3.45 (m, 1H), 2.54-2.56 (m, 4H), 2.22-2.10 (m, 3H), 2.00-1.85 (m, 3H), 1.75-1.60 (m, 2H), 1.55-1.24 (m, 3H), 0.99 (d, J=6.4 Hz, 1.8H), 0.88 (s, 3.6H), 0.87 (s, 5.4H), 0.80 (d, J=6.4 Hz, 1.2H) ppm. $^{13}C$ NMR (100 MHz, $CDCl_3$, mixture of rotamers): δ 172.8, 172.7, 172.7, 172.3, 168.7, 168.3, 154.9, 154.4, 153.6, 153.5, 144.6, 144.6, 144.2, 144.1, 143.9, 143.8, 141.3, 141.3, 132.2, 132.1, 129.6, 128.0, 128.0, 127.8, 127.8, 127.1, 126.9, 126.8, 125.5, 125.4, 125.2, 120.0, 120.0, 118.4, 118.3, 94.8, 94.8, 79.5, 79.1, 76.7, 76.6, 75.3, 74.8, 67.8, 67.5, 65.3, 65.2, 59.8, 59.5, 48.4, 47.3, 47.0, 46.5, 41.6, 41.0, 39.8, 39.4, 38.1, 37.7, 36.4, 36.3, 35.0, 34.7, 31.7, 31.3, 29.8, 29.1, 25.9, 25.9, 25.4, 24.4, 23.4, 22.7, 20.8, 20.7, 14.2 ppm. HRMS (ESI) m/z calcd for $C_{62}H_{69}Cl_3N_2O_{10}SNa$ (M+Na)$^+$ 1161.3631, found 1161.3634.

Example 9: General Procedure for the Preparation of AQ, AV, and BD

To the solution of triphenylphosphine oxide (223.3 mg, 0.802 mmol) in $CH_2Cl_2$ (1 ml) was added dropwise trifluoromethanesulfonic anhydride (Tf$_2$O) (68 µL, 0.401 mmol) at 0° C. under argon. After being stirred at the same temperature for 10 min, compound AO, AT, or BB (0.100 mmol) in $CH_2Cl_2$ (0.5 mL) was added at 0° C. The reaction mixture was stirred at the same temperature for 30 min for AO/AT and 3 h for BB. This reaction was monitored by mass spectrometry and was quenched with saturated $NaHCO_3$ (6 mL) at 0° C. when starting material disappeared. The aqueous layer was extracted with ethyl acetate (10 mL×4), washed with brine (10 mL), dried with $MgSO_4$, filtered and concentrated in vacuo to give Troc protected thiazoline intermediate AP, AU or BC. The residue was used in the next step immediately without further purification.

The above residue was dissolved in THF (4 mL) and then aqueous $NH_4OAc$ (1 M, 1.0 mL), and zinc powder (freshly activated with 1 M aqueous HCl) (100 mg) were added at room temperature. After being stirred at the same temperature for 30 min, ethyl acetate (5 mL) and brine (5 mL) and were added to the reaction mixture. The aqueous layer was extracted with ethyl acetate (5 mL×4). The combined organic layers were dried with $MgSO_4$, filtered, concentrated in vacuo, and purified by column chromatography on silica gel (eluted by ethyl acetate/hexane 1:3, v/v) to give thiazoline ring product AQ, AV or BD as a colorless oil.

Pyrrolidine-1,2-dicarboxylic acid (2)-2-{(1,3,5,6S)-6-[(5S)-5-(2-allyloxycarbonylethyl)-4,5-dihydro-thiazol-2-yl]-1-tert-butyl-5-hydroxy-3-methylhept-1-yl}ester 1-(9H-fluoren-9-ylmethyl)ester (AQ)

(65.0 mg, 78%). $^1H$ NMR (400 MHz, $CDCl_3$, mixture of rotamers): δ 7.75 (d, J=7.6 Hz, 2H), 7.64 (dd, J=6.8, 6.8 Hz, 1.7H), 7.57 (d, J=7.2 Hz, 0.3H), 7.39 (dd, J=7.2, 6.8 Hz, 2H), 7.30 (dd, J=7.2, 6.8 Hz, 2H), 5.95-5.84 (m, 1H), 5.31-5.19 (m, 2H), 4.88 (d, J=11.2 Hz, 0.7H), 4.82 (d, J=10.4 Hz, 0.3H), 4.58-4.19 (m, 7H), 3.77 (br m, 1H), 3.67-3.61 (m, 1H), 3.58-3.48 (m, 1H), 3.35-3.21 (m, 1H), 2.90-2.82 (m, 1H), 2.67-2.49 (m, 2H), 2.30-2.19 (m, 1H), 2.10-1.93 (m, 5H), 1.82 (m, 1H), 1.71-1.58 (m, 2.3H), 1.50-1.42 (m, 0.7H), 1.38-1.25 (m, 2H), 1.22 (d, J=6.8 Hz, 0.9H), 1.18 (d, J=6.4 Hz, 2.1H), 0.96 (d, J=6.4 Hz, 2.1H), 0.88 (s, 9H), 0.80 (d, J=6.4 Hz, 0.9H) ppm. $^{13}C$ NMR (100 MHz, $CDCl_3$, mixture of rotamers): δ 173.1, 173.0, 172.8, 172.5, 155.0, 155.0, 154.4, 144.4, 144.3, 144.1, 143.9, 141.4, 141.4, 141.3, 132.3, 132.3, 127.7, 127.7, 127.1, 125.5, 125.4, 125.3, 120.0, 118.4, 118.3, 79.4, 78.5, 76.0, 75.7, 71.6, 71.5, 67.9, 67.7, 65.3, 65.2, 59.7, 47.3, 47.2, 47.1, 46.6, 45.7, 45.1, 40.4, 39.8, 39.3, 38.0, 37.8, 37.4, 37.2, 34.8, 34.7, 31.6, 31.4, 31.3, 30.4, 30.3, 30.0, 29.8, 26.1, 26.1, 25.7, 25.2, 24.6, 23.4, 20.6, 20.5, 16.4, 15.7 ppm.

Pyrrolidine-1,2-dicarboxylic acid (2S)-2-{(1,3,5)-6-[(5)-5-(2-allyloxycarbonylethyl)-4,5-dihydro-thiazol-2-yl]-1-tert-butyl-5-hydroxy-3-methylhex-1-yl}ester 1-(9H-fluoren-9-ylmethyl)ester (AV)

(53.2 mg, 76%). $[\alpha]^{20}_D$ −78.0 (c 0.10, $CH_2Cl_2$). $^1H$ NMR (400 MHz, $CDCl_3$, mixture of rotamers): δ 7.74 (d, J=7.6 Hz, 2H), 7.63 (dd, J=5.6, 6.0 Hz, 1.6H), 7.56 (d, J=7.6 Hz, 0.4H), 7.37 (dd, J=7.2, 7.2 Hz, 2H), 7.32-7.27 (m, 2H), 5.93-5.83 (m, 1H), 5.30-5.19 (m, 2H), 4.90 (d, J=10.8 Hz, 0.8H), 4.83 (d, J=9.6 Hz, 0.2H), 4.58-4.51 (m, 2H), 4.46-4.34 (m, 3.8H), 4.28-4.18 (m, 1.2H), 3.97 (br m, 1H), 3.68-3.61 (m, 2H), 3.57-3.47 (m, 1H), 3.33 (dd, J=10.4, 8.8 Hz, 0.2H), 3.24 (dd, J=10.4, 8.8 Hz, 0.8H), 2.88 (dd, J=10.0, 8.4 Hz, 0.2H), 2.81 (dd, J=10.4, 8.4 Hz, 0.8H), 2.55-2.48 (m, 4H), 2.29-2.19 (m, 1H), 2.08-1.80 (m, 5H), 1.75-1.58 (m, 2H), 1.48-1.25 (m, 2H), 1.04-0.97 (m, 1H), 0.96 (d, J=6.4 Hz, 2.4H), 0.87 (s, 9H), 0.79 (d, J=6.4 Hz, 0.6H) ppm. $^{13}C$ NMR (100 MHz, $CDCl_3$, mixture of rotamers): δ 172.9, 172.9, 172.8, 172.3, 169.2, 169.1, 154.9, 154.3, 144.3, 144.1, 144.0, 143.8, 141.3, 141.3, 141.2, 132.2, 132.2, 127.6, 127.6, 127.1, 127.0, 127.0, 127.0, 125.4, 125.3, 125.3, 125.2, 79.5, 78.5, 76.0, 75.8, 67.8, 67.7, 67.2, 66.7, 65.2, 65.1, 59.5, 47.2, 47.1, 47.0, 46.5, 42.9, 42.2, 42.0, 41.9, 38.0, 37.9, 37.4, 34.8, 34.7, 34.6, 31.6, 31.5, 31.4, 31.2, 30.4, 29.9, 26.0, 25.9, 25.7, 25.3, 25.1, 24.5, 23.3, 22.7, 20.6, 20.5, 14.2 ppm. HRMS (ESI) n/z calcd for $C_{40}H_{52}N_2O_7SNa$ (M+Na)$^+$ 727.3387, found 727.3399.

Pyrrolidine-1,2-dicarboxylic acid (2S)-2-{(1S,3S,5S,6S)-6-[(5R)-5-(2-allyloxycarbonylethyl)-4,5-dihydro-thiazol-2-yl]-1-tert-butyl-5-hydroxy-3-methylhept-1-yl}ester 1-(9H-fluoren-9-ylmethyl)ester (BD)

(57.0 mg, 79%). $[\alpha]^{20}_D$ −22.5 (c 0.12, $CH_2Cl_2$). $^1H$ NMR (400 MHz, $CDCl_3$, mixture of rotamers): δ 7.76 (d, J=7.2

Hz, 2H), 7.63 (dd, J=6.6, 6.4 Hz, 1.7H), 7.57 (d, J=7.2 Hz, 0.3H), 7.39 (dd, J=7.2, 7.2 Hz, 2H), 7.30 (dd, J=7.4, 7.2 Hz, 2H), 5.94-5.85 (m, 1H), 5.31-5.20 (m, 2H), 4.88 (d, J=10.0 Hz, 0.7H), 4.81 (d, J=8.8 Hz, 0.3H), 4.59-4.51 (m, 2.3H), 4.45-4.33 (m, 3H), 4.31-4.18 (m, 1.7H), 3.82-3.72 (m, 0.7H), 3.68-3.62 (m, 1.3H), 3.58-3.49 (m, 1.3H), 3.35-3.24 (m, 1H), 2.90-2.85 (m, 0.3H), 2.81 (dd, J=10.8, 7.6 Hz, 0.7H), 2.72-2.65 (m, 0.7H), 2.61-2.44 (m, 2.3H), 2.34-2.18 (m, 1.7H), 2.10-1.89 (m, 4.4H), 1.82 (m, 0.7H), 1.70-1.57 (m, 2H), 1.37-1.29 (m, 1H), 1.19 (d, J=7.0 Hz, 0.9H), 1.17 (d, J=7.0 Hz, 2.1H), 1.06-1.00 (m, 1H), 0.96 (d, J=6.4 Hz, 2.1H), 0.87 (s, 9H), 0.79 (d, J=6.4 Hz, 0.9H) ppm. $^{13}$C NMR (100 MHz, CDCl$_3$, mixture of rotamers): δ 174.2, 173.1, 173.0, 172.8, 172.5, 155.0, 154.5, 144.4, 144.3, 144.1, 143.9, 141.4, 141.4, 141.3, 132.3, 132.3, 128.0, 127.7, 127.4, 127.2, 127.1, 125.6, 125.4, 125.3, 125.3, 121.0, 120.0, 118.4, 118.3, 79.6, 78.6, 77.4, 76.2, 75.7, 71.5, 71.5, 70.7, 67.9, 67.8, 65.3, 65.3, 59.7, 59.7, 47.3, 47.2, 47.1, 46.6, 46.0, 45.3, 40.4, 39.3, 38.2, 37.8, 37.4, 37.3, 34.8, 34.7, 31.7, 31.5, 31.3, 30.3, 30.2, 30.1, 29.8, 26.1, 26.1, 25.9, 25.5, 25.3, 24.6, 23.4, 20.7, 20.6, 16.3, 15.8 ppm. HRMS (ESI) m/z calcd for C$_{41}$H$_{54}$N$_2$O$_7$SNa (M+Na)$^+$ 741.3544, found 741.3567.

Example 10: Preparation of AZ

Pyrrolidine-1,2-dicarboxylic acid (2S)-2-{(1,3,5)-6-[(S)-5-(2-allyloxycarbonylethyl)-4,5-dihydro-thiazol-2-yl]-1-tert-butyl-3,6-dimethyl-5-hydroxyhept-1-yl}ester 1-(9H-fluoren-9-ylmethyl)ester (AZ)

To the solution of AX (97.8 mg, 0.084 mmol) in 1,2-dichloroethane (5 mL) was added TiCl$_4$ (1M in CH$_2$Cl$_2$, 0.294 mL, 0.293 mmol, 3.5 eq.) at room temperature. The resulting solution was heated to 60° C. and stirred at this temperature for 2.5 h. This reaction was monitored by mass spectrometry. When the starting material was consumed completely, the reaction was cooled to 0° C. and quenched with saturated aq. NaHCO$_3$ (7 mL), stirred at room temperature for another 10 min, extracted with ethyl acetate (10 mL×4), dried over anhydrous MgSO$_4$, filtered and evaporated in vacuo to give crude intermediate AY, which was used in the next step without further purification.

The above crude AY was dissolved in THF (4 mL) and then aqueous NH$_4$OAc (1 M, 1.0 mL) and zinc powder (freshly activated with 1 M aqueous HCl) (80 mg) was added at room temperature. After being stirred at the same temperature for 30 min, ethyl acetate (5 mL) and brine (5 mL) were added to the reaction. The aqueous layer was extracted with ethyl acetate (7 mL×4). The combined organic layers were dried with MgSO$_4$, filtered, concentrated in vacuo, and purified by silica gel column chromatography (eluted by ethyl acetate/hexane 1:3, v/v) to give thiazoline ring product AZ (101.3 mg, 55%) as a colorless oil. [α]$^{20}_D$ −80.8 (c 0.12, CH$_2$Cl$_2$). $^1$H NMR (400 MHz, CDCl$_3$, mixture of rotamers): δ 7.76-7.74 (m, 2H), 7.66-7.61 (m, 1.7H), 7.57 (d, J=7.2 Hz, 0.3H), 7.39 (dd, J=7.4, 7.2 Hz, 2H), 7.31-7.28 (m, 2H), 5.94-5.84 (m, 1H), 5.31-5.19 (m, 2H), 4.88 (dd, J=11.6, 1.6 Hz, 0.7H), 4.81 (dd, J=11.6, 1.6 Hz, 0.3H), 4.58-4.54 (m, 2H), 4.52-4.38 (m, 3H), 4.35-4.19 (m, 2H), 3.66-3.59 (m, 2H), 3.58-3.48 (m, 2H), 3.30-3.23 (m, 1H), 2.86-2.81 (m, 1H), 2.59-2.46 (m, 2H), 2.36-2.19 (m, 1H), 2.12-1.91 (m, 5H), 1.78 (br m, 1H), 1.67-1.56 (m, 2H), 1.37-1.27 (m, 2H), 1.22 (s, 0.9H), 1.19-1.18 (m, 5.1H), 0.96 (d, J=6.4 Hz, 2.1H), 0.87 (s, 9H), 0.79 (d, J=6.8 Hz, 0.9H) ppm. $^{13}$C NMR (100 MHz, CDCl$_3$, mixture of rotamers): δ 178.8, 178.3, 173.1, 173.0, 172.9, 172.5, 154.9, 154.4, 144.4, 144.3, 144.0, 143.9, 141.4, 141.3, 141.2, 132.3, 127.7, 127.7, 127.1, 127.1, 125.5, 125.4, 125.3, 125.2, 120.0, 118.3, 118.3, 79.4, 78.6, 76.0, 75.8, 75.0, 74.9, 67.9, 67.7, 65.2, 65.2, 59.7, 59.7, 47.3, 47.2, 47.0, 46.5, 45.9, 45.6, 38.0, 37.8, 37.0, 37.0, 36.9, 36.6, 34.8, 34.6, 31.6, 31.4, 31.3, 30.3, 30.2, 30.0, 29.8, 26.1, 25.8, 25.3, 24.5, 24.3, 23.7, 23.4, 23.1, 20.6, 20.5 ppm (ESI) m/z calcd for C$_{42}$H$_{56}$N$_2$O$_7$SNa (M+Na)$^+$ 755.3700, found 755.3718.

Example 11: General Procedure for the Preparation of AR, AW, BA, and BE

To a solution of AQ, AV, AZ, or BD (0.054 mmol) in THF (1.5 mL) were added Pd(PPh$_3$)$_4$ (7.1 mg, 0.005 mmol) and N-methylaniline (0.015 mL, 0.136 mmol) at room temperature under argon. This reaction was protected with aluminum foil. After being stirred at the same temperature for 1 h, the reaction mixture was concentrated in vacuo and purified by preparative TLC (20 cm×20 cm plate) to give acid AR, AW, BA, or BE.

Pyrrolidine-1,2-dicarboxylic acid (2S)-2-{(1,3,5,6)-6-[(5S)-5-(2-carboxylethyl)-4,5-dihydro-thiazol-2-yl]-1-tertbutyl-5-hydroxy-3-methylhept-1-yl}ester 1-(9H-fluoren-9-ylmethyl)ester (AR)

(35.3 mg, 96%). $^1$H NMR (400 MHz, CDCl$_3$, mixture of rotamers): δ 7.75 (d, J=7.6 Hz, 2H), 7.64-7.58 (m, 2H), 7.39 (dd, J=7.6, 7.4 Hz, 2H), 7.30 (dd, J=7.6, 7.4 Hz, 2H), 5.90 (br, 1H), 4.91-4.79 (m, 1H), 4.52-4.17 (m, 5H), 3.81-3.47 (m, 3H), 3.36-3.14 (m, 1H), 2.92-2.81 (m, 1H), 2.68-2.50 (m, 2H), 2.31-2.20 (m, 1H), 2.06-1.88 (m, 5H), 1.82 (br m, 1H), 1.71-1.60 (m, 2.3H), 1.50-1.42 (m, 0.7H), 1.38-1.25 (m, 2H), 1.21 (d, J=6.8 Hz, 0.9H), 1.17 (d, J=6.4 Hz, 2.1H), 0.95 (d, J=6.4 Hz, 2.1H), 0.87 (s, 9H), 0.75 (d, J=6.4 Hz, 0.9H) ppm. $^{13}$C NMR (100 MHz, CDCl$_3$, mixture of rotamers): δ 177.7, 175.9, 172.6, 155.2, 155.1, 144.2, 144.1, 143.8, 141.4, 141.4, 127.8, 127.1, 125.5, 125.4, 125.3, 120.0, 79.6, 78.7, 78.6, 77.4, 75.8, 75.3, 71.5, 70.9, 67.9, 67.9, 59.6, 47.3, 47.1, 46.6, 46.0, 45.8, 45.1, 40.4, 39.4, 39.1, 38.0, 37.7, 37.6, 37.5, 34.8, 34.6, 32.8, 31.7, 33.0, 30.2, 30.0, 29.9, 29.8, 26.1, 25.4, 25.1, 24.9, 24.6, 23.4, 22.8, 20.8, 20.5, 20.4, 16.5, 15.7, 14.4, 14.2 ppm.

Pyrrolidine-1,2-dicarboxylic acid (2S)-2-{(1,3,5)-6-[(S)-5-(2-carboxylethyl)-4,5-dihydro-thiazol-2-yl]-1-tert-butyl-5-hydroxy-3-methylhex-1-yl}ester 1-(9H-fluoren-9-ylmethyl)ester (AW)

(31.8 mg, 89%). [α]$^{20}_D$ −90.0 (c 0.04, CH$_2$Cl$_2$). $^1$H NMR (400 MHz, CDCl$_3$, mixture of rotamers): δ 7.74 (d, J=7.6 Hz, 2H), 7.63 (d, J=7.2 Hz, 1.8H), 7.57 (d, J=7.6 Hz, 0.2H), 7.38 (dd, J=7.6, 7.6 Hz, 2H), 7.32-7.28 (m, 2H), 6.22 (br, 1H), 4.90 (d, J=10.0 Hz, 0.8H), 4.84 (d, J=9.2 Hz, 0.2H), 4.53-4.34 (m, 3.8H), 4.29-4.17 (m, 1.2H), 4.00-3.92 (m, 1H), 3.68-3.61 (m, 1H), 3.57-3.45 (m, 1H), 3.35 (dd, J=10.8, 8.8 Hz, 0.2H), 3.23 (dd, J=10.8, 8.4 Hz, 0.8H), 2.91 (dd, J=10.8, 8.4 Hz, 0.2H), 2.80 (dd, J=10.8, 8.4 Hz, 0.8H), 2.60-2.43 (m, 4H), 2.35-2.17 (m, 1H), 2.08-1.82 (m, 5H), 1.74-1.59 (m, 2H), 1.48-1.25 (m, 2H), 1.03-0.96 (m, 1H), 0.96 (d, J=6.4 Hz, 2.4H), 0.87 (s, 9H), 0.77 (d, J=6.4 Hz, 0.6H) ppm. $^{13}$C NMR (100 MHz, CDCl$_3$, mixture of rotamers): δ 176.7, 176.5, 173.1, 172.5, 171.8, 170.5, 155.1, 154.5, 144.3, 144.1, 144.0, 143.8, 141.4, 141.4, 141.3, 141.3, 127.7, 127.7, 127.2, 127.1, 125.5, 125.4, 125.3, 120.0, 79.8, 75.7, 75.3, 67.9, 67.8, 67.4, 67.0, 59.6, 47.2, 47.2, 47.0, 46.6, 42.7, 42.3, 42.1, 41.9, 38.2, 38.1, 38.0, 37.4, 36.8, 34.8, 34.7, 32.0, 31.7, 31.3, 30.1, 30.0, 30.0, 26.1, 26.0, 25.7, 25.1, 24.6, 23.4, 20.7, 20.5 ppm. HRMS (ESI) m/z calcd for $C_{37}H_{48}N_2O_7SNa$ (M+Na)$^+$ 687.3074, found 687.3070.

Pyrrolidine-1,2-dicarboxylic acid (2S)-2-{(1,3,5)-6-[(S)-5-(2-carboxylethyl)-4,5-dihydro-thiazol-2-yl]-1-tert-butyl-3,6-dimethyl-5-hydroxyhept-1-yl}ester 1-(9H-fluoren-9-ylmethyl)ester (BA)

(31.2 mg, 84%). $[\alpha]^{20}_D$ −57.7 (c 0.052, CH$_2$Cl$_2$). $^1$H NMR (400 MHz, CDCl$_3$, mixture of rotamers): δ 7.76 (d, J=7.6 Hz, 2H), 7.65-7.58 (m, 2H), 7.39 (dd, J=7.4, 7.2 Hz, 2H), 7.32-7.28 (m, 2H), 4.88 (d, J=12.0, 0.7H), 4.80 (d, J=12.0 Hz, 0.3H), 4.51 (dd, J=8.8, 2.8 Hz, 0.3H), 4.46 (d, J=7.2 Hz, 0.3H), 4.43 (d, J=7.2 Hz, 0.7H), 4.41-4.32 (m, 2H), 4.30-4.25 (m, 1.7H), 3.65-3.56 (m, 2H), 3.53-3.45 (m, 1H), 3.30 (dd, J=11.0, 8.4 Hz, 0.3H), 3.19 (dd, J=11.0, 8.4 Hz, 0.7H), 2.88 (dd, J=10.8, 10.8 Hz, 1H), 2.70-2.53 (m, 2H), 2.37-2.14 (m, 1H), 2.08-1.90 (m, 5H), 1.79 (br m, 1H), 1.68-1.60 (m, 2H), 1.35-1.26 (m, 2H), 1.26 (s, 0.9H), 1.19 (s, 2.1H), 1.18 (s, 3H), 0.95 (d, J=6.6 Hz, 2.1H), 0.87 (s, 9H), 0.74 (d, J=6.6 Hz, 0.9H) ppm. $^{13}$C NMR (100 MHz, CDCl$_3$, mixture of rotamers): δ 182.4, 180.5, 175.7, 175.5, 173.2, 172.7, 155.1, 154.7, 144.5, 144.2, 144.1, 143.8, 141.5, 141.4, 141.3, 127.8, 127.8, 127.2, 127.1, 127.1, 125.5, 125.4, 125.4, 125.3, 120.0, 79.7, 78.6, 76.0, 75.8, 75.4, 75.1, 68.1, 67.9, 59.7, 59.6, 47.3, 47.2, 47.1, 46.6, 46.5, 45.8, 38.0, 37.8, 37.5, 37.4, 37.1, 36.3, 34.8, 34.6, 33.4, 32.7, 32.7, 31.7, 31.3, 30.2, 30.0, 29.8, 29.7 26.1, 25.6, 25.1, 24.9, 24.7, 23.8, 23.7, 23.5, 22.8, 20.7, 20.4, 14.3 ppm. HRMS (ESI) m/z calcd for $C_{39}H_{52}N_2O_7SNa$ (M+Na)$^+$ 715.3387, found 715.3397.

Pyrrolidine-1,2-dicarboxylic acid (2S)-2-{(1S,3S, 5S,6S)-6-[(5R)-5-(2-carboxylethyl)-4,5-dihydro-thiazol-2-yl]-1-tert-butyl-5-hydroxy-3-methylhept-1-yl}ester 1-(9H-fluoren-9-ylmethyl)ester (BE)

(33.0 mg, 90%). $[\alpha]^{20}_D$ −60.0 (c 0.04, CH$_2$Cl$_2$). $^1$H NMR (400 MHz, CDCl$_3$, mixture of rotamers): δ 7.75 (d, J=7.6 Hz, 2H), 7.67-7.57 (m, 2H), 7.39 (dd, J=7.4, 7.2 Hz, 2H), 7.30 (dd, J=7.6, 7.4 Hz, 2H), 5.90 (br, 1H), 4.91 (dd, J=12.8, 12.4 Hz, 0.7H), 4.86-4.82 (m, 0.3H), 4.54-4.50 (m, 0.3H), 4.45-4.40 (m, 1H), 4.38-4.33 (m, 1.7H), 4.30-4.27 (m, 1.3H), 4.25-4.16 (m, 0.7H), 3.82-3.80 (m, 0.7H), 3.75-3.70 (m, 0.3H), 3.64 (br m, 1H), 3.51-3.49 (m, 1H), 3.36-3.30 (m, 0.3H), 3.26-3.15 (m, 0.7H), 2.91-2.85 (m, 0.3H), 2.84-2.72 (m, 0.7H), 2.68-2.50 (m, 3H), 2.35-2.21 (m, 1H), 2.21-2.15 (m, 0.3H), 2.05-1.89 (m, 5H), 1.84-1.79 (m, 0.7H), 1.75-1.70 (m, 1H), 1.66-1.60 (m, 1H), 1.54-1.45 (m, 0.7H), 1.45-1.40 (m, 0.3H), 1.19-1.16 (m, 3H), 1.03-1.00 (m, 1H), 0.96 (d, J=6.0 Hz, 2.1H), 0.88 (s, 9H), 0.74 (d, J=6.0 Hz, 0.9H) ppm. $^{13}$C NMR (100 MHz, CDCl$_3$, mixture of rotamers): δ 177.8, 177.6, 175.9, 173.4, 173.4, 173.3, 172.7, 155.1, 155.1, 154.6, 144.4, 144.4, 144.2, 144.2, 144.2, 144.0, 143.9, 141.4, 141.4, 141.4, 141.3, 141.3, 128.0, 128.0, 127.8, 127.8, 127.5, 127.2, 127.1, 125.5, 125.4, 125.4, 125.3, 121.0, 121.0, 120.0, 120.0, 80.0, 80.0, 79.2, 78.7, 77.4, 76.2, 76.0, 75.6, 75.5, 71.8, 70.8, 70.4, 68.0, 67.9, 67.9, 67.7, 67.5, 59.7, 59.6, 47.3, 47.3, 47.1, 46.6, 46.0, 45.9, 45.4, 40.7, 39.7, 39.4, 39.2, 38.1, 38.0, 37.8, 37.6, 37.0, 34.8, 34.7, 32.9, 32.9, 32.3, 31.7, 31.3, 31.1, 30.2, 30.0, 30.0, 29.8, 29.4, 29.2, 28.7, 26.1, 26.0, 25.8, 25.4, 25.2, 25.1, 24.6, 23.4, 22.8, 20.8, 20.8, 20.6, 20.5, 16.6, 16.0, 14.3, 14.2 ppm. HRMS (ESI) m/z calcd for $C_{38}H_{50}N_2O_7SNa$ (M+Na)$^+$ 701.3231, found 701.3253.

Example 12: General Procedure for the Preparation of BG, BH, BI, and BJ

To a solution of Fmoc protected tripeptide BF (28.1 mg, 0.042 mmol) in MeCN (1.2 mL) was added diethylamine (0.6 mL) at room temperature. After being stirred at the same temperature for 30 min, the reaction mixture was evaporated in vacuo, then azeotroped with toluene and CH$_2$Cl$_2$ twice, respectively, and dried under reduced pressure for 1 h to give the free amine tripeptide, which was used in the next coupling reaction without further purification [Chen, Q.-Y.; Liu, Y.; Luesch, H. ACS Med. Chem. Lett. 2011, 2, 861-865; Doi, T.; Numajiri, Y.; Munakata, A.; Takahashi, T. Org. Lett. 2006, 8, 531-534; Numajiri, Y.; Takahashi, T.; Doi, T. Chem. Asian J. 2009, 4, 111-125].

The above crude free amine tripeptide was dissolved in CH$_2$Cl$_2$ (THF for AW) (2 ml). To this solution was added acid AR, AW, BA, or BE (0.028 mmol), corresponding coupling reagent (0.056 mmol) (PyAOP for AR, BA, BE and DEPBT for AW), DIEA (0.014 ml, 0.083 mmol) at room temperature. After being stirred at the same temperature for 15-24 h, the reaction mixture was concentrated in vacuo and purified by preparative TLC plate (developed by acetone/hexane (2:3, v/v)) to give the precursor BG, BH, BI, or BJ as a colorless oil.

BG: (29.5 mg, 95%). $^1$H NMR (400 MHz, CDCl$_3$, mixture of rotamers): δ 7.75 (d, J=7.2 Hz, 2H), 7.64-7.56 (m, 2H), 7.38 (dd, J=7.4, 7.2 Hz, 2H), 7.29 (dd, J=7.4, 7.2 Hz, 2H), 7.09 (d, J=8.4 Hz, 2H), 6.76 (d, J=8.4 Hz, 2H), 5.92-5.82 (m, 1H), 5.39-5.35 (m, 1H), 5.27-5.13 (m, 3H), 4.80-4.73 (m, 2H), 4.58-4.51 (m, 2H), 4.45-4.18 (m, 5H), 3.80-3.74 (br m, 1H), 3.74 (s, 3H), 3.63 (br m, 1H), 3.52 (br m, 1H), 3.27-3.11 (m, 1H), 3.03-2.89 (m, 4H), 2.82-2.62 (m, 6H), 2.39-2.20 (m, 3H), 2.07-1.58 (m, 8H), 1.50-1.41 (m, 1H), 1.36-1.17 (m, 8H), 1.03-0.92 (m, 8H), 0.87-0.82 (m, 12H) ppm. $^{13}$C NMR (100 MHz, CDCl$_3$, mixture of rotamers): δ 173.2, 173.0, 172.7, 172.3, 172.3, 172.2, 171.9, 171.9, 171.7, 171.6, 171.4, 170.8, 158.6, 155.1, 155.0, 154.6, 144.6, 144.3, 144.1, 144.0, 143.9, 141.4, 141.3, 131.8, 130.5, 130.5, 128.4, 128.3, 127.7, 127.1, 125.5, 125.4, 125.3, 120.0, 118.8, 114.0, 79.8, 79.4, 78.7, 78.7, 77.4, 71.6, 70.8, 70.6, 68.0, 67.8, 66.1, 65.5, 63.8, 60.6, 59.7, 55.3, 50.4, 49.8, 49.8, 47.3, 47.3, 47.2, 47.0, 46.6, 45.8, 45.1, 40.5, 39.7, 39.5, 38.1, 37.8, 37.8, 37.6, 37.5, 37.4, 37.2, 34.8, 34.7, 33.6, 33.5, 33.4, 31.3, 31.0, 30.6, 30.0, 29.8, 26.1, 25.3, 25.2, 25.1, 24.6, 23.4, 22.8, 20.6, 16.7, 16.2, 16.0, 15.9, 14.6, 14.4, 14.2, 11.7, 10.6 ppm.

BH: (22.0 mg, 72%). $[\alpha]^{20}_D$ −99.3 (c 0.14, CH$_2$Cl$_2$). $^1$H NMR (400 MHz, CDCl$_3$, mixture of rotamers): δ 7.77-7.74 (m, 2H), 7.64-7.62 (m, 1.7H), 7.56 (d, J=7.6 Hz, 0.3H), 7.39 (dd, J=7.6, 7.4 Hz, 2H), 7.32-7.26 (m, 2H), 7.09 (d, J=8.0 Hz, 2H), 6.76 (d, J=8.0 Hz, 2H), 6.63 (d, J=8.0 Hz, 0.3H), 6.49 (br m, 0.3H), 6.34-6.27 (m, 1H), 6.20-6.12 (m, 0.3H), 5.92-5.83 (m, 0.7H), 5.54-5.47 (m, 0.3H), 5.42-5.35 (m, 0.7H), 5.31-5.17 (m, 2.7H), 5.11-5.06 (m, 0.3H), 4.94-4.85 (m, 1.7H), 4.62-4.50 (m, 2H), 4.47-4.35 (m, 2.3H), 4.27 (t, J=7.2 Hz, 1H), 4.20-4.16 (m, 1.4H), 3.74 (s, 3H), 3.72-3.64 (m, 1.3H), 3.60-3.54 (m, 1H), 3.26-3.07 (m, 1H), 3.02-2.90 (m, 4H), 2.83-2.77 (m, 2H), 2.77-2.60 (m, 4H), 2.50-2.46 (m, 0.7H), 2.39-2.19 (m, 4H), 2.18-1.90 (m, 6.3H), 1.87-1.78 (m, 1H), 1.73 (br m, 1H), 1.61 (br m, 0.7H), 1.55-1.49 (m, 1H), 1.42-1.38 (m, 1H), 1.27-1.21 (m, 3H), 1.00-0.84 (m, 19.1H), 0.68 (d, J=6.4 Hz, 0.9H) ppm. $^{13}$C NMR (100 MHz, CDCl$_3$, mixture of rotamers): δ 172.7, 172.1, 172.0, 171.9, 171.6, 171.6, 170.8, 158.7, 154.8, 154.4, 144.3, 144.2, 144.1, 143.9, 141.4, 141.3, 131.8, 131.1, 130.5, 130.4, 128.2, 128.2, 127.8, 127.8, 127.2, 127.1, 127.1, 126.4, 125.5, 125.4, 125.3, 120.1, 118.8, 114.0, 79.6, 79.1, 77.4, 75.9, 75.7, 67.9, 67.7, 66.1, 65.5, 60.6, 59.6, 59.4, 55.3, 50.4, 49.8, 49.2, 47.3, 47.1, 46.6, 38.7, 38.2, 37.9, 37.2, 37.1, 36.8, 34.8, 34.5, 33.7, 33.4, 32.1, 31.7, 31.5, 31.1, 31.0, 30.7, 30.2, 29.8, 29.6, 29.5, 28.8, 26.1, 25.1, 24.6, 23.5, 22.8, 21.1, 20.7, 16.2, 15.9, 14.5, 14.4, 14.3, 11.8, 10.7 ppm. HRMS (ESI) m/z calcd for $C_{61}H_{83}N_5O_{11}SNa$ $(M+Na)^+$ 1116.5702, found 1116.5742.

BI: (28.3 mg, 90%). $[\alpha]^{20}_D$ −130.0 (c 0.10, $CH_2Cl_2$). $^1H$ NMR (400 MHz, $CDCl_3$, mixture of rotamers): δ 7.76-7.73 (m, 2H), 7.65-7.59 (m, 2H), 7.40-7.36 (m, 2H), 7.31-7.26 (m, 2H), 7.10-7.08 (m, 2H), 6.85 (d, J=8.4 Hz, 0.3H), 6.77-6.74 (m, 2H), 6.65 (d, J=8.0 Hz, 0.7H), 5.92-5.82 (m, 1H), 5.37 (dddd, J=6.8, 6.8, 6.8, 6.8 Hz, 1H), 5.31-5.20 (m, 2H), 5.20-5.14 (m, 1H), 4.93-4.87 (m, 1.7H), 4.81 (d, J=10.8 Hz, 0.3H), 4.62-4.51 (m, 3H), 4.46-4.41 (m, 2H), 4.33-4.24 (m, 3H), 3.74 (s, 3H), 3.68-3.62 (m, 1.3H), 3.60-3.48 (m, 1.7H), 3.18 (ddd, J=18.8, 10.8, 8.8 Hz, 1H), 3.03-2.95 (m, 4H), 2.82-2.73 (m, 2H), 2.68 (s, 2.1H), 2.65 (s, 0.9H), 2.43-2.17 (m, 4H), 2.15-1.86 (m, 5H), 1.85-1.75 (m, 2H), 1.70-1.55 (m, 2.3H), 1.50-1.45 (m, 0.7H), 1.35-1.17 (m, 13H), 0.97-0.91 (m, 6H), 0.91-0.82 (m, 14.1H), 0.76 (d, J=6.4 Hz, 0.9H) ppm. $^{13}C$ NMR (100 MHz, $CDCl_3$, mixture of rotamers): δ 178.8, 178.3, 173.0, 172.7, 172.3, 172.2, 171.9, 171.6, 171.6, 171.4, 170.8, 169.7, 158.6, 154.9, 154.6, 144.6, 144.3, 144.0, 143.9, 141.4, 141.4, 141.3, 131.8, 130.5, 130.5, 130.4, 128.4, 128.3, 127.8, 127.7, 127.1, 125.5, 125.4, 125.4, 125.3, 120.0, 120.0, 118.8, 113.9, 79.4, 78.7, 77.4, 76.1, 75.7, 75.2, 75.0, 68.0, 67.7, 66.1, 65.5, 64.6, 60.5, 59.8, 59.6, 55.3, 53.6, 50.4, 49.8, 49.3, 47.3, 47.2, 47.1, 46.6, 45.9, 45.4, 38.1, 37.9, 37.0, 36.6, 34.8, 34.7, 34.5, 33.7, 33.5, 33.3, 32.0, 31.7, 31.3, 31.0, 31.0, 30.9, 30.6, 30.1, 29.8, 26.1, 25.6, 25.4, 25.1, 24.6, 24.0, 23.7, 23.5, 22.8, 20.8, 20.7, 20.6, 16.2, 15.9, 15.0, 14.9, 14.4, 14.3, 11.7, 10.7 ppm. HRMS (ESI) m/z calcd for $C_{63}H_{87}N_5O_{11}SNa$ $(M+Na)^+$ 1144.6015, found 1144.6041.

BJ: (22.0 mg, 71%). $[\alpha]^{20}_D$ −66.0 (c 0.05, $CH_2Cl_2$). $^1H$ NMR (400 MHz, $CDCl_3$, mixture of rotamers): δ 7.77-7.74 (m, 2H), 7.65-7.60 (m, 2H), 7.39 (dd, J=7.6, 7.2 Hz, 2H), 7.30 (dd, J=7.2, 6.8 Hz, 2H), 7.10-7.07 (m, 2H), 6.78-6.75 (m, 2H), 5.92-5.81 (m, 1H), 5.39-5.35 (m, 1H), 5.31-5.21 (m, 2H), 5.18-5.11 (m, 1H), 4.93-4.81 (m, 2H), 4.62-4.53 (m, 2H), 4.46-4.21 (m, 5H), 3.81-3.69 (m, 4H), 3.69-3.60 (m, 1H), 3.58-3.49 (m, 1H), 3.22-3.18 (m, 1H), 3.03-2.88 (m, 4H), 2.82-2.76 (m, 3H), 2.71-2.57 (m, 4H), 2.34-2.21 (m, 4H), 2.11-1.79 (m, 8H), 1.71 (br m, 1H), 1.64-1.58 (m, 1H), 1.34-1.18 (m, 5H), 0.97-0.78 (m, 21H) ppm. $^{13}C$ NMR (100 MHz, $CDCl_3$, mixture of rotamers): δ 175.1, 174.6, 173.2, 172.9, 172.7, 172.6, 172.3, 172.2, 172.0, 172.0, 171.9, 171.9, 171.8, 171.6, 171.5, 171.4, 170.8, 169.7, 158.7, 158.6, 155.1, 155.0, 154.5, 144.5, 144.4, 144.3, 144.2, 144.1, 144.0, 143.9, 141.4, 141.4, 141.3, 131.8, 130.5, 128.5, 128.3, 128.0, 127.8, 127.1, 125.5, 125.4, 125.4, 125.3, 120.0, 118.8, 114.0, 113.9, 79.7, 78.8, 77.4, 76.2, 75.9, 75.6, 71.8, 70.9, 70.3, 67.9, 67.8, 67.6, 66.1, 65.5, 60.5, 59.8, 59.7, 59.7, 55.3, 50.4, 49.9, 47.3, 47.3, 47.2, 47.1, 46.6, 45.8, 45.2, 45.0, 40.8, 39.8, 39.6, 38.1, 37.8, 37.7, 37.3, 37.3, 34.8, 34.7, 33.5, 33.4, 32.1, 31.7, 31.4, 31.0, 31.0, 30.7, 30.6, 30.1, 30.1, 29.8, 26.1, 25.7, 25.4, 25.2, 25.1, 24.6, 23.4, 22.8, 20.7, 20.6, 16.8, 16.4, 15.9, 14.4, 14.4, 14.3, 13.9, 11.8, 11.6, 10.7 ppm. HRMS (ESI) m/z calcd for $C_{62}H_{85}N_5O_{11}SNa$ $(M+Na)^+$ 1130.5859, found 1130.5905.

Example 13: General Procedure for the Preparation of BK, BL, BM, and BN

To a solution of cyclic precursor BG, BH, BI, or BJ (11.6 μmol) in THF (1.0 mL) were added $Pd(PPh_3)_4$ (2.7 mg, 2.32 μmol), and N-methylaniline (6.3 μL, 58.0 μmol) at room temperature under argon. This reaction was protected with aluminum foil. After being stirred at the same temperature for 1 h, the reaction mixture was concentrated in vacuo and purified by preparative TLC plate (developed with MeOH/$CH_2Cl_2$ 1:9, v/v) to give the free acid cyclic precursor.

To the solution of free acid cyclic precursor in MeCN (1.5 mL) was added N,N-diethylamine (0.75 mL). After being stirred at room temperature for 30 min, the reaction mixture was evaporated in vacuo, azeotroped with toluene (three times) and $CH_2Cl_2$ (two times) and then dried under reduced pressure for 1 h to give the unmasked precursor as a foam solid. Then the unmasked precursor was dissolved in $CH_2Cl_2$ (DMF for BH) (20 mL). To this solution was added DIEA (20.0 μL, 0.116 mmol) and the corresponding coupling reagent (34.8 μmol) at 0° C. (PyAOP for BK, BM, BN and DEPBT for BL). After being stirred at 0° C. for 30 min, the reaction was allowed to warm up to room temperature and stirred for additional 15 h. Then the reaction was concentrated in vacuo and purified by semipreparative reversed-phase HPLC (Phenomenex Ultracarb, ODS 250× 10 mm, 5 μm, 3.0 mL/min, UV detection at 200/220 nm) using an isocratic system of 80% aqueous MeCN for 30 min, 80-100% MeCN for 30-40 min, and 100% MeCN for 40-60 min to afford BK, BL, BM, or BN.

Apratoxin S4 (BK) (5.7 mg, 60% in 3 steps). $^1H$ NMR (600 MHz, $CDCl_3$, mixture of rotamers, major and minor (7/3)): δ 7.13 (d, J=8.4 Hz, 1.4H), 7.12 (d, J=8.4 Hz, 0.6H), 6.80 (d, J=8.4 Hz, 0.6H), 6.78 (d, J=8.4 Hz, 1.4H), 6.17 (d, J=9.0 Hz, 0.3H), 5.80 (d, J=9.6 Hz, 0.7H), 5.27 (d, J=11.4 Hz, 0.7H), 5.14 (ddd, J=10.2, 10.2, 4.8 Hz, 1H), 4.96 (dd, J=12.6, 2.4 Hz, 0.7H), 4.89 (d, J=11.4 Hz, 0.3H), 4.87 (dd, J=12.6, 2.4 Hz, 0.3H), 4.62 (q, J=6.6 Hz, 0.3H), 4.52 (d, J=10.8 Hz, 0.7H), 4.36-4.32 (m, 0.7H), 4.31-4.27 (m, 0.7H), 4.21 (t, J=7.8 Hz, 1H), 4.20-4.17 (m, 0.3H), 4.10-4.07 (m, 0.3H), 3.81 (d, J=10.8 Hz, 0.3H), 3.76 (s, 2.1H), 3.76 (s, 0.9H), 3.70-3.66 (m, 0.7H), 3.65-3.61 (m, 0.3H), 3.60-3.53 (m, 1H), 3.31 (dd, J=10.8, 8.4 Hz, 0.7H), 3.29 (q, J=6.6 Hz, 0.7H), 3.23 (dd, J=10.8, 8.4 Hz, 0.3H), 3.09 (dd, J=12.0, 11.4 Hz, 1H), 3.01 (dd, J=10.8, 4.8 Hz, 1H), 2.96 (dd, J=12.6, 4.2 Hz, 0.3H), 2.88 (s, 0.9H), 2.80 (s, 2.1H), 2.77 (dd, J=12.6, 4.8 Hz, 0.7H), 2.72 (s, 2.1H), 2.64 (dq, J=9.9, 6.6 Hz, 0.3H), 2.61 (s, 0.9H), 2.59 (dq, J=9.9, 6.6 Hz, 0.7H), 2.48 (ddd, J=14.7, 12.9, 3.6 Hz, 0.7H), 2.39-2.34 (m, 1H), 2.30-2.21 (m, 2H), 2.13 (br m, 1H), 2.08-2.04 (m, 0.7H), 1.94-1.84 (m, 3.3H), 1.82-1.74 (m, 3H), 1.57-1.50 (m, 1.4H), 1.42-1.37 (m, 0.3H), 1.30-1.24 (m, 1H), 1.22 (d, J=6.6 Hz, 2.1H), 1.20-1.18 (m, 0.3H), 1.12-1.09 (m, 0.3H), 1.07 (d, J=7.2H, 0.9H), 1.06 (d, J=7.2 Hz, 0.9H), 1.03 (d, J=7.2 Hz, 2.1H), 1.03 (t, J=7.2 Hz, 2.1H), 1.00 (d, J=6.6 Hz, 2.1H), 0.98 (d, J=6.6 Hz, 2.1H), 0.97 (d, J=7.2 Hz, 0.9H), 0.95-0.90 (m, 0.7H), 0.87 (s, 9H), 0.84 (t, J=7.2 Hz, 0.9H), 0.54 (d, J=6.6 Hz, 0.9H) ppm. $^{13}C$ NMR (150 MHz, $CDCl_3$, mixture of rotamers, major and minor): δ 176.1, 175.2, 172.6, 172.1, 172.0, 171.2, 170.6, 170.4, 170.2, 169.9, 158.9, 158.7, 130.7, 130.6, 128.7, 128.5, 114.2, 114.0, 78.0, 77.5, 75.6, 75.2, 72.5, 71.7, 60.7, 59.8, 59.3, 57.9, 57.1, 55.5, 55.4, 53.8, 51.0, 49.8, 49.0, 47.9, 39.9, 39.0, 38.0, 37.8, 37.5, 37.5, 37.4, 36.9, 35.9, 35.1, 35.0, 34.6, 34.0, 33.7, 33.7, 32.6, 31.5, 30.7, 30.7, 30.7, 29.8, 29.3, 29.3, 28.9, 26.3, 26.2, 25.7, 25.5, 25.2, 25.1, 24.5, 20.7, 20.0, 16.6, 16.5, 15.0, 14.3, 14.1, 14.1, 9.9, 9.7 ppm.

Apratoxin S7 (BL) (2.3 mg, 25% in 3 steps). $[\alpha]^{20}_D$ −106.2 (c 0.024, $CH_2Cl_2$). $t_R$=17.5 min. $^1H$ NMR (600 MHz, $CDCl_3$, mixture of rotamers, major and minor (6/4)): δ 7.14 (d, J=8.4 Hz, 1.2H), 7.10 (d, J=8.4 Hz, 0.8H), 6.80 (d, J=8.4 Hz, 0.8H), 6.79 (d, J=8.4 Hz, 1.2H), 6.17 (d, J=9.0 Hz, 0.4H), 5.78 (d, J=10.2 Hz, 0.6H), 5.26 (d, J=11.4 Hz, 0.6H), 5.20-5.16 (m, 0.4H), 5.15 (ddd, J=15.0, 10.2, 4.8 Hz, 0.6H), 4.96 (dd, J=12.6, 2.4 Hz, 0.6H), 4.89 (d, J=11.4 Hz, 0.4H), 4.87 (dd, J=12.6, 2.4 Hz, 0.4H), 4.64 (q, J=6.6 Hz, 0.4H), 4.60 (d, J=10.8 Hz, 0.6H), 4.38-4.31 (m, 1.2H), 4.24-4.19 (m, 1H), 4.11-4.08 (m, 0.4H), 4.05 (br m, 0.4H), 4.00-3.95 (m, 0.6H), 3.90 (br m, 0.4H), 3.77 (s, 1.8H), 3.77 (s, 1.2H), 3.70-3.66 (m, 0.6H), 3.65-3.61 (m, 0.4H), 3.39 (dd, J=10.8, 8.4 Hz, 0.6H), 3.32 (dd, J=10.8, 8.4 Hz, 0.4H), 3.29 (q, J=6.6 Hz, 0.6H), 3.09 (dd, J=12.0, 11.4 Hz, 1H), 3.05-3.01 (m, 1H), 2.94 (dd, J=12.6, 4.2 Hz, 0.4H), 2.88 (s, 1.2H), 2.80 (s, 1.8H), 2.77 (dd, J=12.6, 4.8 Hz, 0.6H), 2.74 (s, 1.8H), 2.64-2.58 (m, 1.8H), 2.52 (dd, J=13.5, 11.4 Hz, 0.6H), 2.45-2.32 (m, 1.6H), 2.31-2.23 (m, 1.6H), 2.15-1.96 (m, 2.4H), 1.96-1.83 (m, 3.6H), 1.81-1.69 (m, 4H), 1.62 (ddd, J=13.8, 9.6, 3.6 Hz, 1H), 1.56-1.51 (m, 1H), 1.31-1.25 (m, 1H), 1.23 (d, J=7.2 Hz, 1.8H), 1.21-1.17 (m, 0.4H), 1.09 (d, J=6.6 Hz, 1.2H), 1.03 (t, J=6.6 Hz, 1.8H), 1.03 (d, J=6.6 Hz, 1.8H), 1.00 (d, J=6.6 Hz, 1.2H), 0.98 (d, J=6.6 Hz, 1.2H), 0.98-0.92 (m, 0.6H), 0.87 (s, 9H), 0.84 (t, J=7.2 Hz, 1.2H), 0.57 (d, J=6.6 Hz, 1.2H) ppm. $^{13}$C NMR (150 MHz, CDCl$_3$, mixture of rotamers, major and minor): δ 172.7, 172.1, 171.9, 171.2, 170.7, 170.5, 170.3, 170.2, 170.0, 168.6, 158.8, 158.7, 130.7, 130.6, 128.7, 128.5, 114.2, 114.0, 78.1, 77.6, 76.2, 75.8, 68.6, 67.3, 60.7, 59.9, 59.5, 58.1, 57.9, 57.4, 55.5, 55.4, 54.1, 50.9, 49.8, 47.8, 45.0, 43.9, 42.9, 41.0, 39.8, 38.8, 37.6, 37.5, 37.4, 37.0, 36.9, 34.1, 34.1, 33.2, 33.0, 31.5, 30.6, 30.6, 29.3, 29.3, 29.0, 26.2, 26.2, 25.7, 25.6, 25.3, 25.2, 24.8, 20.9, 19.9, 15.1, 14.3, 14.1, 14.1, 10.0, 10.0 ppm. HRMS (ESI) n/z calcd for $C_{43}H_{67}N_5O_8SNa$ (M+Na)$^+$ 836.4603, found 836.4607.

Apratoxin S8 (BM) (6.8 mg, 70% in 3 steps). [α]$^{20}_D$ −59.5 (c 0.037, CH$_2$Cl$_2$). $t_R$=26.2 min. $^1$H NMR (600 MHz, CDCl$_3$, mixture of rotamers, major and minor (7/3)): δ 7.14 (d, J=8.4 Hz, 0.6H), 7.12 (d, J=8.4 Hz, 1.4H), 6.80 (d, J=8.4 Hz, 1.4H), 6.78 (d, J=8.4 Hz, 0.6H), 6.18 (d, J=9.0 Hz, 0.7H), 5.73 (d, J=10.2 Hz, 0.3H), 5.27 (d, J=11.4 Hz, 0.3H), 5.18-5.11 (m, 1H), 4.96 (d, J=12.0 Hz, 0.3H), 4.89 (d, J=10.8 Hz, 1H), 4.60 (q, J=6.0 Hz, 0.7H), 4.45-4.37 (m, 1H), 4.35-4.31 (m, 0.7H), 4.15 (t, J=8.4 Hz, 0.3H), 4.10-4.06 (m, 0.7H), 3.87 (d, J=10.8 Hz, 0.7H), 3.76 (s, 3H), 3.70 (t, J=10.8 Hz, 0.7H), 3.63-3.59 (m, 1H), 3.34 (dd, J=10.8, 8.4 Hz, 0.3H), 3.31 (q, J=6.6 Hz, 0.3H), 3.24 (dd, J=10.8, 8.4 Hz, 0.7H), 3.12 (dd, J=12.6, 11.4 Hz, 0.3H), 3.09-3.04 (m, 1.4H), 2.95 (dd, J=12.6, 3.6 Hz, 0.7H), 2.88 (s, 2.1H), 2.87 (s, 0.9H), 2.76 (s, 0.9H), 2.75-2.73 (m, 0.3H), 2.58 (s, 2.1H), 2.41 (ddd, J=13.2, 13.2, 4.8 Hz, 0.7H), 2.36-2.26 (m, 2.3H), 2.23-2.18 (m, 1H), 2.14-2.10 (br m, 0.7H), 2.08-2.02 (m, 1.3H), 1.98-1.91 (m, 3.3H), 1.89-1.82 (m, 2.3H), 1.78-1.73 (m, 3.3H), 1.60-1.56 (m, 0.7H), 1.51 (m, 1H), 1.29-1.23 (m, 2.8H), 1.17 (s, 0.9H), 1.16 (s, 2.1H), 1.07-1.06 (m, 5.1H), 1.03 (t, J=7.2 Hz, 0.9H), 0.98 (d, J=6.6 Hz, 3H), 0.87 (s, 9H), 0.83 (t, J=7.2 Hz, 2.1H), 0.49 (d, J=6.6 Hz, 2.1H) ppm. $^{13}$C NMR (150 MHz, CDCl$_3$, mixture of rotamers, major and minor): δ 179.6, 178.4, 172.2, 172.0, 172.0, 171.8, 170.9, 170.4, 170.3, 170.2, 170.1, 169.8, 158.9, 158.6, 130.7, 130.6, 128.7, 128.5, 114.2, 113.9, 77.7, 75.8, 75.3, 74.8, 73.9, 60.8, 60.0, 59.3, 57.8, 57.4, 55.5, 55.4, 54.2, 50.9, 49.8, 47.8, 46.7, 46.5, 40.0, 38.2, 38.0, 37.6, 37.3, 37.0, 36.0, 35.2, 35.1, 34.9, 34.6, 34.1, 33.7, 31.7, 31.4, 30.8, 30.8, 30.7, 29.8, 29.5, 29.3, 28.9, 26.3, 26.3, 25.8, 25.6, 25.6, 25.5, 25.3, 25.0, 24.2, 22.8, 20.7, 20.3, 18.7, 18.3, 14.9, 14.6, 14.3, 14.1, 14.1, 10.7, 10.0 ppm. HRMS (ESI) m/z calcd for $C_{45}H_{71}N_5O_8SNa$ (M+Na)$^+$ 864.4916, found 864.4918.

Apratoxin S9 (BN) (4.3 mg, 45% in 3 steps). [α]$^{20}_D$ −82.6 (c 0.023, CH$_2$Cl$_2$). $t_R$=24.8 min. $^1$H NMR (600 MHz, CDCl$_3$, mixture of rotamers, major and minor (6/4)): δ 7.13 (d, J=9.0 Hz, 1.2H), 7.13 (d, J=9.0 Hz, 0.8H), 6.82 (d, J=9.0 Hz, 0.8H), 6.79 (d, J=9.0 Hz, 1.2H), 6.23 (d, J=8.4 Hz, 0.4H), 5.86 (d, J=9.6 Hz, 0.6H), 5.23 (d, J=11.4 Hz, 0.6H), 5.19 (ddd, J=10.5, 10.5, 4.8 Hz, 0.6H), 5.05 (ddd, J=10.8, 8.4, 4.2 Hz, 0.4H), 4.95 (dd, J=13.2, 3.0 Hz, 0.6H), 4.88 (dd, J=12.6, 3.6 Hz, 0.4H), 4.82 (d, J=11.4 Hz, 0.4H), 4.73 (d, J=11.4 Hz, 0.6H), 4.59 (q, J=6.6 Hz, 0.4H), 4.23 (qd, J=8.4, 4.8 Hz, 0.4H), 4.36-4.34 (m, 0.4H), 4.31-4.23 (m, 1H), 4.23 (t, J=7.8 Hz, 0.6H), 4.19 (d, J=10.2 Hz, 0.4H), 4.13-4.09 (m, 0.4H), 3.77 (s, 1.8H), 3.77 (s, 1.2H), 3.69-3.64 (m, 0.6H), 3.64-3.60 (m, 0.4H), 3.55-3.51 (m, 0.4H), 3.50 (dd, J=10.8, 7.8 Hz, 0.4H), 3.46 (qd, J=11.1, 3.6 Hz, 0.6H), 3.38 (dd, J=10.8, 7.8 Hz, 0.6H), 3.26 (q, J=6.6 Hz, 0.6H), 3.09-2.98 (m, 1.4H), 2.94 (s, 1.2H), 2.80-2.76 (m, 1.6H), 2.74 (s, 1.8H), 2.74 (s, 1.8H), 2.70 (dd, J=11.4, 11.4 Hz, 0.6H), 2.63-2.57 (m, 2.2H), 2.44 (ddd, J=16.8, 5.4, 3.0 Hz, 0.6H), 2.41-2.34 (m, 1H), 2.30-2.22 (m, 1.2H), 2.20-2.17 (m, 0.4H), 2.16-2.10 (m, 1H), 2.09-2.03 (m, 1.4H), 1.98-1.84 (m, 2.4H), 1.79 (td, J=13.2, 3.6 Hz, 0.6H), 1.75-1.61 (m, 4.4H), 1.58-1.52 (m, 0.6H), 1.49 (td, J=11.4, 3.6 Hz, 0.6H), 1.33 (ddd, J=13.8, 11.1, 3.0 Hz, 0.4H), 1.29-1.26 (m, 1.4H), 1.23 (d, J=7.2 Hz, 1.8H), 1.12-1.09 (m, 2.2H), 1.07 (d, J=6.6H, 1.8H), 1.05 (d, J=7.2 Hz, 1.8H), 1.01 (t, J=7.2 Hz, 1.8H), 0.97-0.95 (m, 3.6H), 0.92 (m, 0.4H), 0.87 (s, 5.4H), 0.87 (s, 3.6H), 0.85 (t, J=7.2 Hz, 1.2H), 0.43 (d, J=6.6 Hz, 1.2H) ppm. $^{13}$C NMR (150 MHz, CDCl$_3$, mixture of rotamers, major and minor): δ 175.3, 174.9, 172.6, 172.2, 171.9, 171.4, 171.1, 170.7, 170.5, 170.3, 170.0, 158.9, 158.7, 130.7, 130.5, 128.7, 128.4, 114.3, 114.0, 78.0, 77.6, 75.5, 74.9, 72.5, 72.1, 60.7, 59.8, 59.3, 58.3, 56.9, 55.5, 55.4, 53.8, 51.6, 49.6, 49.0, 47.8, 47.5, 40.0, 39.4, 38.3, 38.0, 37.8, 37.6, 37.5, 37.1, 36.8, 35.2, 35.2, 34.2, 34.0, 33.2, 32.5, 31.6, 31.1, 30.8, 30.5, 29.3, 29.2, 28.8, 26.2, 25.8, 25.7, 25.3, 25.2, 24.8, 24.7, 20.6, 20.1, 16.5, 16.4, 14.6, 14.3, 14.0, 14.0, 10.1, 9.9 ppm. HRMS (ESI) m/z calcd for $C_{44}H_{69}N_5O_8SNa$ (M+Na)$^+$ 850.4759, found 850.4773.

Example 14: Cell Culture

Human colon adenocarcinoma HCT116 cells were purchased from ATCC (Manassas, Va.) and cultured in Dulbecco's modified Eagle's medium (Invitrogen, Carlsbad, Calif.) supplemented with 10% fetal bovine serum (HyClone, Logan, Utah) at 37° C. humidified air and 5% CO$_2$.

Example 15: Cell Viability Assay (MTT)

HCT116 cells were seeded at a density of 1×10$^4$ cells per well in 96-well plates. 24 h later the cells were treated with various concentrations of apratoxins or solvent control. After 48 h of incubation, cell viability was detected using MTT according to the manufacturer's instructions (Promega, Madison, Wis.).

Example 16: Measurement of VEGF-A Production

HCT116 cells (1×10$^4$ cells per well) were seeded in 96-well plates and one day later treated with various concentrations of apratoxins or solvent control. After 12 h of incubation, culture supernatants were collected for detection of VEGF-A by using an alphaLISA kit (PerkinElmer, Waltham, Mass.) following the manufacturer's instructions. Briefly, acceptor bead and anti-VEGF antibody were incubated first with the supernatants for 60 min, donor beads were added later and incubated for another 30 min and then VEGF-A levels detected using Envision (PerkinElmer).

Example 16: Immunoblot Analysis

HCT116 cells were seeded in 6-well plates at a density of $4\times10^5$ cells and the next day treated with various concentrations of apratoxins or solvent control. 24 h later, whole cell lysates were collected using PhosphoSafe buffer (EMD Chemicals, Inc, Gibbstown, N.J.). The protein concentration was measured with the BCA Protein Assay kit (Thermo Fisher Scientific, Rockford, Ill.). Lysates containing equal amounts of protein were separated by SDS polyacrylamide gel electrophoresis (4-12%), transferred to polyvinylidene difluoride membranes, probed with primary and secondary antibodies, and detected with the SuperSignal West Femto Maximum Sensitivity Substrate (Thermo Fisher Scientific). Anti-Met and secondary anti-mouse antibodies were from Cell Signaling Technology, Inc. (Danvers, Mass.).

Example 17: In Vivo Efficacy Studies 3-5 week old female nude mice (nu/nu) were obtained from Charles River Laboratory (Wilmington, Mass.). $1\times10^6$ HCT116 cells in a volume of 100 µL of sterile saline were injected subcutaneously on the left rear flank of a nude mouse to establish tumors. Tumor dimensions were measured using calipers every day and tumor volumes were calculated using the formula $W^2\times L\times 0.5$, where width (W)≤length (L). Tumors with a starting volume bigger than 100 mm³ were excluded from the analysis. Mice were injected intraperitoneally with the doses of 2 µg/mouse (0.1 mg/kg), 5 µg/mouse (0.25 mg/kg) of apratoxin S8 (BM) or solvent (DMSO) control every day until the tumor size in one dimension reached 15 mm and tumor tissue was harvested on the following day. 50 mg of tumor tissue was sonicated in PhosphoSafe lysis buffer (EMD chemicals, Inc) and used for immunoblot analysis described as the above. All studies were carried out under the protocol approved by the Institutional Animal Care and Use Committee at the University of Florida.

Example 18: Metabolite Analyses

Materials and General Procedures.
HPLC-MS was done on a 3200 QTRAP (Applied Biosystems) equipped with a Shimadzu (Kyoto, Japan) UFLC System. Mouse serum and harmine were purchased from Sigma-Aldrich. Pooled CD1 mouse liver (female) microsomes were purchased from XenoTech, LCC (Lenexa, Kans.) with protein concentrations of 0.5 mg/ml. HCT116 cell lysates were prepared with PhosphoSafe lysis buffer (Novagen). Protein concentration was determined by using the BCA Assay. Analysis was carried out similarly as previously described [Liu, Y.; Salvador, L. A.; Byeon, S.; Ying, Y.; Kwan, J. C.; Law, B. K.; Hong, J.; Luesch. H. *J. Pharmacol. Exp. Ther.* 2010, 335, 351-361].

Sample Preparation.
Stock solutions of apratoxin A, S4 (BK), S7 (BL), S8 (BM) and S9 (BN) were prepared by dissolving the compounds in ethanol to give a 1 mg/mL solution. Aliquots of this stock solution were then obtained to afford a 40 µg/mL solution in acetonitrile. Serial dilution of the 40 µg/mL solution in acetonitrile gave standard solutions with concentrations of 25, 12.5, 2.5, 1.25, 0.25, 0.125, 0.025, and 0.0125 µg/mL. A 1-mg/mL stock solution of the internal standard harmine was prepared in ethanol, which subsequently used to prepare 100 µg/mL solution with ethanol. An aliquot of the 100 µg/mL harmine solution was diluted to 35 ng/ml with ethyl acetate to serve as the working internal standard solution.

Plasma Stability.
In vitro plasma stability of apratoxin A, S4 (BK), S7 (BL), S8 (BM) and S9 (BN) was done by using a modification of a published method [Chen, X.; Gardner, E. R.; Figg, W. D. *J. Chromatogr. B Analyt. Technol. Biomed. Life Sci.* 2008, 86, 153-158]. Ten microliters of apratoxin A, BK, BL, BM, or BN (25 µg/mL) were added to 100 µL of mouse serum, and the solution was vortex-mixed for 15 s and incubated for 0.25 min to 24 h (11 time points). At the end of each incubation period, 400 µL of ethyl acetate was added to each tube, followed by 200 µL of harmine to quench the reaction and to extract the remaining apratoxin A or S4 (BK), S7 (BL), S8 (BM) and S9 (BN). Samples were further incubated in a thermomixer at 27° C. (750 rpm, 5 min) and later centrifuged for 5 min at 1643 g. The ethyl acetate layer was collected and evaporated to dryness under nitrogen. Samples were reconstituted in 50 µL of acetonitrile. A volume of 10 µL of the reconstituted solution was injected into the HPLC-MS system.

Microsomal Stability.
The stability of apratoxin A, S4 (BK), S7 (BL), S8 (BM) and S9 (BN) in the presence of mouse microsomes was determined by using an adaptation of a published procedure [Ackley, D. C.; Rockich, K. T.; Baker, T. R. *Optimization in Drug Discovery: In Vitro Methods* (Series: Methods in Pharmacology and Toxicology) (eds Yan Z, Caldwell J W) 2004, pp 151-162, Springer, New Jersey]. In brief, microsomes were added to prewarmed phosphate buffer (100 mM, pH 7.4) at 37° C. Apratoxin A, BK, BL, BM, or BN (3 µL) were added to the microsomal preparation followed by NADPH cofactor solution (1.3 mM NADP, 3.3 mM glucose 6-phosphate, 0.4 U/mL glucose-6-phosphate dehydrogenase, 3.3 mM $MgCl_2$). The reaction was allowed to proceed for 3 min to 3 h (7 time points) at 37° C. (thermomixer, 1050 rpm). The reaction was quenched by addition of ethyl acetate and subsequently spiked with harmine. The zero time point was defined by denaturing the microsomes with ethyl acetate before the addition of apratoxins. Incubation of apratoxins with microsomes alone was also performed following the same procedure to determine NADPH-dependent metabolism. The final concentration of the incubation mixture contained 0.5 mg/ml protein concentration and 1 µM apratoxins.

Cellular Stability.
Aliquots of HCT116 cell lysates were diluted with 25 mM Tris-HCl buffer, pH 8.0, to give a final reaction volume of 100 µL and protein concentration of 0.7 mg/mL. Cell lysate solutions were incubated with 10 µL of apratoxin A, BK, BL, BM, or BN (25 µg/mL) for 0.25 min to 24 h (nine time points). Remaining apratoxin A, BK, BL, BM, or BN were extracted from the reaction solution at the end of the incubation periods with ethyl acetate using the same procedure as described for the plasma stability assay.

Aqueous Stability.
The stability of apratoxin A, S4 (BK), S7 (BL), S8 (BM) and S9 (BN) in aqueous solution was determined in 100 mM phosphate buffer, pH 4.88, 100 mM phosphate buffer, pH 7.4. Portions of each solution (100 µL) were spiked with 10 µL of apratoxin solution (25 µg/ml) and allowed to incubate for 0.25 min to 24 h (11 time points). The reaction was quenched at the end of each time point, and the remaining apratoxin A, S4 (BK), S7 (BL), S8 (BM) and S9 (BN) were extracted after the ethyl acetate extraction procedure, as in the plasma stability study.

HPLC-Ms Parameters.

Analysis of apratoxin A, S4 (BK), S7 (BL), S8 (BM) and S9 (BN) was done by using HPLC-MS [column, Onyx Monolithic C18 (3.0×100 mm), Phenomenex (Torrance, Calif.); solvent, water (solvent A) acetonitrile (solvent B); flow rate, 0.5 ml/min; detection by electrospray ionization-MS in positive ion mode (MRM scan)]. A stepwise gradient elution was used starting at 60% B and 40% A, then increasing to 80% B at 5 min and maintained at this condition for 5 min. Parameters were optimized before analysis by using direct syringe infusion. The retention times ($t_R$, min; MRM ion pair) of the analytes and internal standard are as follows: harmine (2.2; 213.1→169.9), apratoxin A (4.7; 841.4→445.2), apratoxin S4 (BK) (4.1; 828.5→432.2), apratoxin S7 (BL) (4.05; 814.5→418.2), apratoxin S8 (BM) (5.2; 842.5→446.2), apratoxin S9 (BN) (4.9; 828.5→432.2). Compound-dependent parameters used were as follows: apratoxin A, declustering potential (DP) 51, entrance potential (EP) 12, collision energy (CE) 45, collision cell exit potential (CXP) 6, collision cell entrance potential (CEP) 32; and harmine, DP 56.0, EP 4.5, CE 44.0, CXP 5, CEP 16.0. Source gas parameters used were as follows: curtain gas, 15.0; collision gas low, ionspray voltage 5500; temperature, 600.0; ion source gas 150.0; ion source gas 2 60.0.

Data Analysis.

Calibration curves for apratoxin A, S4 (BK), S7 (BL), S8 (BM) and S9 (BN) in the presence of mouse serum, HCT116 cell lysates, and aqueous solutions were generated by least-square linear regression analysis of the analyte peak area and internal standard peak area ratio against the nominal concentration of the standard solutions. A linear regression analysis was performed, and the concentration of remaining apratoxins at each time point was determined through interpolation for plasma, cellular, and aqueous stability experiments. The amount of remaining apratoxins with microsome incubation was determined from the peak area ratio of apratoxins at $t_x$ (3 min to 3 h) and $t_0$. All calculations were done by using Analyst 1.4.2 (Applied Biosystems) Quantitate Mode.

Structure-Activity Relationships (SAR)

Apratoxins S7-S9 (BL, BM, BN) retained potent activity compared with apratoxin S4 (BK) in all biological assays. The anti-proliferative activities of Apratoxin S4 (BK) and Apratoxins S7-S9 (BL, BM, BN) are shown in Table 5. It has previously been demonstrated that apratoxin A inhibits cotranslational translocation of secretory molecules, including receptors and growth factors, and therefore we measured representative key members of these protein classes when assessing the properties of S7 (BL), S8 (BM) and S9 (BN) [Chen, Q.-Y.; Liu, Y.; Luesch, H. *ACS Med. Chem. Lett.* 2011, 2, 861-865; Liu, Y.; Law, B. K.; Luesch, H. *Mol. Pharmacol.* 2009, 76, 91-104]. The low-nanomolar antiproliferative activity is paralleled by a similar potency in reducing levels of the met proto-oncogene (MET) receptor (FIG. 1), a representative receptor tyrosine kinases (RTK) that is commonly overexpressed in various cancers. We also measured secretion of the angiogenic VEGF-A, which is potently inhibited with even sub-nanomolar activity (300-470 pM) by apratoxins S7 (BL) and S8 (BM) and comparable to the effects of apratoxin S4 (BK) (Table 5). Interestingly, the 30-epi-BK, apratoxin S9 (BN) showed superior, picomolar (sub-nanomolar) potency in all three assays, outperforming the other apratoxins by 2-3 fold (Table 5, FIG. 1).

TABLE 5

Activities of Synthetic Apratoxins on HCT116 Cell Viability and VEGF-A Secretion

| Apratoxin | $IC_{50}$ (nM)[a] cell viability | $IC_{50}$ (nM)[b] VEGF-A secretion |
|---|---|---|
| S4 (BK) | 1.43 | 0.32 |
| S7 (BL) | 1.25 | 0.30 |
| S8 (BM) | 1.99 | 0.47 |
| S9 (BN = C30-epi-BK) | 0.69 | 0.12 |

[a]Determined after 48 h (n = 4).
[b]Determined after 12 h (n = 3).

In Vitro Stability.

Figure 2:
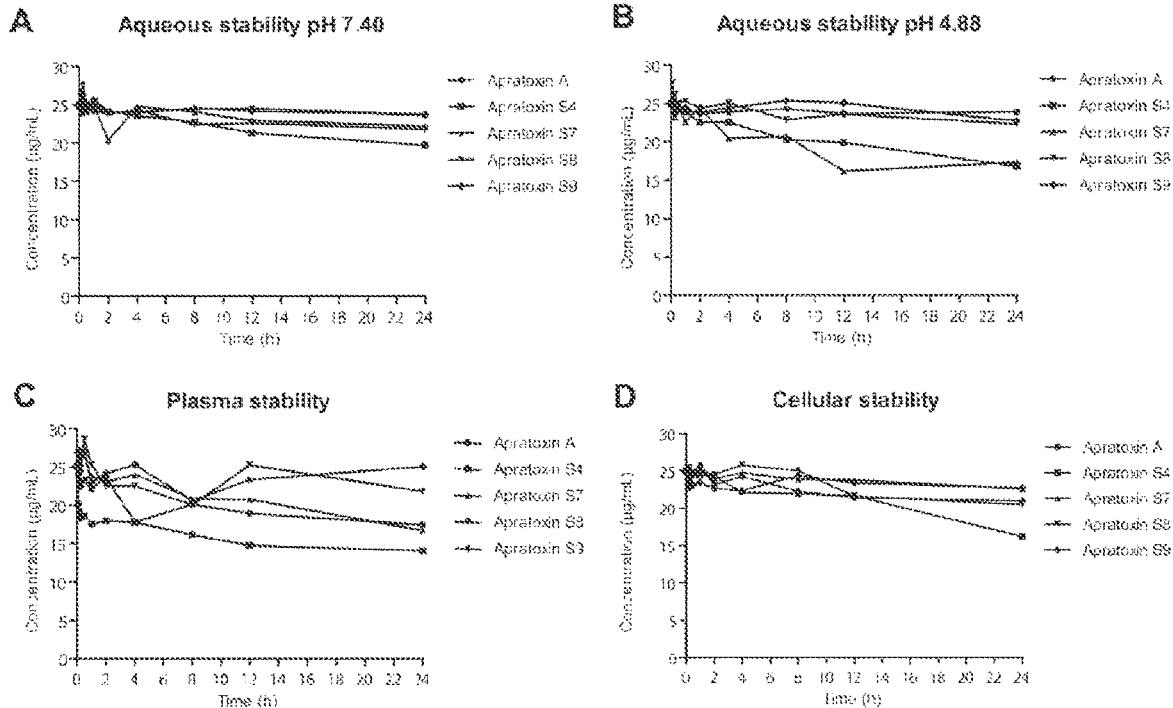
FIG. 2. depicts the in vitro stability of apratoxins under various conditions. Apratoxins were incubated as indicated and extracted with ethyl acetate, subjected to LC-MS and monitored by using compound-specific MRM mode with harmine as internal standard. (A) Stability in aqueous solution, pH 7.40. (B) Stability in aqueous solution, pH 4.88. (C) Stability in mouse serum. (D) Cellular stability up The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.
Figure 3:
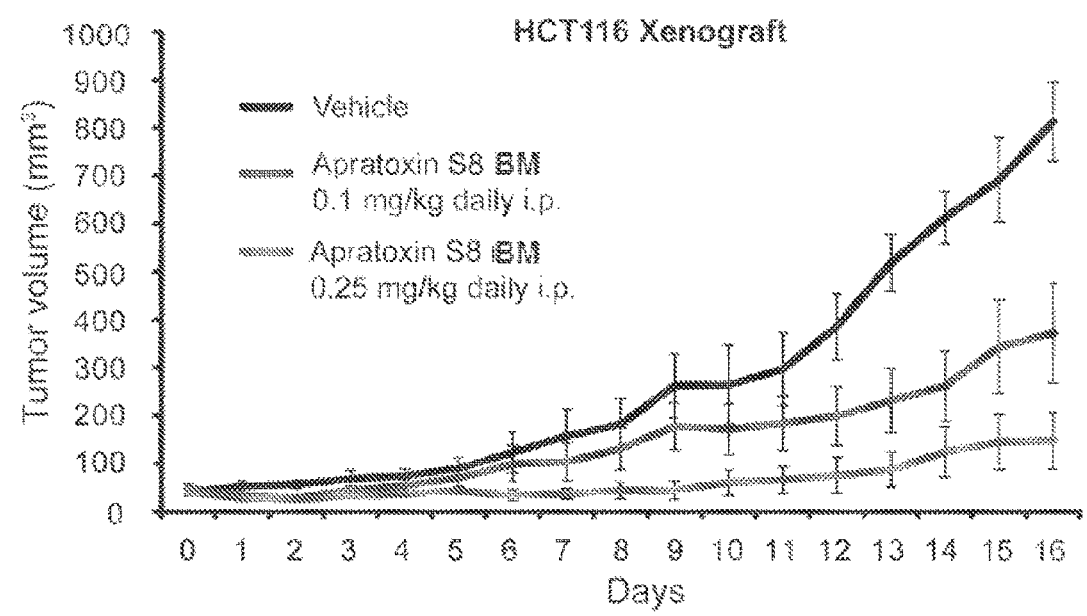

All of BK, BL, BM, BN were remarkably stable ($t_{1/2}$>24 h) under aqueous conditions at physiological (pH 7.4) and lysosomal pH (4.88) (FIGS. 2A,B) and possess excellent plasma and cellular stability (FIGS. 2C,D). Microsomal metabolism of BK, BL, BM, and BN was strongly accelerated by NADPH and stability found to be very low ($t_{1/2}$<5 min, Table 6), which may suggest that primary apratoxin biotransformation products could also retain activity, considering that apratoxin S4 (BK) was extremely potent and active in vivo as well.

TABLE 6

Microsomal stability studies

| time (min) | apratoxin A | | apratoxin S4 (BK) | | apratoxin S7 (BL) | |
|---|---|---|---|---|---|---|
| | microsomes only | microsomes + NADPH | microsomes only | microsomes + NADPH | microsomes only | microsomes + NADPH |
| 0 | 100 | 100 | 100 | 100 | 100 | 100 |
| 3 | 72.75 ± 5.73 | 57.60 ± 7.07 | 87.05 ± 1.63 | 39.55 ± 1.06 | 66.60 ± 12.30 | 54.95 ± 4.74 |
| 5 | 91.35 ± 2.05 | 29.20 ± 2.12 | 70.80 ± 23.48 | 32.20 ± 16.12 | 60.50 ± 2.26 | 18.70 ± 1.41 |
| 15 | 102.45 ± 26.23 | 7.44 ± 2.96 | 87.20 ± 2.83 | 10.07 ± 1.46 | 76.55 ± 9.55 | 52.40 ± 2.40 |
| 30 | 91.00 ± 28.28 | 6.95 ± 1.71 | 73.85 ± 15.49 | 9.58 ± 1.03 | 54.80 ± 1.56 | 6.10 ± 1.96 |
| 60 | 82.55 ± 1.48 | 2.61 ± 0.56 | 87.10 ± 1.41 | 10.00 ± 0.71 | 54.50 ± 0.00 | 5.41 ± 1.09 |
| 120 | 83.60 ± 9.48 | 1.52 ± 0.23 | 55.25 ± 12.09 | 6.02 ± 2.11 | 53.85 ± 9.40 | 4.30 ± 0.82 |

| time (min) | apratoxin S8 (BM) | | apratoxin S9 (BN) | |
|---|---|---|---|---|
| | microsomes only | microsomes + NADPH | microsomes only | microsomes + NADPH |
| 0 | 100 | 100 | 100 | 100 |
| 3 | 74.10 ± 9.62 | 37.20 ± 1.27 | 83.10 ± 0.42 | 51.40 ± 8.06 |
| 5 | 77.45 ± 3.18 | 17.30 ± 2.55 | 71.40 ± 1.27 | 17.80 ± 0.28 |
| 15 | 63.45 ± 3.61 | 8.28 ± 2.86 | 45.25 ± 5.30 | 3.55 ± 0.25 |

TABLE 6-continued

| Microsomal stability studies | | | | |
| --- | --- | --- | --- | --- |
| 30 | 74.75 ± 8.70 | 4.83 ± 1.05 | 56.05 ± 1.06 | 3.73 ± 0.25 |
| 60 | 81.25 ± 1.91 | 3.55 ± 0.91 | 48.45 ± 0.92 | 6.06 ± 2.40 |
| 120 | 70.05 ± 0.78 | 5.01 ± 0.23 | 56.25 ± 0.21 | 5.63 ± 0.18 |

[a] Assays were done in triplicate. Values are expressed as % remaining. Mean values are shown ± S.D.

In Vivo Activity of Apratoxin S8 (BM).

Even though apratoxin S8 (BM) had slightly lower activity than our other synthetic apratoxins, it was still very potent in vitro and had the potential advantage that it cannot dehydrate to form a conjugated system. Therefore, we tested BM for efficacy in the same HCT116 xenograft mouse model as previously performed for apratoxin S4 (BK) and administered BM at the previous efficacious dose for BK (0.25 mg/kg, ~5 μg/mouse) and a 2.5-fold lower dose (0.1 mg/kg, ~2 μg/mouse) daily via intraperitoneal (i.p.) injection for about 2 weeks. There was a clear dose-dependent tumor growth inhibition. The higher dose of BM strongly retarded the tumor growth, paralleling the effects of apratoxin S4 (BK). The lower dose showed a weaker yet pronounced effect (FIG. 3); however, the tumor growth could only be inhibited by about 50% using 0.1 mg/kg. (Of note, we did not observe signs of toxicity based lack of weight loss and abnormal behavior).

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of formula 1:

(1)

or a pharmaceutically acceptable salt thereof;

wherein:

X is S or O;

each Y is independently H or optionally substituted alkyl;

Each R is independently alkyl optionally substituted with OH, OMe, SH, SMe, optionally substituted phenyl, $NH_2$, NH-alkyl, or N(alkyl)(alkyl); or each R is independently the side chain of a naturally-occurring or non-natural amino acid;

or wherein each Y and R and the adjacent atoms attached to them (nitrogen and carbon, respectively) can combine to form a heterocyclic ring;

$R_1$ is optionally substituted alkyl;

$R_2$ is H or optionally substituted alkyl; and $R_3$ is H, optionally substituted alkyl, or —C(O)alkyl.

2. The compound of claim 1, or a pharmaceutically acceptable salt thereof according to formula 3:

(3)

wherein:

each n is independently 0, 1, 2, 3, or 4; and each $R_5$ is independently OH, $OCH_3$, SH, thioalkoxy, alkoxy, halo, $NH_2$, NH-alkyl, or N(alkyl)(alkyl).

3. The compound of claim 1, of any of formulae:

(5)

(7)
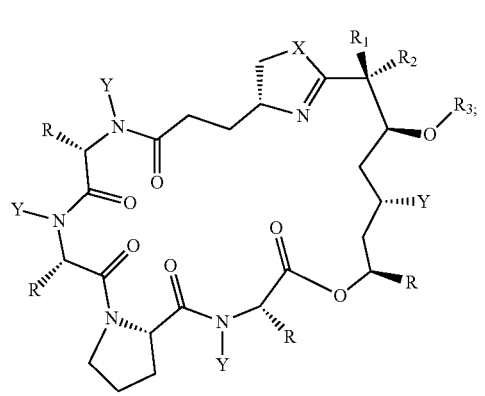
(9)
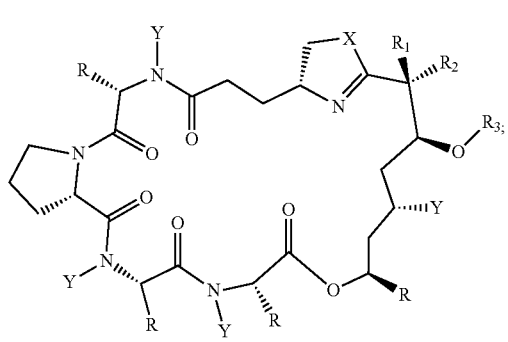
(11)
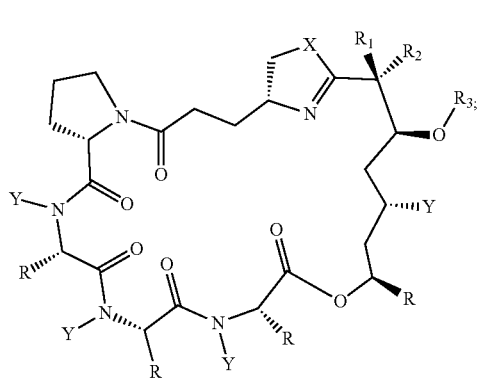
(13)
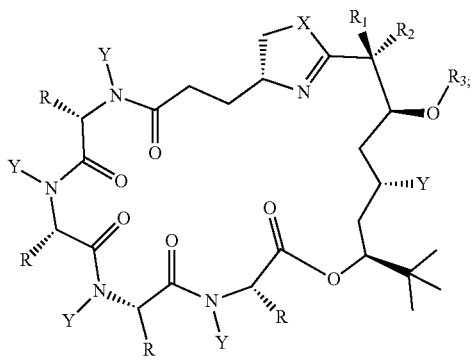
(14)
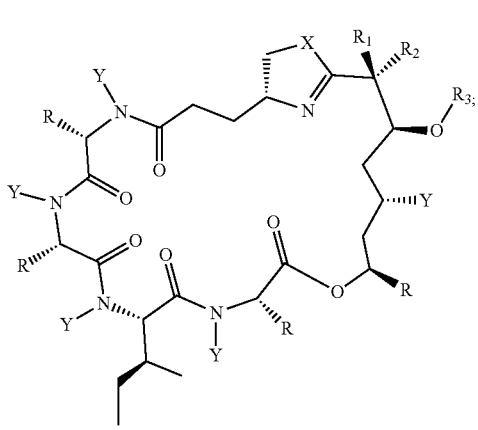
(15)
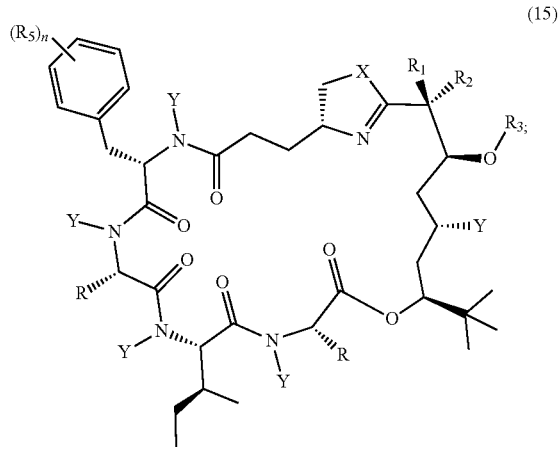
or a pharmaceutically acceptable salt thereof.
4. The compound of claim 1, or a pharmaceutically acceptable salt thereof, wherein X is S.
5. The compound of claim 2, according to formula 15:
(15)
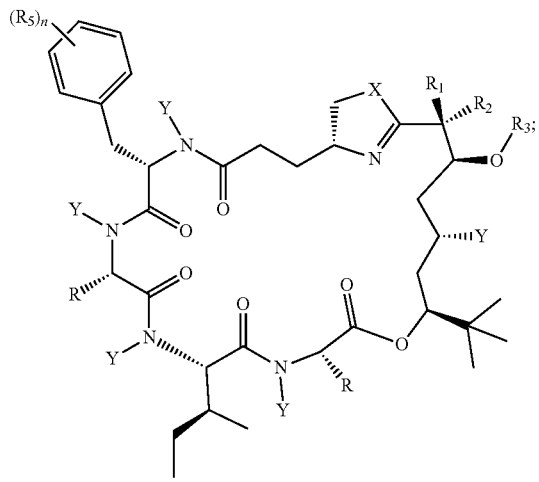
or a pharmaceutically acceptable salt thereof.

6. The compound of claim 1, that is:

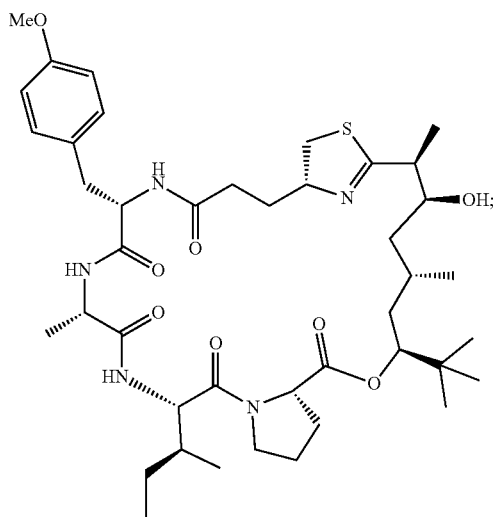

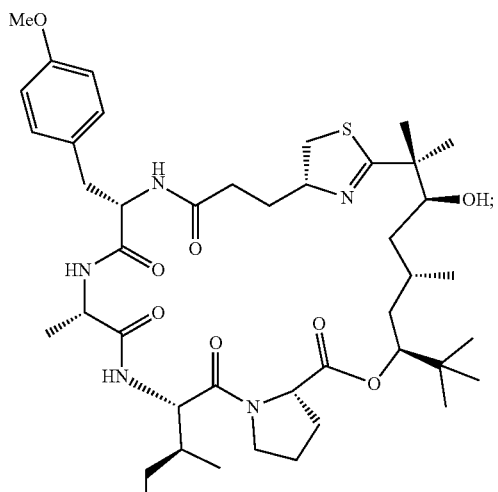

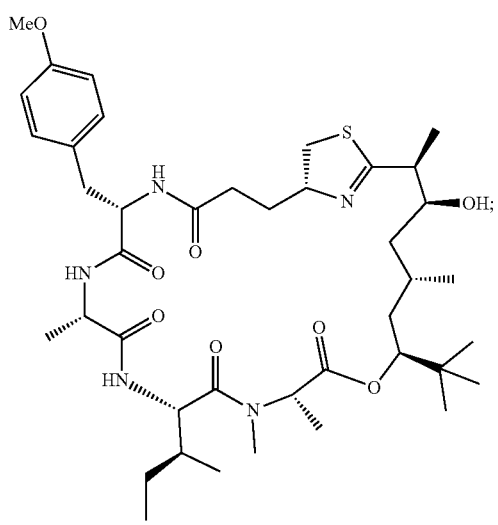

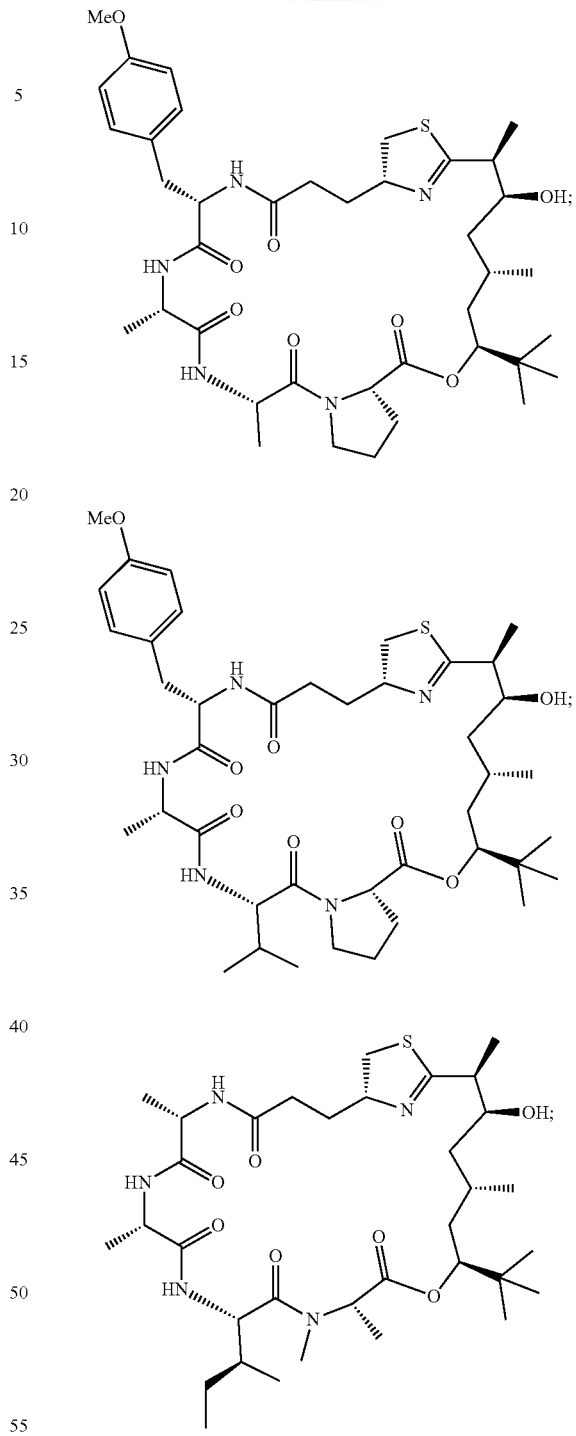

or a pharmaceutically acceptable salt thereof.

7. A method of treating a subject suffering from colon cancer, comprising administering a compound of claim 1, or a pharmaceutically acceptable salt thereof.

8. The method of claim 7, wherein the cancer is solid tumor or metastatic tumor.

9. A pharmaceutical composition comprising a compound of claim 1, or a pharmaceutically acceptable salt thereof, and a pharmaceutically acceptable carrier.

10. A process to prepare a compound of formula 17:

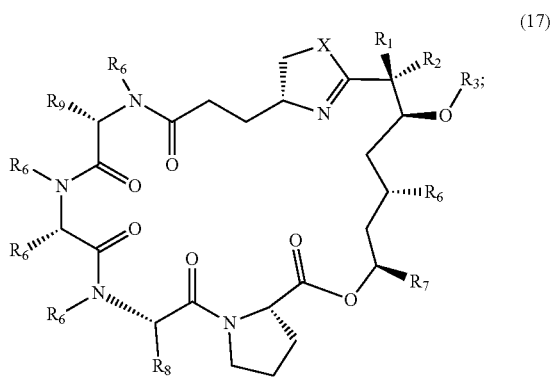

(17)

wherein the process comprises the step of reacting a compound of formula 18,

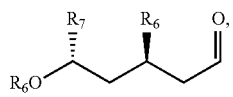

with a compound of formula 19,

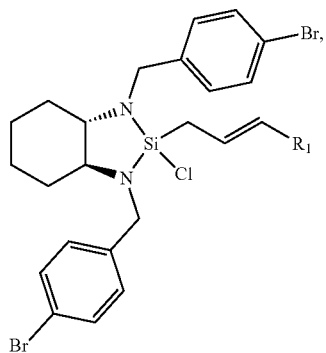

to afford a compound of formula 20,

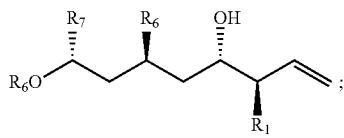

wherein:
X is S or O;
$R_1$ is optionally substituted alkyl;
$R_2$ is H;
$R_3$ is H, optionally substituted alkyl, or —C(O)alkyl;
each $R_6$ is independently H, optionally substituted alkyl, or —C(O)alkyl;
each $R_7$ and $R_8$ are independently H or optionally substituted alkyl; and
$R_9$ is H, optionally substituted alkyl, or optionally substituted aralkyl.

11. The compound of claim 1, or a pharmaceutically acceptable salt thereof, wherein $R_1$ is alkyl.

12. The compound of claim 1, or a pharmaceutically acceptable salt thereof, wherein $R_1$ is methyl.

13. The compound of claim 1, or a pharmaceutically acceptable salt thereof, wherein $R_2$ is H or methyl.

14. The compound of claim 1, or a pharmaceutically acceptable salt thereof, wherein $R_1$ is alkyl; and $R_2$ is H or methyl.

15. The compound of claim 1, or a pharmaceutically acceptable salt thereof, wherein $R_1$ is methyl; and $R_2$ is H or methyl.

16. The compound of claim 1, or a pharmaceutically acceptable salt thereof, wherein the compound is

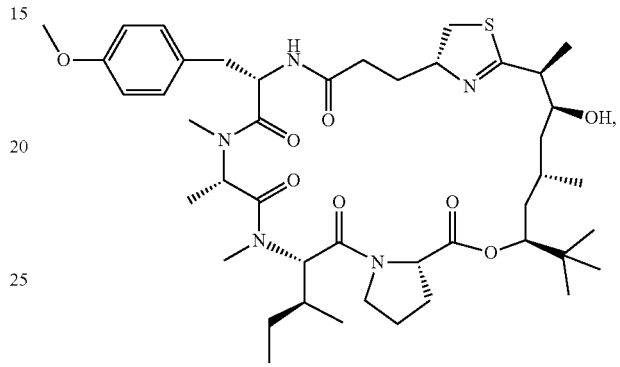

or a pharmaceutically acceptable salt thereof.

17. The compound of claim 1, or a pharmaceutically acceptable salt thereof, according to Formula 32b:

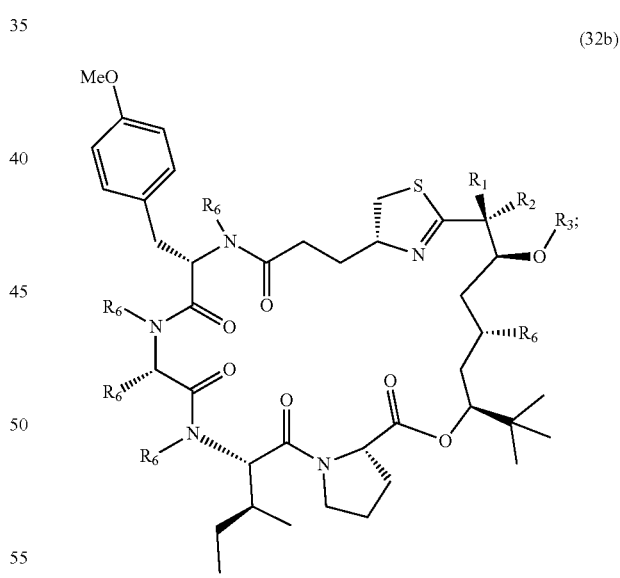

(32b)

or a pharmaceutically acceptable salt thereof;
wherein $R_1$ is optionally substituted alkyl;
$R_2$ is H or optionally substituted alkyl;
$R_3$ is H; and
each $R_6$ is independently H or methyl.

18. The compound of claim 17, or a pharmaceutically acceptable salt thereof, wherein $R_1$ is alkyl.

19. The compound of claim 17, or a pharmaceutically acceptable salt thereof, wherein $R_1$ is methyl.

20. The compound of claim 17, or a pharmaceutically acceptable salt thereof, wherein $R_1$ is alkyl; and $R_2$ is H or methyl.

* * * * *